(12) United States Patent
Holmes et al.

(10) Patent No.: US 7,384,640 B1
(45) Date of Patent: Jun. 10, 2008

(54) MUTANT CHOLERA HOLOTOXIN AS AN ADJUVANT

(75) Inventors: Randall K. Holmes, Golden, CO (US); Michael G. Jobling, Aurora, CO (US); John H. Eldridge, Fairport, NY (US); Bruce A. Green, Pittsford, NY (US); Gerald E. Hancock, Honeoye Falls, NY (US); Joel A. Peek, Brentwood, TN (US)

(73) Assignees: Wyeth Holdings Corporation, Madison, NJ (US); The United States of America as represented by the Uniformed Services University of the Health Sciences, Washington, DC (US)

( * ) Notice: Subject to any disclaimer, the term of this patent is extended or adjusted under 35 U.S.C. 154(b) by 0 days.

(21) Appl. No.: 09/806,370

(22) PCT Filed: Sep. 30, 1999

(86) PCT No.: PCT/US99/22520

§ 371 (c)(1),
(2), (4) Date: Oct. 3, 2001

(87) PCT Pub. No.: WO00/18434

PCT Pub. Date: Apr. 6, 2000

(51) Int. Cl.
*A61K 39/106* (2006.01)

(52) U.S. Cl. .............. 424/201.1; 424/361.1; 424/252.1; 435/252.3; 435/472; 435/69.3; 530/350; 536/23.7

(58) Field of Classification Search .......... 424/450, 424/89, 5, 190.1, 256.1, 203.1, 278.1, 185.1, 424/186.1, 236.1, 184.1, 240.1, 241.1, 257.1, 424/261.1, 93.2, 93.4, 197.11, 9.2, 234.1, 424/239.1, 247.1, 276.1, 254.1, 832; 800/288; 435/456, 235.1, 69, 172.3, 72, 97, 170, 197, 435/69.1, 320.1, 25, 69.3; 536/23.72, 23.7; 514/25; 530/350, 241.1
See application file for complete search history.

(56) References Cited

U.S. PATENT DOCUMENTS

| | | | |
|---|---|---|---|
| 4,666,829 A | | 5/1987 | Glenner et al. |
| 5,171,568 A | * | 12/1992 | Burke et al. ............ 424/89 |
| 5,182,109 A | | 1/1993 | Tamura |
| 5,601,831 A | * | 2/1997 | Green et al. .......... 424/256.1 |
| 5,679,352 A | * | 10/1997 | Chong et al. ......... 424/256.1 |
| 5,709,879 A | * | 1/1998 | Barchfeld et al. ....... 424/450 |
| 5,770,203 A | * | 6/1998 | Burnette et al. ...... 424/190.1 |
| 5,925,546 A | * | 7/1999 | Pizza et al. ........... 435/69.3 |
| 5,965,354 A | * | 10/1999 | Burke et al. ............. 435/5 |
| 5,972,336 A | * | 10/1999 | Michetti et al. ....... 424/184.1 |
| 6,245,337 B1 | * | 6/2001 | St. Geme, III et al. .. 424/256.1 |
| 6,290,962 B1 | * | 9/2001 | Michetti et al. ....... 424/185.1 |
| 6,395,964 B1 | * | 5/2002 | Arntzen et al. .......... 800/288 |
| 6,514,503 B1 | * | 2/2003 | Gizurarson et al. ..... 424/278.1 |
| 6,558,677 B2 | * | 5/2003 | Zollinger et al. ....... 424/234.1 |
| 6,685,949 B1 | * | 2/2004 | Gu et al. .............. 424/251.1 |
| 2003/0113345 A1 | * | 6/2003 | Clements .............. 424/203.1 |
| 2004/0176571 A1 | * | 9/2004 | Green et al. ............ 530/350 |
| 2004/0181036 A1 | * | 9/2004 | Green et al. ............ 530/350 |

FOREIGN PATENT DOCUMENTS

| | | | |
|---|---|---|---|
| WO | WO-92/19265 | | 11/1992 |
| WO | 93/13202 | * | 7/1993 |
| WO | WO 93/13202 | | 7/1993 |
| WO | 95/17211 | * | 6/1995 |
| WO | WO 95/17211 A1 | | 6/1995 |
| WO | WO 96/06627 | | 3/1996 |
| WO | 97/02348 | * | 1/1997 |
| WO | WO 97/02348 | | 1/1997 |
| WO | WO 97/05267 | | 2/1997 |
| WO | 97/29771 | * | 8/1997 |
| WO | WO 97/29771 | | 8/1997 |
| WO | WO 98/32461 | | 7/1998 |
| WO | WO 98/42375 | | 10/1998 |
| WO | WO 98/45324 | | 10/1998 |
| WO | WO-99/27944 | | 6/1999 |
| WO | WO-02/098368 A2 | | 12/2002 |
| WO | WO-02/098369 A2 | | 12/2002 |

OTHER PUBLICATIONS

Glineur, C et al, Importance of ADP-ribosylation in morphological changes of PC12 cells induced by cholera toxin. Infection and Immunity, vol. 62(10), 1994, pp. 4176-4185.*

Locht, C et al, In R. Rappuoli, Bacterial protein toxins, supplement 19, Gustav Fisher Verlag, New York, 1990, pp. 89-90.*

Vadheim, KL et al, Microb. Pathog. Nov. 1994, vol. 17(5), pp. 339-346. Expression and mutagenesis of recombinant cholera toxin A subunit.*

O'Neal, C.M. et al, Journal of Virology, vol. 72(4), pp. 3390-3393, Apr. 1998, Rotavirus 2/6 viruslike particles administered intranasally with cholera toxin, *Escherichia coli* heat labile toxin (LT) and LT-R192G induce protection from rotavirus challen.*

(Continued)

*Primary Examiner*—Ginny Allen Portner
(74) *Attorney, Agent, or Firm*—Howson & Howson LLP; Alan M. Gordon

(57) ABSTRACT

A mutant cholera holotoxin featuring a point mutation at amino acid 29 of the A subunit, wherein the glutamic acid residue is replaced by an amino acid other than aspartic acid, is useful as an adjuvant in an antigenic composition to enhance the immune response in a vertebrate host to a selected antigen from a pathogenic bacterium, virus, fungus or parasite. In a particular embodiment, the amino acid 29 is histidine. The mutant cholera holotoxin may contain at least one additional mutation in the A subunit at a position other than amino acid 29. The antigenic composition may include a second adjuvant in addition to the mutant cholera holotoxin.

29 Claims, 21 Drawing Sheets

OTHER PUBLICATIONS

Orkin, SH et al, Dec. 7, 1995, Report and Recommendations of the Panel to assess the NIH investment in Research on gene therapy (see entire document).*

Lobet, Y et al, Infection and Immunity, vol. 59(9), pp. 2870-2879, Sep. 1991.*

Jobling, MG et al, Journal of Bacteriology, Jul. 2001, vol. 183(13), pp. 4024-4032.*

Feil, Ik et al Molecular Microbiology, vol. 20(4), pp. 823-832, 1996.*

Glineur, C et al , Infection and Immunity, vol. 62(10), pp. 4176-4185, 1994.*

Zhang, Rong-Guang et al, J. Mol. Biol., 1995, pp. 563-573, vol. 251, The three dimensional crystal structure of Cholera toxin.*

Vadheim, KL et al, Microbial pathogenesis, vol. 17, pp. 339-346, 1994.*

Zhang et al (1995, p. 564, Figure 1, reference of record).*

Gilneur et al (1994, reference of record).*

Zhu et al., "Intragastric Immunization with Recombinant *H. pylori* Urease Formulated with Attenuated Cholera Toxin Elicits Systemic, Mucosal and Protective Immune Responses in C57BL/6 Mice", *FASEB J.*, 13(4) Part 1: A291, Meeting Information: Annual Meeting of the Professional Research Scientists for Experimental Biology.

Jobling et al., "Biological and Biochemical Characterization of Variant A. Subunits of Cholera Toxin Constructed by Site-Directed Mutagenesis", *J. Bacteriol.*, 183(13): 4024-4032 (Jul. 2001).
Jobling et al., "Identification of Motifs in Cholera Toxin A1 Polypeptide that are Required for its Interaction with Human ADP-Ribosylation Factor 6 in a Bacterial Two-Hybrid System", *Proc. Natl. Acad. Sci.* USA, 97(26):14662-14667 (Dec. 19, 2000).
Pizza et al., "Mucosal Vaccines: Non-Toxid Derivatives of LT and CT as Mucosal Adjuvants", *Vaccine*: 2534-2541 (Mar. 21, 2001).
M. Guiliani et al., "Mucosal Adjvanticity and Immunogenicity of LTR72, A Noval Mutant of *Escherichia coli* Heat Labile Enterotoxin with Partial Knockout of ADP-Ribosyltransferase Activity", *J. Exp. Med.*, 187(7):1123-1132 (Apr. 6, 1998).
Jobling, Michael G., Analysis of the Structure and Function of Cholera Toxin A Subunit, Abstracts of the General Meeting-1991, American Society for Microbiology, p. 59, Abstract No. B-205.
Glineur,Corine, Importance of ADP-Ribosylation in the Morphological Changes of PC12 Cells Induced by Cholera Toxin, Infection and Immunity, Oct. 1994, pp. 4176-4185, vol. 62, No. 10.
Lycke, N., Strong Adjuvant Properties of Cholera Toxin on Gut Mucosal Immune Responses to Orally Presented Antigens, Immunology, 1986, pp. 301-308, vol. 59.
McKenzie, Sara J., Cholera Toxin B Subunit as a Carrier Protein to Stimulate A Mucosal Immune Response, The Journal of Immunology, Oct. 1984, pp. 1818-1824, vol. 133, No. 4.
Mekalanos, John J., Cholera Toxin Genes: Nucleotide Sequence, Deletion Analysis and Vaccine Development, Nature, Dec. 8, 1983, pp. 551-557, vol. 306.
Nedrud, John, Oral Immunization Against Respiratory Viruses in Mice, Advances in Mucosal Immunology, 1995, vol. 371B, pp. 1595-1598.
Elson, Charles O., Generalized Systemic and Mucosal Immunity in Mice After Mucosal Stimulation with Cholera Toxin, The Journal of Immunology, Jun. 1984, pp. 2736-2741, vol. 132, No. 6.
Elson, Charles O., Cholera Toxin Feeding Did Not Induce Oral Tolerance in Mice and Abrogated Oral Tolerance to an Unrelated Protein Antigen, The Journal of Immunology, Dec. 1984, pp. 2892-2897, vol. 133, No. 6.
Richards, C.M., Enhancement of the Immune Response to Non-replicating Herpes Simplex Virus Type-1 Preparations by Mucosal Administration in the Presence of Cholera Toxin, Vaccine, 1997, pp. 1065-1069, vol. 15, No. 10.
Yamamoto, Shingo, Mutants in the ADP-ribosyltransferase Cleft of Cholera Toxin Lack Diarrheagenicity but Retain Adjuvanticity, J. Exp. Med., Apr. 7, 1997, pp. 1203-1210, vol. 185, No. 7.
Pachuk et al., "Humoral and Cellular Immune Response to Herpes Simplex Virus-2 Glycoprotein D Generated by Facilitated DNA Immunization of Mice", in Current Topics in Microbiology and Immunology, Koprowski et al., Eds., Springer-Verlag, Berlin: vol. 226, pp. 79-89 (1998).
Audibert et al., "Adjuvants: current status, clinical perspectives and future prospects", Immunology Today Jun. 1993 14:281-284.
Bazin et al., "Predominant contribution of IgA antibody-forming cells to an immune response detected in extraintestinal lymphoid tissues of germ-free mice exposed to antigen by the oral route" J. Immunol. Oct. 1970 105:1049-1051.
Brandtzaeg et al., "Immune functions of human nasal mucosa and tonsils in health and disease", in Immunology of the Lung and Upper Respiratory Tract, Bienenstock, J. (Ed.) McGraw-Hill, New York 1984 p. 28.
Brandtzaeg et al., "Immunohistochemical characterization of local immunoglobulin formation in Crohn's disease of the ileum", Scand. J. Gastroenterol. 1976 11:447-457.
Crabbe et al., "Antibodies of the IgA type in intestinal plasma cells of germfree mice after oral or parenteral immunization with ferritin", J. Exp. Med. Oct. 1969 130:723-744.
Craig et al., "Peyer's patches: an enriched source of precursors for IgA-producing immunocytes in the rabbit" J. Exp. Med. Jul. 1971 134:188-200.
Cuatrecasas, P., "Gangliosides and membrane receptors for cholera toxin", Biochem. Aug. 1973 12:3558-3566.
Gill et al., "ADP-ribosylation of membrane proteins catalyzed by cholera toxin: basis of the activation of adenylate cyclase", Proc. Natl. Acad. Sci. Jul. 1978 75:3050-3054.
Gill, D.M., "The arrangement of subunits in Cholera toxin", Biochem. 1976 15:1242-1248.
Hanson, L.A., "Comparative immunological studies of the immune globulins of human milk and of blood serum", Intl. Arch. Allergy Appl. Immunol. 1961 18:241-267.
Holmes et al., "Cholera toxin and related enterotoxins of gram-negative bacteria" in Handbook of Natural Toxins: Bacterial Toxins and Virulence Factors in Disease vol. 8, Moss et al (Eds.) Marcel Dekker, Inc., New York 1995 pp. 225-255.
Holmes, R.K., "Heat-labile enterotoxins (*Escherichia coli*)" in Guidebook to Protein Toxins and Their Use in Cell Biology, Montecucco and Rappuoli (Eds.) Oxford University Press, Oxford, England 1997.
Janeway and Travers (Eds), "The Immune System in Health and Disease" in Immunobiology Second Edition, Current Biology Ltd., London, Great Britian 1996.
Jobling et al., "Fusion proteins containing the A2 domain of cholera toxin assemble with B polypeptides of cholera toxin to form immunoreactive and functional holotoxin-like chimeras", Infect Immun. Nov. 1992, 60(11):4915-24.
Kassis et al., "Mechanism of action of cholera toxin on intact cells. Generation of A1 peptide and activation of adenylate cyclase", J. Biol. Chem. Oct. 1982 257:12148-12152.
Mekalanos et al., "Enzymic activity of cholera toxin. II. Relationships to proteolytic processing, disulfide bond reduction, and subunit composition", J. Biol. Chem. Jul. 1979 254:5855-5861.
Mestecky et al., "Selective induction of an immune response in human external secretions by ingestion of bacterial antigen", J. Clin. Invest. Mar. 1978 61:731-737.
Shi et al., GENBANK Accession No. AAC34728, 1993.
Solari et al., "The biosynthesis of secretory component and its role in the transepithelial transport of IgA dimer", Immunology Today 1985 6:17-20.
Tebbey et al., "Effective mucosal immunization against respiratory syncytial virus using purified F protein and a genetically detoxified cholera holotoxin, CT-E29H", Vaccine, Jun. 1, 2000;18(24):2723-34.
Tomasi et al., "The selective occurrence of gamma-1A globulins in certain body fluids", J. Clin. Invest. Oct. 1963 42: 1552-1560.

Welsh et al., "ADP-Ribosylation factors: A family of guanine nucleotide-binding proteins that activate cholera toxin and regulate vesicular transport", in Handbook of Natural Toxins: Bacterial Toxins and Virulence Factors in Disease vol. 8, Moss et al. (Eds.) Marcel Dekker, Inc., New York 1995 pp. 257-280.

Connell et al., "Initial studies of the structural signal for extracellular transport of cholera toxin and other proteins recognized by *Vibrio cholerae*", Infect Immun. Oct. 1995;63(10):4091-8.

Sandkvist et al., "General secretion pathway (eps) genes required for toxin secretion and outer membrane biogenesis in *Vibrio cholerae*", J Bacteriol. Nov. 1997;179(22):6994-7003.

* cited by examiner

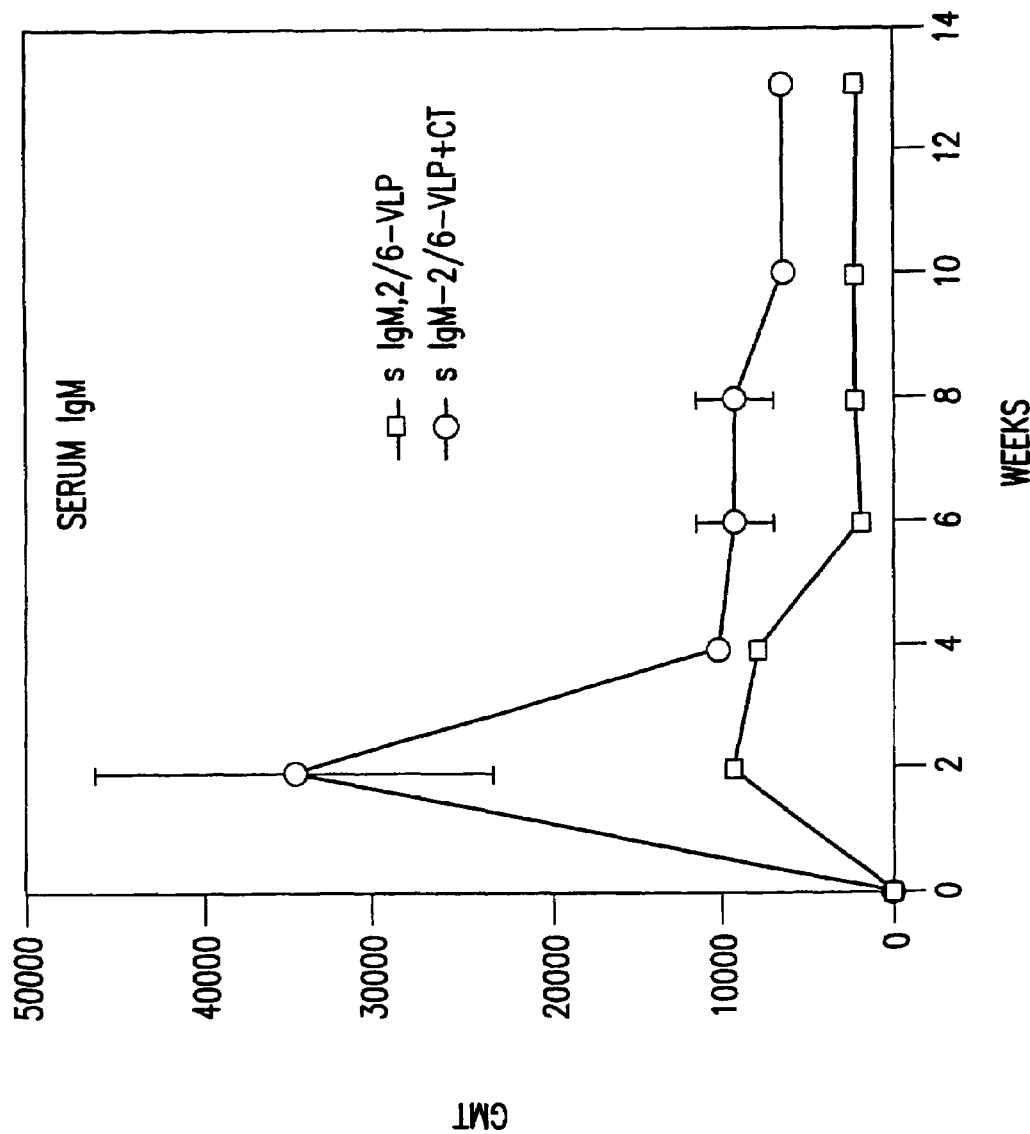

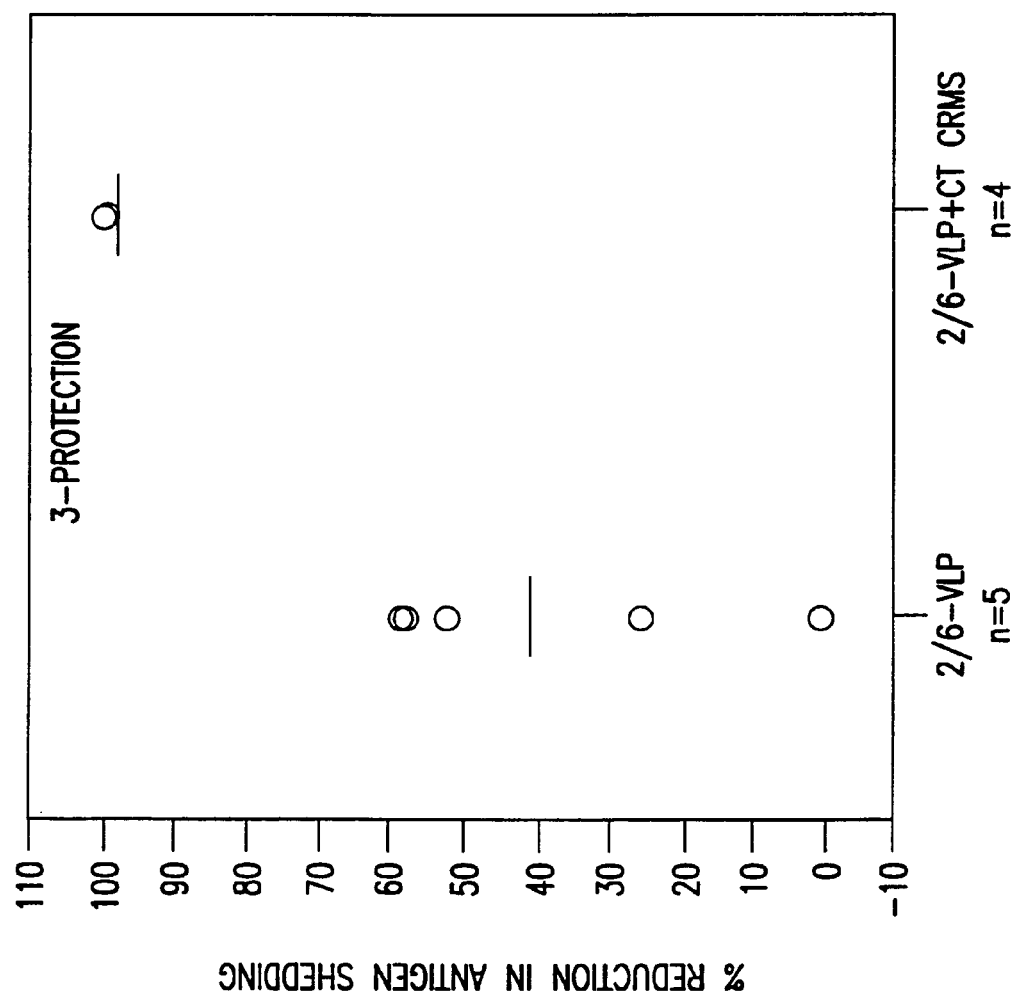

US 7,384,640 B1

MUTANT CHOLERA HOLOTOXIN AS AN ADJUVANT

FIELD OF THE INVENTION

This invention relates to the use of an immunogenic mutant cholera holotoxin having reduced toxicity compared to a wild-type cholera toxin and a substitution other than aspartic acid for the glutamic acid at position 29 of the A subunit of the cholera holotoxin as an adjuvant to enhance the immune response in a vertebrate host to a selected antigen.

BACKGROUND OF THE INVENTION

The immune system uses a variety of mechanisms for attacking pathogens. However, not all of these mechanisms are necessarily activated after immunization. Protective immunity induced by immunization is dependent on the capacity of the vaccine to elicit the appropriate immune response to resist or eliminate the pathogen. Depending on the pathogen, this may require a cell-mediated and/or humoral immune response.

A substance that enhances the immune response when administered together with an immunogen or antigen is known as an adjuvant.

The Gram-negative bacterium *Vibrio cholerae* (*V. cholerae*) is the causative agent of the gastrointestinal disease cholera. The diarrhea caused by *V. cholerae* is due to the secretion of cholera toxin (CT).

CT comprises a single A subunit (CT-A), which is responsible for the enzymatic activity of the toxin, and five identical B subunits (CT-B), which are involved in the binding of the toxin to intestinal epithelial cells, as well as other cells which contain ganglioside $GM_1$ on their surface. Together, the CT-A and CT-B subunits comprise a holotoxin. The sequence of CT has been described (Bibliography entry 1).

CT a is hexaheteromeric complex consisting of one A polypeptide and five identical B polypeptides (2). The B pentamer is required for binding to the cell surface receptor ganglioside $GM_1$ (3). The A subunit can be proteolytically cleaved within the single disulfide-linked loop between C187 and C199 to produce the enzymatically active A1 polypeptide (4) and the smaller polypeptide A2, which links fragment A1 to the B pentamer (5). Upon entry into enterocytes, CT-A1 ADP-ribosylates a regulatory G-protein (Gsα), which leads to constitutive activation of adenylate cyclase, increased intracellular concentration of cAMP, and secretion of fluid and electrolytes into the lumen of the small intestine (6). In vitro, ADP-ribosyl transferase activity of CT is stimulated by the presence of accessory proteins called ARFs (7), small GTP-binding proteins known to be involved in vesicle trafficking within the eukaryotic cell.

The need for effective immunization procedures is particularly acute with respect to infectious organisms which cause acute infections at, or gain entrance to the body through, the gastrointestinal, pulmonary, nasopharyngeal or genitourinary surfaces. These areas are bathed in mucus, which contains immunoglobulins consisting largely of secretory IgA (8, 9, 10). This antibody is derived from large numbers of IgA-producing plasma cells which infiltrate the lamina propria regions underlying these mucosal membranes (11, 12). IgA is specifically transported to the lumenal surface through the action of the secretory component (13).

However, parenteral immunization regimens are usually ineffective in inducing secretory IgA responses. Secretory immunity is most often achieved through the direct immunization of mucosally-associated lymphoid tissues. Following their induction at one mucosal site, the precursors of IgA-producing plasma cells extravasate and disseminate to diverse mucosal tissues where final differentiation to high-rate IgA synthesis occurs (14, 15, 16). Extensive studies have demonstrated the feasibility of mucosal immunization to induce this common mucosal immune system (17), but with rare exceptions the large doses of antigen required to achieve effective immunization have made this approach impractical for purified vaccine antigens. Among the strategies investigated to overcome this problem is the use of mucosal adjuvants. It is known that CT is one of the most potent adjuvants, and that the co-administration of CT with an unrelated antigen results in the induction of concurrent circulating and mucosal antibody responses to that antigen (18). Thus, CT can act as an adjuvant.

It would be preferable to use as an adjuvant a form of the CT holotoxin that has reduced toxicity so as to reduce the undesirable symptoms of diarrhea caused by wild-type CT. Thus, there is a need to identify a mutant CT holotoxin which is able to enhance the immune response while reducing the toxicity of the CT holotoxin.

SUMMARY OF THE INVENTION

Accordingly, it is an object of this invention to utilize a mutant form of the CT holotoxin that has reduced toxicity compared to a wild-type CT as an adjuvant in an antigenic composition to enhance the immune response in a vertebrate host to a selected antigen from a pathogenic bacterium, virus, fungus or parasite.

These objects of the invention are achieved with a mutant cholera holotoxin featuring a point mutation at amino acid 29 of the A subunit, wherein the glutamic acid residue is replaced by an amino acid other than aspartic acid. In a particular embodiment of this invention, the amino acid 29 is histidine. The mutated CT (also referred to as CT-CRM) is useful as an adjuvant in an antigenic composition to enhance the immune response in a vertebrate host to a selected antigen from a pathogenic bacterium, virus, fungus or parasite. The mutant CT is produced by site-directed mutagenesis of the DNA encoding the wild-type CT using conventional techniques. The antigenic composition may further comprise a diluent or carrier.

The invention is also directed to methods for increasing the ability of an antigenic composition containing a selected antigen from a pathogenic bacterium, virus, fungus or parasite to elicit the immune response of a vertebrate host by including an effective adjuvanting amount of a mutant cholera holotoxin, wherein the holotoxin has reduced toxicity compared to a wild-type CT and the glutamic acid at amino acid position 29 of the A subunit of the cholera holotoxin is replaced by an amino acid other than aspartic acid, in particular a histidine.

The invention further relates to plasmids containing isolated and purified DNA sequences comprising DNA sequences which encode an immunogenic mutant cholera holotoxin having a substitution other than aspartic acid for the glutamic acid at position 29 of the A subunit of the cholera holotoxin, and wherein such a DNA sequence is operatively linked to an arabinose inducible promoter, as well as to suitable host cells transformed, transduced or transfected with such plasmids. The immunogenic mutant cholera holotoxin is produced by transforming, transducing or transfecting a host cell with a plasmid described above

BRIEF DESCRIPTION OF THE FIGURES

FIG. 14 depicts protection of 2/6-VLP immunized BALB/c and CD-1 mice following challenge with murine rotavirus. FIG. 14A depicts a comparison of percent reduction in antigen shedding (PRAS) between mice immunized with 2/6-VLPs with (n=5) or without (n=4) CT-$CRM_{E29H}$. PRAS for each mouse (•) and the mean of each group (–) were calculated.

DETAILED DESCRIPTION OF THE INVENTION

Figure 1:
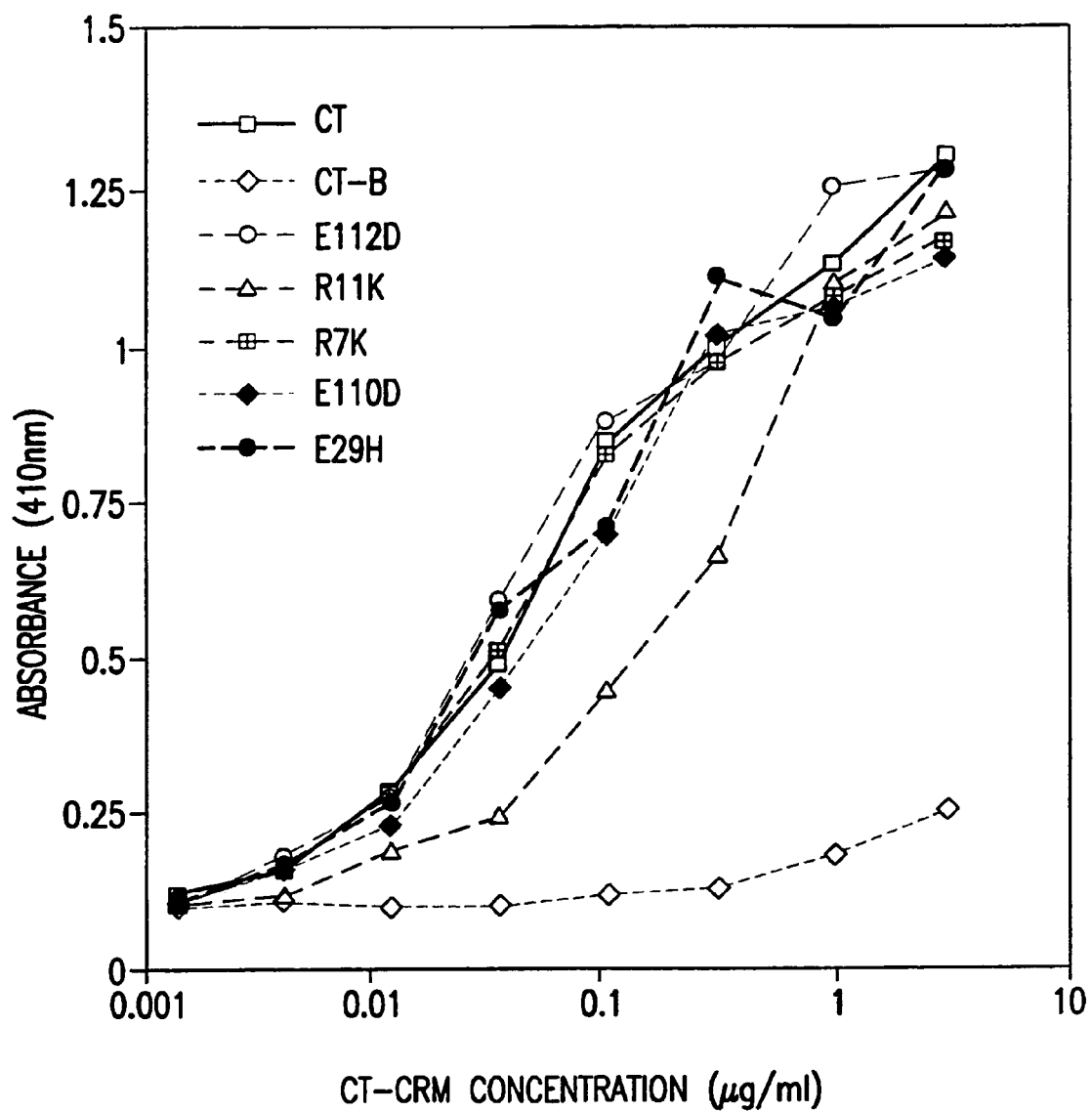
FIG. 1 depicts the capacity of CT-CRMs to bind ganglioside $GM_1$. Each CT-CRM was diluted three-fold at an initial concentration of 3 µg/ml and tested in duplicate. The binding capacity was expressed as the mean absorbance at 410 nm for each dilution.

The utility of mutant forms of CT as adjuvants for antigenic compositions is described herein. A set of mutant CT clones (CT-CRMs) in *E. coli* was generated. The data indicate that the CT-CRM with superior adjuvanting properties is the mutant with a nonconservative amino acid substitution (glutamic acid to histidine) at position 29 in the A subunit (CT-$CRM_{E29H}$). The cumulative data demonstrate that CT-$CRM_{E29H}$ is a holotoxin and is less toxic than wild-type CT. Importantly, CT-$CRM_{E29H}$ is able to augment mucosal and systemic immune responses following either intragastric (IG) or intranasal (IN) administration of disparate vaccine antigens. These vaccine antigens are from either bacterial or viral pathogens. Results in the murine models of *Helicobacter felis*, rotavirus and respiratory syncytial virus (RSV) infection indicate that the immune responses facilitated by intragastric or intranasal immunization with a CT-$CRM_{E29H}$-prepared vaccine are protective. The data indicate that CT-$CRM_{E29H}$ is at least as active as an adjuvant as wild-type CT. Even in the presence of pre-existing anti-CT immune responses, CT-$CRM_{E29H}$ is able to serve as a mucosal adjuvant.

The mutant CT-A retained its ability to assemble with CT-B to form a holotoxin that resembled wild-type CT in its adjuvanticity, but exhibited reduced toxicity compared to a wild-type CT. The B subunits may have their native sequence or may themselves be mutated.

The resulting reduced level of toxicity provides an altered CT for use as an adjuvant. The immunogenic mutant CT according to the present invention exhibits a balance of reduced toxicity and retained adjuvanticity, such that the protein functions as an adjuvant while being tolerated safely by the vertebrate host immunized with the antigenic composition.

The antigenic compositions of the present invention modulate the immune response by improving the vertebrate host's antibody response and cell-mediated immunity after administration of an antigenic composition comprising a selected antigen from a pathogenic bacterium, virus, fungus or parasite and an effective adjuvanting amount of a mutant CT, where the CT has reduced toxicity compared to a wild-type CT and the glutamic acid at position 29 of the A subunit of the cholera holotoxin is replaced by an amino acid other than aspartic acid. In a particular embodiment of this invention, the amino acid 29 is histidine.

As used herein, the term "the holotoxin has reduced toxicity" means that the CT-CRM mutant, such as the CT-CRM$_{E29H}$ mutant, exhibits a substantially lower toxicity per unit of purified toxin protein compared to the wild-type CT, which enables the mutant to be used as an adjuvant in an antigenic composition without causing significant side effects.

As used herein, the term "effective adjuvanting amount" means a dose of the CT-CRM mutant, such as the CT-CRM$_{E29H}$ mutant, which is suitable to elicit an increased immune response in a vertebrate host. The particular dosage will depend upon the age, weight and medical condition of the host, as well as on the method of administration. Suitable doses are readily determined by persons skilled in the art.

Five CT-CRMs were generated as described in Example 1 below with the following mutations in the A subunit:

| Amino Acid | Native | Mutant | Abbreviation |
| --- | --- | --- | --- |
| 7 | arginine | lysine | CT-CRM$_{R7K}$ |
| 11 | arginine | lysine | CT-CRM$_{R11K}$ |
| 29 | glutamic acid | histidine | CT-CRM$_{E29H}$ |
| 110 | glutamic acid | aspartic acid | CT-CRM$_{E110D}$ |
| 112 | glutamic acid | aspartic acid | CT-CRM$_{E112D}$ |

The phenotypic effects of these mutations on structure and function of CT were then assessed.

The variant CT-A's R7K, E29H, E110D and E112D were able to assemble into immunoreactive holotoxin as determined by a ganglioside GM$_1$ binding assay (FIG. 1). However, a portion of purified R11K did not appear to be a holotoxin when tested with the polyclonal antibodies described in Example 2.

Each holotoxin variant was tested in a Y-1 adrenal tumor cell assay (19) to determine its residual toxicity compared to wild-type CT holotoxin. The results presented in Table 2 demonstrated that CT-CRM$_{E29H}$ and commercial CT-B (Sigma) had 1.2% residual toxicity. The 1.2% residual toxicity associated with commercial CT-B was most likely due to contaminating A subunit (approximately 0.5%). The residual toxicity of the remaining CT-CRMs with mutations at amino acid positions 7, 11, 110, or 112 were less than or equal to 0.4%.

CT-CRM$_{E29H}$ was tested in the patent mouse gut weight assay (20) to estimate intestinal fluid accumulation as an in vivo measure of toxicity. The results presented in Table 3 demonstrated that CT-CRM$_{E29H}$ was significantly less active in stimulating an increase in fluid accumulation into the intestinal tract of mice than was wild-type CT.

Each CT-CRM was also compared to CT in an ADP-ribosyltransferase activity assay. The results were generally in agreement with those generated in the Y-1 adrenal cell assay and suggested that mutation in the A1 subunit resulted in diminished ADP-ribosyltransferase activity by the various CT-CRMs when compared to wild-type CT (Table 4). The mutant with the largest enzyme activity appeared to be CT-CRM$_{E29H}$. This activity was approximately 10% that of wild-type CT.

Trypsinization at 37° C. of CT-CRM$_{E29H}$ caused cleavage of CT-A into fragments A1 and A2 in a manner indistinguishable from treatment of wild-type CT based on Western blot analyses. This provides further evidence that the structure of CT-CRM$_{E29H}$ is similar to that of wild-type CT.

The apparent differences in activity of CT-CRM$_{E29H}$ in the Y-1 adrenal tumor cell and ADP-ribosylation activity assays are due to trypsin activation of the mutant holotoxin in the latter assay. Thus, the lack of CT-A cleavage into A1 and A2 subunits due to the reduced protease activity in E. coli contributes to the attenuation of the E. coli-expressed CT-CRM$_{E29H}$. Collectively, the accumulated data show that CT-CRM$_{E29H}$ is a holotoxin that binds to ganglioside GM$_1$ and is significantly less toxic than wild-type CT.

A series of studies was conducted to evaluate the efficacy of CT-CRM$_{E29H}$ as a mucosal adjuvant for compositions containing bacterial or viral antigens which have been identified as vaccine candidates as follows: (1) Nontypable Haemophilus influenzae (NTHi) recombinant P4 protein, also known as protein "e" (rP4) (21), recombinant NTHi P6 protein (rP6) (22), and purified native Haemophilus influenzae adherence and penetration (Hap$_S$) protein (23); (2) Helicobacter pylori recombinant Urease protein (rUrease) (24); (3) Neisseria meningitidis Group B recombinant class 1 pilin (25) and Neisseria meningitidis Group B class 1 outer membrane protein (26); (4) Respiratory syncytial virus purified native fusion protein (RSV F) (27); and (5) 2/6-virus-like particles of rotavirus (28).

CT-CRM$_{E29H}$ was compared to four other CT mutants and wild-type CT as an adjuvant for the NTHi rP4 and rP6 proteins. The results indicated that the five different CT-CRMs augmented the capacity of rP4 and rP6 proteins to elicit systemic humoral immune responses (Tables 5 and 6). For example, two weeks after tertiary IN immunization the anti-rP4 IgG antibody titers of mice immunized with rP4 and rP6 proteins formulated with either CT-CRM$_{E29H}$ or CT-CRM$_{E110D}$ were 40 times greater that of mice immunized with the recombinant proteins in PBS alone (Table 5). The antibody titers of mice administered the recombinant proteins plus wild-type CT holotoxin were elevated 20-fold. The anti-rP4 antibody titers of mice immunized with the CT-CRM$_{R11K}$ were elevated 10-fold.

Even more dramatic differences were observed when the sera were examined for anti-native P6 antibody titers (Table 6). Two weeks after secondary IN immunization the serum anti-native P6 antibody titers of mice immunized with either the CT-CRM$_{E29H}$ or CT-CRM$_{E110D}$ formulated vaccines were more than 30 times greater than that of mice immunized with rP6 plus PBS. In comparison, the vaccine prepared with wild-type CT elicited anti-native P6 antibody titers that were 90 times greater than that generated by the PBS prepared formulation. The anti-native P6 antibody titers of mice immunized with either the CT-CRM$_{E112D}$, CT-CRM$_{R7K}$, or CT-CRM$_{R11K}$ preparations were only two to four times greater than that of recipients immunized with rP4 plus rP6 formulated with PBS alone.

An examination of the protein-specific antibodies in the mucosal secretions two weeks after tertiary immunization further indicated that the CT-CRMs facilitated the generation of local immune responses against the rP4 protein. Moreover, the anti-rP4 antibody titers were comparable to those induced by wild-type CT (Table 7). Local antibody titers were not detected against native P6 protein (data not shown). Thus, the data when taken together suggested that the most propitious mutant CTs for generating both systemic and local antibody responses against rP4 and rP6 proteins were the CT-CRMs which contained a mutation at either position 29 or 110.

An additional study was performed to confirm the potential of CT-CRM$_{E29H}$ as an adjuvant and determine the appropriate dose for IN immunization (Table 8). The results indicated that 1 µg of CT-CRM$_{E29H}$ facilitated the greatest systemic and local humoral immune responses against rP4 protein. When the dose of CT-CRM$_{E29H}$ was increased from 1 to 10 or 30 µg per dose, the data suggested that both systemic and mucosal immune responses were diminished. For example, the serum anti-P4 IgG antibody titers of mice immunized with 10 µg CT-CRM$_{E29H}$ was one-seventh that of mice immunized with the 1 µg CT-CRM$_{E29H}$ on day 48 of the study (Table 8). Moreover, the local anti-P4 IgA antibody titers from the bronchoalveolar and vaginal wash fluids of the former group were one-thirty-fourth and one-sixteenth that of the latter group of mice on day 49. The data indicated that the local and systemic humoral immune responses of mice immunized with rP4 plus rP6/CT-CRM$_{E29H}$ were essentially identical to those attained after immunization with the wild-type CT adjuvanted vaccine (Table 8).

The effect of the addition of CT-CRM$_{E29H}$ on the serum antibody responses elicited by immunization with the Hap$_S$ protein was examined. Addition of CT-CRM$_{E29H}$ helped induce a serum antibody response to the Hap$_S$ protein (Table 9). The immune response was seen in week 7 sera; no antibody titers were detected in earlier sera. The anti-Hap$_s$ ELISA titers of the sera obtained from immunized mice are shown in Table 9. The responses increased in a dose dependent manner and were augmented approximately three-fold by addition of 0.1 µg of CT-CRM$_{E29H}$. This augmentation occurred at both dosage levels.

The potential of the five different CT-CRMs to augment systemic and local humoral immune responses after intragastric (IG) immunization with the rUrease protein of *H. pylori* was assessed using a mouse model (29). The results were similar to those obtained with the NTHi proteins after intranasal administration. The data indicated that CT-CRM$_{E29H}$ was the mutant with the most potential for augmenting systemic and local humoral immune responses after IG immunization. The geometric mean serum anti-rUrease IgG (Table 10) and IgA (Table 11) antibody titers elicited by the CT-CRM$_{E29H}$ formulated vaccine were six and three times greater, respectively, than those induced by CT-CRM$_{E110D}$ on day 28 of the study. Furthermore, the serum IgG and IgA antibody titers elicited by the CT-CRM$_{E29H}$ formulated vaccine were equivalent to that generated by the vaccine containing wild-type CT.

Most importantly, IG immunization with the rUrease formulated with CT-CRM$_{E29H}$ appeared to generate the greatest local humoral immune responses (Table 12). This was most evident after the examination of the bronchoalveolar wash fluids. The anti-rUrease IgA antibody titers in the bronchoalveolar wash fluids were five times greater than that elicited by the CT-CRM$_{E110D}$ prepared vaccine. In comparison to the wild-type CT formulation, the anti-rUrease IgA antibody titers were at one-fifth the level. However, the protein-specific IgA antibody titers in the vaginal wash fluids of the group immunized with the CT-CRM$_{E29H}$ formulated vaccine were essentially equivalent to those elicited by the wild-type CT prepared vaccine (Table 12).

It was noteworthy that the data imply that parenteral immunization did not elicit remarkable rUrease-specific IgA antibodies in the bronchoalveolar wash fluids when compared to those elicited in mice immunized IG with the CT-CRM$_{E29H}$ prepared vaccine (Table 12).

Therefore, a second study was conducted to test the efficacy of the immune responses generated by rUrease formulated with CT-CRM$_{E29H}$. The data suggest that CT-CRM$_{E29H}$ is as potent as wild-type CT in supporting the induction of protective immune responses against *H. felis* (Table 13). The serum anti-rUrease IgA antibody titers of the former group were equivalent to those of the latter group of mice on day 28 of the study. The protein-specific IgA antibody titers in the sera of mice parenterally immunized with rUrease plus Stimulon™ QS-21 were 12 times greater than those of mice immunized IG with the CT-CRM$_{E29H}$ prepared vaccine. However, the protein-specific IgA antibody titers in the bronchoalveolar wash fluids of mice immunized with CT-CRM$_{E29H}$ were more than ten times greater than those of parenterally immunized mice (Table 13).

The results suggested a correlation between IG immunization and the ability of mice to clear *H. felis* from the stomach tissue. Ten days after the last challenge, 80% of the of mice immunized IG with vaccines formulated with either CT or CT-CRM$_{E29H}$ were able to clear urease-containing bacteria from the stomach tissues. In contrast, naive control mice (10%), mice immunized IG with rUrease plus PBS alone (20%), or mice immunized subcutaneously with rUrease admixed with Stimulon™ QS-21 (30%) appeared to have less ability to eradicate H. *felis* (Table 13). It was noteworthy that the data did not suggest a relationship between efficacy and protein-specific IgA antibody titers in the bronchoalveolar wash fluids. The protein-specific IgA antibody titers in the bronchoalveolar wash fluids of mice immunized IG with rUrease plus wild-type CT were one-tenth those of mice immunized with CT-CRM$_{E29H}$ (Table 13). Yet 80% protection was achieved with either vaccine. Thus, monitoring local humoral immune responses in the pulmonary tissues may have little relevance to protective immune responses that occur in the stomach.

It has been suggested by Dr. Jani O'Rourke (University of New South Wales; personal communication) that C57Bl/6 mice, unlike BALB/c mice, experience disease similar to that observed in humans after infection with *H. pylori*. To test the efficacy of the anti-rUrease immune responses facilitated by CT-CRM$_{E29H}$ to clear *H. pylori* from the gastric tissues, a separate series of studies were initiated using C57Bl/6 mice. The results suggested that IG immunization with rUrease formulated with CT-CRM$_{E29H}$ generated systemic and local humoral immune responses that were similar to those elicited by rUrease formulated with wild-type CT (Table 14). The serum and bronchoalveolar and vaginal wash fluid anti-rUrease IgA antibody titers of mice immunized with either wild-type CT or CT-CRM$_{E29H}$ prepared vaccines on day 28 of the study were indistinguishable. The only disparities were the IgA antibody titers detected in extracts of the fecal pellets from the mice immunized with the CT-CRM$_{E29H}$ prepared vaccine (Table 14), which were three times greater. It was noteworthy that the protein-specific IgA antibody titers in the feces of mice parenterally immunized with rUrease plus alum were substantially lower than those of mice IG immunized with either wild-type CT or CT-CRM$_{E29H}$ formulations (one thirty-eighth and one-fourteenth, respectively). Thus, the C57Bl/6 mouse model appeared capable of assessing the capacity of CT-CRM$_{E29H}$ to adjuvant immune responses generated after IG immunization. Moreover, the data indicated that the model was capable of defining the roles of local and systemic immune responses in protecting mucosal surfaces from *H. pylori.*

It has been reported that CT is contraindicated as an adjuvant for mucosal immune responses (30, 31). The hypothesis was that CT predisposed vaccines to elicit heightened IgE antibody titers, which are undesirable. IgE is associated with hypersensitivity and allergic reactions. It was further implied that the heat-labile toxin of *E. coli* (LT), or LT-CRMs, had less potential to elicit heightened IgE antibody titers. Hence, the conclusion was that LT or LT-CRMs are more appropriate vaccine adjuvants for the generation of mucosal immune responses. To test this hypothesis, vaccines composed is of rUrease were formulated with either CT, LT, or CT-CRM$_{E29H}$ and tested in C57Bl/6 mice for their ability to elicit IgE antibodies after IG immunization (Table 15). The data suggested that vaccines prepared with either CT-CRM$_{E29H}$ or wild-type CT were less likely than wild-type LT to generate total or urease-specific IgE antibodies in the circulation. Indeed, the implication was that vaccines formulated with CT-CRM$_{E29H}$ were less likely to generate elevated IgE antibody titers. Both the endpoint total and the rUrease-specific IgE antibody titers were one-fourth those of mice immunized with the vaccine prepared with wild-type LT (Table 15). Thus, these data suggest that, at least in a rUrease formulation, CT-CRM$_{E29H}$ is preferred over LT as an adjuvant.

Without being bound by theory, the mechanism of LT activity recently proposed by van den Akker et al. (32) presents a more likely explanation for the reduced toxicity of CT variants altered in or around E29. After cleavage of the disulfide loop and reduction of the disulfide bond linking domains A1 and A2, the loop consisting of residues 30-33 in the A1 domain is proposed to change position as a consequence of movement of the long helix of domain A2. Substitutions for E29 may alter the behavior of loop 30-33, resulting in decreased activation of CT-A1. A potential explanation for the reduced toxicity of CT-Y30WAH and CT-G34GGP may also be explained by effects on the 30-33 loop that are detrimental to activation of CT-A1. The next step in the proposed activation pathway is movement of the entire 25-36 loop, which disrupts interactions between R25 and Y55. CT-R25G showed a reduction in toxicity to a greater extent than CT-R25W, possibly because the side chains of R25 and Y55 participate in hydrophobic interactions, which may be retained by CT-R25W but not CT-R25G. The phenotypes of our variants are consistent with the model for activation of heat-labile enterotoxins proposed by van den Akker et al. (32).

A series of experiments was conducted to evaluate the efficacy of CT-CRM$_{E29H}$ as a mucosal and parenteral adjuvant for two vaccine candidates from *Neisseria meningitidis* Group B. The first candidate was a recombinant class 1 pilin (rpilin) (25). The second candidate was a class 1 outer membrane protein (PorA) expressed by a mutant meningococcal strain that did not express the class 2/3 protein (26).

A mucosal adjuvant effect was shown in a first experiment, in that rpilin-specific serum IgG antibodies were enhanced in CT-CRM$_{E29H}$ added groups, ranging from 3 to 19-fold increases in comparison to the titers obtained in mice receiving rpilin in saline (Table 16). Specific serum IgA also increased 2 to 5-fold in the mice immunized with rpilin delivered in CT-CRM$_{E29H}$ (at both 0.1 and 1.0 μg). It is noteworthy that CT-CRM$_{E29H}$ (1 μg) increased rpilin-specific IgA 3 to 10-fold in the nasal, vaginal, and broncho-alveolar washes. Furthermore, IN immunization with rpilin plus CT-CRM$_{E29H}$ significantly reduced nasal colonization by the Group B *N. meningitidis* homologous strain to the level of detection in Swiss-Webster mice (FIG. 2).

A second experiment was conducted to demonstrate that CT-CRM$_{E29H}$ enhanced protection of rpilin against a homologous meningococcal strain. As shown in Table 17, sera IgG titers of meningococcal B whole cell ELISA were increased in the rpilin plus CT-CRM$_{E29H}$ group at least four-fold compared to the homologous strain, as well as to heterologous strains FAM18 and M982 in comparison to the titers from mice receiving rpilin alone. As a control, mice immunized with KLH plus CT-CRM$_{E29H}$ did not induce sera IgG in whole cell ELISA to any of the strains tested. In Table 18, rpilin-specific IgG and IgA antibodies were substantially increased in the rpilin plus CT-CRM$_{E29H}$ group, as compared to the unadjuvanted group. Moreover, CT-CRM$_{E29H}$ as a mucosal adjuvant for rpilin protected mice against nasal colonization by the homologous Group B meningococcal strain (FIG. 3).

Next, the immunogenicity of PorA plus CT-CRM$_{E29H}$ in IN immunization was demonstrated. The group receiving PorA adjuvanted with CT-CRM$_{E29H}$ generated increased serum IgG antibodies to *N. meningitidis* H44/76 whole cells and generated 7 and 14-fold higher PorA-specific antibodies compared to the unadjuvanted PorA group (Table 19). However, serum IgA antibodies to PorA H44/76 were not detectable. There were also no PorA-specific antibodies detected in any of the mucosal secretion samples collected (Table 19).

A fourth experiment was conducted to demonstrate that CT-CRM$_{E29H}$ enhanced protection by either rpilin or PorA against a heterologous meningococcal strain. The data, particularly from Table 20, indicate that IN administration of class 1 rpilin or PorA delivered with CT-CRM$_{E29H}$ not only elicited high serum antibody titers to antigens and meningococcal whole cells, but also protected Swiss-Webster mice against nasal colonization by a heterologous strain of group B *N. meningitidis*. Specifically, CT-CRM$_{E29H}$ enhanced serum antibody response to class 1 rpilin as compared to that of the unadjuvanted group. Similarly, the adjuvanted class 1 rpilin group provided enhanced nasal clearance of the bacteria.

Next, the ability of CT-CRM$_{E29H}$ to serve as an adjuvant for meningococcal parenteral immunization was examined. As shown in FIG. 5, PorA H355 adjuvanted with either MPL™ or CT-CRM$_{E29H}$ significantly reduced nasal colonization of Group B meningococcal heterologous strain 870227. In particular, mice immunized subcutaneously with PorA H355 plus CT-CRM$_{E29H}$ had even significantly fewer colonies than the PorA H355 plus MPL™ group in the nose 24 hours post-challenge. However, bactericidal activities were detected in the sera only from the PorA and the heat killed whole cell adjuvanted with MPL™ immunized groups respectively (Table 22), but not from the PorA plus CT-CRM$_{E29H}$ group. Even though PorA adjuvanted with CT-CRM$_{E29H}$ did not elicit homologous bactericidal activities similar to that of MPL™ adjuvant, it was highly efficacious in reducing the colonization by a heterologous Group B meningococcal strain.

The capacity of CT-CRM$_{E29H}$ to augment systemic and mucosal immune responses against respiratory syncytial virus (RSV) glycoproteins was examined using the purified native fusion (F) protein. In addition, the impact of pre-existing anti-CT antibodies on the potency of CT-CRM$_{E29H}$ as an adjuvant was investigated. The results demonstrated that BALB/c mice immunized IN with F protein adjuvanted with either CT or CT-CRM$_{E29H}$ generated systemic and local anti-CT IgG and IgA antibody titers (Table 23). Moreover, the data indicated that the antibody titers generated by the formulation containing CT-CRM$_{E29H}$ were equivalent to those elicited by the formulation containing wild-type CT. For example, 10 days after secondary immunization with F protein/CT-CRM$_{E29H}$ (1 μg per dose), the serum anti-CT IgA and IgG antibody titers were only slightly lower than those of mice immunized with F protein/CT (1 μg per dose). Similar results were also obtained after examination of the vaginal wash fluids from mice immunized with F protein prepared with either 1 or 10 μg CT-CRM$_{E29H}$ (Table 23). The data therefore suggested that CT-CRM$_{E29H}$ was as immunogenic as wild-type CT.

The question of whether anti-CT immune responses could adversely affect the immunogenicity of the F antigen was addressed in a second experiment where BALB/c mice were primed first by two IN administrations with either wild-type CT or CT-CRM$_{E29H}$ in PBS alone (Table 24). Thereafter, the appropriate mice were immunized twice with F protein admixed with either wild-type CT or CT-CRM$_{E29H}$. An examination of the sera collected two weeks after the last administration (day 56) indicated that pre-existing anti-CT antibodies did not have a negative impact on the level of local or systemic anti-F protein IgA and IgG antibodies. Indeed, the data indicated that pre-existing anti-CT antibodies were beneficial for the generation of an augmented anti-F protein antibody response. This was most evident when the anti-F protein antibody titers elicited at mucosal surfaces were compared (Table 24). Two weeks after secondary immunization, the anti-F protein IgA antibody titers in the bronchoalveolar and vaginal wash fluids of mice primed first with CT-CRM$_{E29H}$ and then immunized with F protein/CT-CRM$_{E29H}$ were 7 and 17 times greater, respectively, than that of naive mice immunized solely with F protein/CT-CRM$_{E29H}$ (Table 24).

In a third experiment, systemic and mucosal immune responses of BALB/c mice immunized IN with RSV F protein and CT-CRM$_{E29H}$, CT-B or alum were assessed. Table 25 sets forth the humoral immune responses of sera collected nine days post-tertiary immunization. Mice that had received immunizations containing F protein and either 1 or 10 μg of CT-CRM$_{E29H}$ (groups 777 and 778, respectively) displayed significantly elevated titers for IgG, IgG1 and IgG2a when compared to mice immunized with F/PBS, F/AlOH or RSV (groups 784, 785 and 907, respectively). In addition, the titers generated by vaccines containing F/CT-CRM$_{E29H}$ (777 and 778) were at least equivalent to those stimulated by F protein and CTB (779 and 780).

Bronchoalveolar lavage fluids, vaginal and nasal washes were collected from the immunized animals one week post-final immunization in order to perform IgG and IgA antibody ELISAs. The data, set forth in Table 26, show titers from pools of five mice. Mice immunized with CT-CRM$_{E29H}$ elicited detectable IgA in both vaginal and nasal washes (groups 777 and 778). IgA was not seen in BALs derived from mice immunized with CT-CRM$_{E29H}$ and this represented a contrast to that seen in the BAL of RSV immunized mice (group 907) and F/CTB immunized mice (780). IgG was seen in all mucosal washes including that from the BAL. The levels of IgG seen in the washes from CT-CRM$_{E29H}$ immunized mice were comparable to those obtained by immunizing with CTB (groups 779 and 780) and live RSV.

Figure 6:
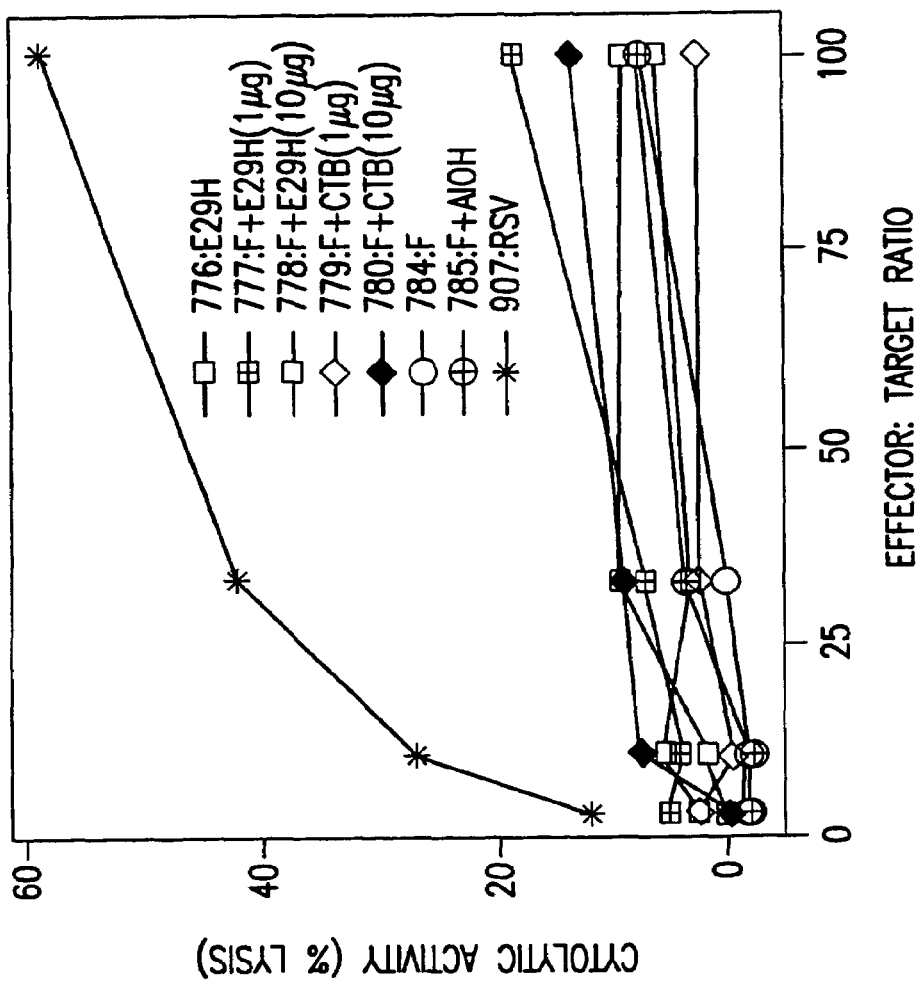
FIG. 6 depicts a first assay of the antigen-dependent cytolytic activity to respiratory syncytial virus (RSV)-infected target cells as the percentage of cell lysis versus effector:target ratio.

In a fourth experiment, the cytolytic (CTL) activity elicited by in vitro stimulated spleen cells derived from immunized mice was assessed. The data are presented in FIG. 6. Whereas RSV-immunized mice showed antigen-specific cell lysis of approximately 60%, the CTL activity of each of the remaining mice remained less than 20%. Thus, whereas CT-CRM$_{E29H}$ was able to induce both systemic and mucosal humoral immune responses to RSV F protein (Tables 25 and 26), cell-mediated immune responses to RSV-infected target cells were not observed.

In a fifth experiment, viral protection assays were performed in order to investigate whether the intranasal delivery of F/CT-CRM$_{E29H}$ facilitates protection against live RSV challenge. The data are presented in FIG. 7.

Figure 7:
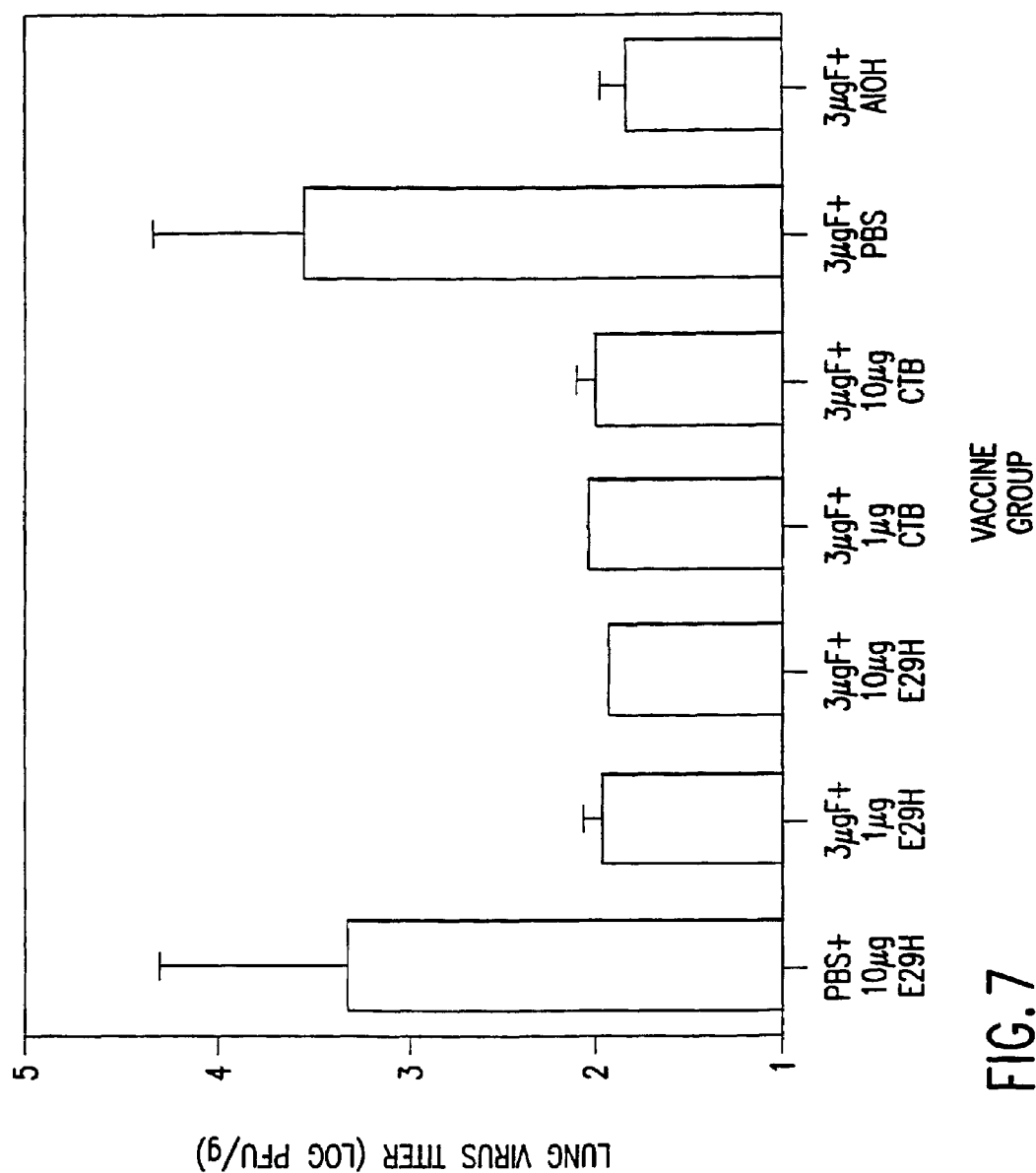
FIG. 7 depicts a first assay of the protection of mouse lung to RSV challenge by immunization with F protein plus adjuvant, where the lung virus titer is measured as $Log_{10}$ PFU per gram.

Statistical analysis by ANOVA of the results depicted in FIG. 7 is as follows:

p<0.05: F/PBS versus F/CT-CRM$_{E29H}$ (1 μg and 10 μg CT-CRM$_{E29H}$), F/CTB (1 μg and 10 μg), F/AlOH.

p>0.05: PBS/CT-CRM$_{E29H}$ versus F/PBS p>0.05: F/CT-CRM$_{E29H}$ (1 μg and 10 μg CT-CRM$_{E29H}$) versus F/CTB (1 μg and 10 μg) versus F/AlOH.

Mice that received IN vaccines containing F/CT-CRM$_{E29H}$ or F/CTB had lung viral titers comparable to those achieved in mice immunized intramuscularly with F/AlOH (p>0.05). Furthermore, intranasal immunization with F/CT-CRM$_{E29H}$ was seen to reduce lung virus titers by Log$_{10}$ 1.6 and Log$_{10}$ 1.4 compared to IN immunization with F/PBS or PBS/CT-CRM$_{E29H}$, respectively. The differences between F/CT-CRM$_{E29H}$ and F/PBS or PBS/CT-CRM$_{E29H}$ were found to be statistically significant (p<0.05).

In a sixth experiment, systemic and mucosal immune responses of BALB/c mice immunized IN with RSV F protein and CT-CRM$_{E29H}$ or alum were assessed. Table 27 sets forth the humoral immune responses of sera collected two weeks post-tertiary immunization. Mice that received immunizations containing F protein and 1 μg of CT-CRM$_{E29H}$ (group 256) displayed significantly elevated titers for IgG, IgG1 and IgG2a when compared to mice immunized with F/PBS or PBS/CT-CRM$_{E29H}$ (groups 250 and 257, respectively). No significant differences were observed in the IgG1 titers between mice immunized with F/CT-CRM$_{E29H}$ (256) and F/AlOH (258). However, IN immunization with F/CT-CRM$_{E29H}$ (256) elicited significantly elevated IgG2a titers compared to those seen by immunization with F/AlOH (258). Collectively, these results are in agreement with those presented in Table 25. Where as serum IgA was detected in groups of mice receiving F/CT-CRM$_{E29H}$, the titers were much lower than previously observed (16, 202±2, 031 for group 777 and 444±1, 458 for group 256). The reasons for the apparent difference are not clear. Nevertheless, the ability of F/CT-CRM$_{E29H}$ delivered IN to induce serum IgA is consistent in both studies and contrasts favorably with the capacity of F/AlOH in this regard.

Bronchoalveolar lavage fluids, vaginal and nasal washes were collected from the immunized animals two weeks post-final immunization in order to perform IgG and IgA antibody ELISAs. The data, set forth in Table 28, show titers from pools of five mice. Similar to the results shown in Table 26, mice immunized with CT-CRM$_{E29H}$ elicited detectable IgA in both vaginal and nasal washes (group 256). Again similar to the data presented in Table 26, IgA was not seen in BALs derived from mice immunized with CT-CRM$_{E29H}$. However, IgG was seen in all of the mucosal washes including that from the BAL. The levels of IgG observed in the washes from F/CT-CRM$_{E29H}$-immunized mice were at least comparable to those obtained by immunizing with live RSV (Table 28, groups 256 versus 259).

Figure 8:
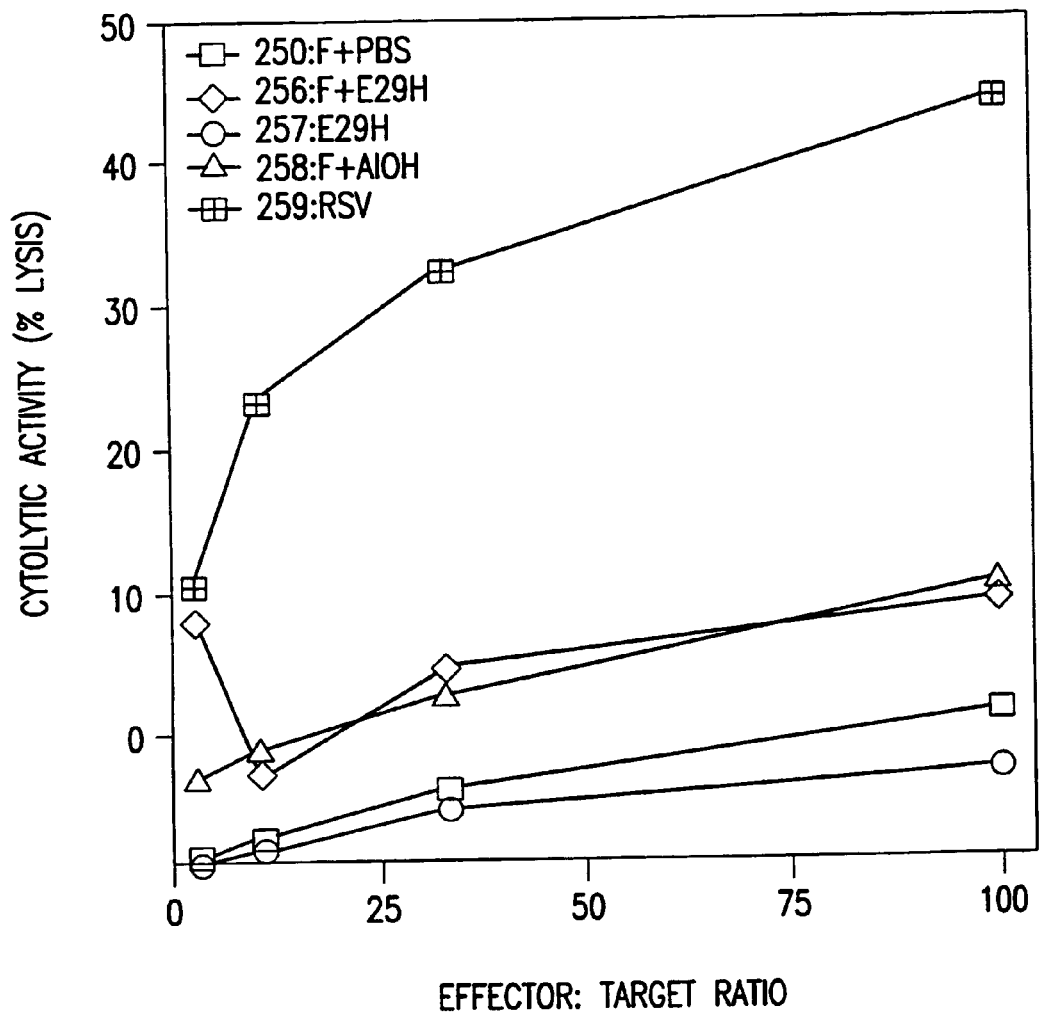
FIG. 8 depicts a second assay of the antigen-dependent cytolytic activity to RSV-infected target cells as the percentage of cell lysis versus effector:target ratio.

In a seventh experiment, the cytolytic (CTL) activity elicited by in vitro stimulated spleen cells derived from immunized mice was assessed. The data are presented in FIG. 8. Whereas RSV-immunized mice showed antigen-specific cell lysis of approximately 45%, the CTL activity of each of the remaining mice remained less than 10%. The data confirm the inability of IN immunization with F/CT-CRM$_{E29H}$ to induce a cell-mediated immune defense mechanism against RSV-infected target cells in the splenic lymphocyte population. This confirms the previous observation (FIG. 8).

In an eighth experiment, additional viral protection assays were performed in order to investigate whether the IN delivery of F/CT-CRM$_{E29H}$ facilitates protection against live RSV challenge.

Figure 9:
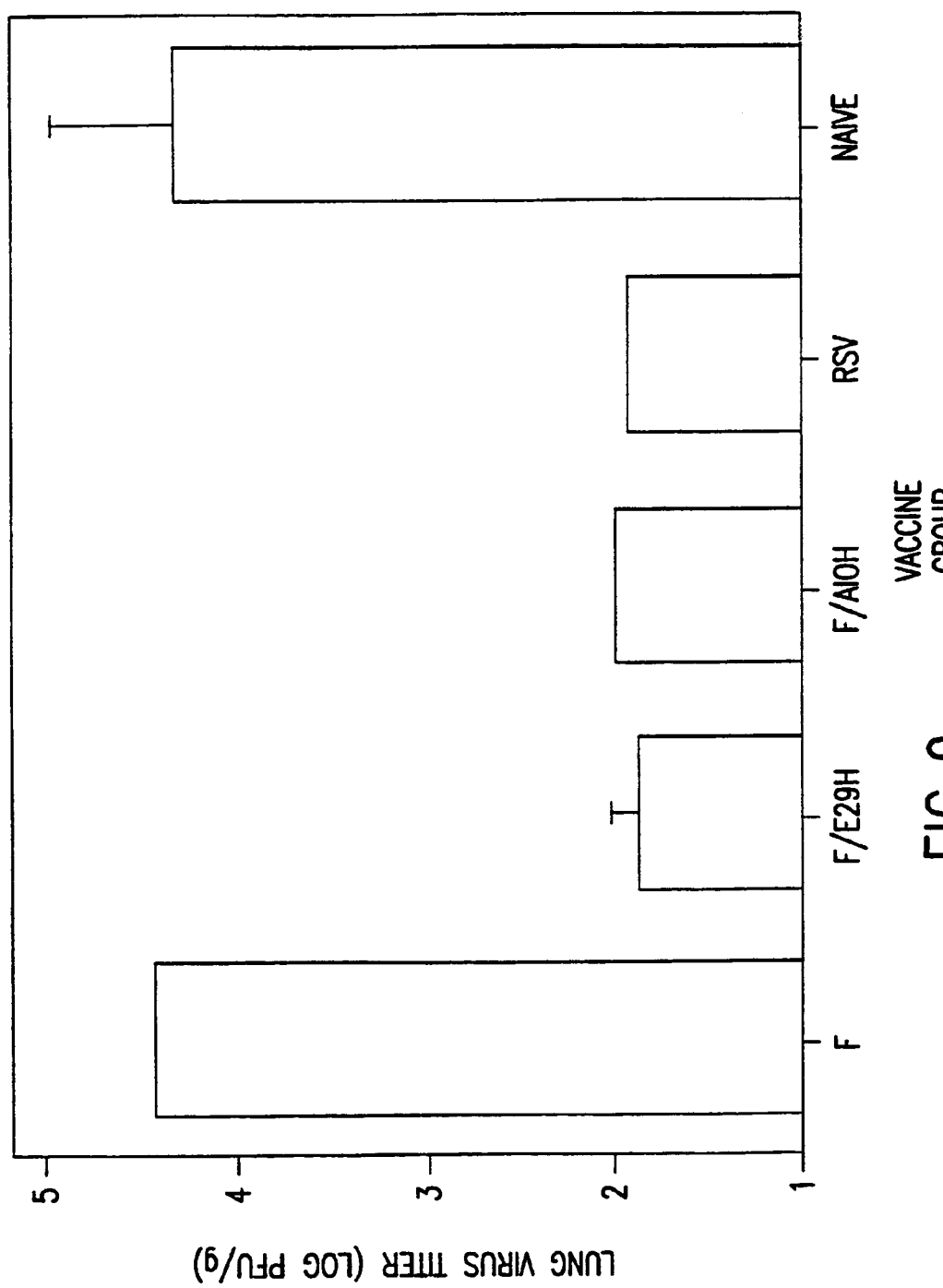
FIG. 9 depicts a second assay of the protection of mouse lung to RSV challenge by immunization with F protein plus adjuvant, where the lung virus titer is measured as $Log_{10}$ PFU per gram.

Statistical analysis by ANOVA of the results depicted in FIG. 9 is as follows:
p<0.05: F/PBS versus F/CT-CRM$_{E29H}$, F/AlOH, RSV.
p<0.05: Naïve versus F/CT-CRM$_{E29H}$, F/AlOH, RSV.
p>0.05: F/CT-CRM$_{E29H}$ versus F/AlOH, RSV.

Similar to the results depicted in FIG. 7, mice that received IN vaccines containing F/CT-CRM$_{E29H}$ controlled virus replication in the lungs to an extent which was statistically comparable (p>0.05) to that achieved in mice immunized intramuscularly with F/AlOH or IN with live RSV (Log$_{10}$ 1.87 versus Log$_{10}$ 1.99 and Log$_{10}$ 1.94, respectively). IN immunization with F/PBS (first bar), or unimmunized mice (naïve) displayed lung viral titers of Log$_{10}$ 4.5 and Log$_{10}$ 4.3, respectively. Furthermore, these groups had lung virus titers that were found to be statistically elevated (p<0.05) when compared to the virus titers obtained from mice immunized with F/CT-CRM$_{E29H}$, F/AlOH or live RSV. Therefore, the data support the conclusion that IN instillation of F/CT-CRM$_{E29H}$ protects against infectious RSV challenge.

In a ninth experiment, the anti-F serum antibody response was assessed. The results showed that anti-F protein IgG was significantly increased in mice immunized with F/CT-CRM$_{E29H}$ (0.1 or 1.0 µg) compared to those given F protein delivered in PBS alone (Table 29). In addition, F protein adjuvanted with either 0.1 or 1.0 µg CT-CRM$_{E29H}$ was at least as effective as either F/AlOH (intramuscular) or experimental infection with RSV in stimulating anti-F protein IgG responses. The magnitude of the anti-F protein antibody titers was dependent on the dose of CT-CRM$_{E29H}$ in the formulation, such that titers were significantly greater in mice that received 1.0 µg CT-CRM$_{E29H}$ versus 0.01 µg. In comparison to F/PBS, both anti-F protein IgG1 and IgG2a titers were augmented with either 0.1 or 1.0 µg CT-CRM$_{E29H}$. CT-CRM$_{E29H}$ stimulated both type 1 and type 2 immune compartments. Significantly higher serum anti-F protein IgA responses were stimulated by IN immunization with F/CT-CRM$_{E29H}$ (0.1 or 1.0 µg) compared to experimental infection with RSV. In contrast, serum IgA anti-F protein antibodies were not observed in response to F/PBS (IN) or the parenteral administration of F/AlOH (Table 29).

Anti-CT titers also followed a dose-dependent pattern consistent with the anti-F protein titers (Table 29). Statistically equivalent anti-CT titers were observed in sera obtained from mice immunized with either CT-CRM$_{E29H}$ (1.0 µg) or F/CT-CRM$_{E29H}$ (1.0 µg). However, these titers were significantly elevated compared to CT-CRM$_{E29H}$ (0.1 or 0.01 µg). In addition, the anti-CT titers in sera of mice immunized with F/CT-CRM$_{E29H}$ (0.1 µg) were statistically heightened compared to titers from mice immunized with F/CT-CRM$_{E29H}$ (0.01 µg). Therefore, the adjuvant effect of CT-CRM$_{E29H}$ for anti-F protein antibody responses is correlated (r=0.97) with the antibody response to the mutant cholera holotoxin.

In this ninth experiment, mucosal immunity was also assessed. Mucosal IgA was observed only in pooled nasal washes (NW) from mice immunized with either F/CT-CRM$_{E29H}$ (1.0 µg) or F/CT-CRM$_{E29H}$ (0.1 µg) (Table 30). In addition, mice that received IN immunizations containing purified F protein and CT-CRM$_{E29H}$ (0.01 to 1.0 µg) also had anti-F protein IgA in vaginal washes (VW). F protein-specific IgG was observed in the bronchoalveolar lavage (BAL), VW and/or NW of mice that received F/CT-CRM$_{E29H}$ (0.1 and 1.0 µg), or F/AlOH. In contrast, anti-F protein IgA was not detected in mice immunized IM with F/AlOH.

In a tenth experiment, functional immunity in mice immunized with F protein formulated with CT-CRM$_{E29H}$ was assessed. In the presence of complement, statistically heightened anti-RSV neutralizing antibodies were detected in the sera of mice that had received F protein and either 0.1 or 1.0 µg of CT-CRM$_{E29H}$, F/AlOH or RSV A2, compared to the administration of F/PBS or CT-CRM$_{E29H}$ alone (Table 31). In the absence of complement, no detectable neutralizing titers were observed in any of the groups (log$_{10}$<1.3). Consistent with the serum and mucosal antibody data (Tables 29 and 30), immunization with F/CT-CRM$_{E29H}$ (0.01 µg) was not sufficient to generate anti-RSV neutralizing antibodies.

In an eleventh experiment, immunized mice were challenged two weeks after tertiary immunization, in order to determine the ability of F/CT-CRM$_{E29H}$ to protect against subsequent infection. The results demonstrate that mice immunized with F/CT-CRM$_{E29H}$ (0.1 or 1.0 µg) were protected (Table 32). In comparison to naive mice, or those immunized with F/PBS or CT-CRM$_{E29H}$ alone, the lungs of mice immunized with F protein and either 0.1 or 1.0 µg CT-CRM$_{E29H}$ had significantly reduced virus levels. In addition, significantly reduced virus levels were observed in the nasal tissues of mice immunized with F/CT-CRM$_{E29H}$ (0.1 and 1.0 µg) compared to non-immunized naïve mice or those immunized with F/PBS. In contrast, mice immunized parenterally with F/AlOH displayed reduced viral titers in lung tissue compared to F/PBS immunized mice, but no significant reduction in nasal tissue. Overall, the IN administration of F/CT-CRM$_{E29H}$ (0.1 or 1.0 µg) was sufficient to generate both local and systemic humoral immune responses that may have contributed to the protection of respiratory tissue against subsequent live RSV challenge.

The data presented in Example 10 have illustrated a viable approach to the development of an IN vaccine for RSV F protein. The data indicate that the production of both humoral and mucosal IgG and IgA is stimulated by the IN delivery of F/CT-CRM$_{E29H}$. That the antibody titers observed were significant is demonstrated in two ways: First, each of the humoral and mucosal antibody titers that were analyzed in mice immunized with F/CT-CRM$_{E29H}$ were qualitatively similar and quantitatively elevated compared to mice immunized with F/PBS. Second, the elevated titers are translated into a biologically relevant immune response, as indicated by the observed level of protection displayed in FIGS. 7 and 9. Immunization with F/CT-CRM$_{E29H}$ significantly enhanced protection against live RSV challenge compared to immunization with F/PBS or PBS/CT-CRM$_{E29H}$.

Collectively, the data suggest a mechanism involving the neutralization of infectious virus by either mucosal or humoral immunoglobulins, that are stimulated in response to the IN immunization protocol containing F/CT-CRM$_{E29H}$.

Mice were immunized with another viral antigen, rotavirus, in the form of recombinantly-expressed VP2 and VP6 proteins. Recombinant baculovirus vectors expressing SA11 rotavirus VP2 and VP6 were constructed as described previously (28); it is known that recombinantly-expressed rotavirus structural proteins self-assemble into particles that are morphogenically indistinguishable from virions. The proteins so expressed co-assembled into 2/6-virus-like particles (VLPs).

Inbred BALB/c mice with a homogeneous genetic background were used, anticipating that they all would be responsive to immunization and thus clarify the profile of systemic and mucosal immunoglobulins to VLPs alone and when combined with CT-CRM$_{29H}$ adjuvant. Genetically heterogeneous outbred CD-1 mice were also used to determine the effect of genetic diversity on the factors involved in induction of immunity and protection.

Sera of all immunized BALB/c and CD-1 mice, except for two unresponsive orally immunized CD-1 mice, contained antibodies to both VP2 and VP6. Pre-immunization sera as well as sera of unimmunized mice detected no viral antigen in mock and or VP2-6 baculovirus infected cells. 2/6-VLP immunized sera or mAbs specific for VP6 and VP2 exposed to uninfected cells also demonstrated no reactivity (data not shown). Immunogenicity of 2/6-VLP was also confirmed by Western blot analysis using pre-challenged and immunized serum from each mouse against 2/6-VLP as well as SA11 strain of rotavirus (data not shown).

Patterns of rotavirus-specific serum IgG, IgM and IgA in the group immunized IN with 2/6-VLPs alone were similar to those in the group immunized with 2/6-VLPs and CT-CRM$_{E29H}$ (FIG. 10). However, week 13 levels of the three serum antibody isotypes were significantly higher in the animals receiving 2/6-VLPs together with CT-CRM$_{E29H}$ (FIG. 10) (P=0, P=0.004, and P=0.02 for IgG, IgM and IgA respectively). This indicated that CT-CRM$_{E29H}$ had significantly enhanced humoral responses to 2/6-VLPs. Week 13 was selected as indicative of antibody levels generated following two immunizations but prior to challenge.

As shown in FIG. 11A, BALB/c mice given VLPs IN produced a greater rotavirus specific systemic IgG response than those immunized orally. Statistically significant differences in serum IgG titers between the two groups were evident at 13 weeks (P=0). Similarly, serum IgM levels were higher in the IN group as opposed to the oral group when pre-challenge (week 13) values were analyzed (P=0) (FIG. 11B). Serum IgM levels peaked by week 2 and decreased by week 4 in the IN and mixed groups, whereas in the oral group, low but relatively constant levels of serum IgM were detected throughout the study. Peak serum IgA in orally and IN immunized animals occurred on week 4. No significant differences in serum IgA levels distinguished the three experimental groups when examined at week 13 (FIG. 1C). Overall, IN immunization generated higher levels of systemic IgG and IgM responses than oral immunization. Induction of significantly high levels of IgG and IgM in the IN group support the concept that IN immunization may be the preferred route for administration of future vaccine candidates (33). Thus, IN immunization leading to strong systemic neutralizing responses could be effective against viral pathogens that penetrate mucosal barriers.

Both IgG1 and IgG2a were found in the serum of the IN and the orally immunized BALB/c mice (FIG. 12). The IN group had statistically significantly higher levels of both IgG subclasses compared to the oral group (IgG1, P=0.005; IgG2a, P=0.05). However, there were no significant differences between subclasses within each group. These data confirm the utility of IN immunization for effective induction of both T-helper pathways (TH-1 and TH-2).

The peak level of fecal IgA for all three experimental groups occurred four weeks after the first immunization (FIG. 13A), coinciding temporally with the time at which serum IgA levels were maximal in orally and IN immunized animals (FIG. 1C). No statistically significant differences were found among the three immunization protocols when the pre-challenge fecal IgA levels were examined (FIG. 13A). Fecal IgG also was maximal on week 4 (FIG. 13B); however, the IN group had significantly more IgG on week 13 compared to oral or mixed groups (P=0 and P=0.002, respectively). In general, all 2/6-VLP immunized mice produced serum IgG, IgM and IgA, as well as fecal IgG and IgA. No fecal IgM was detected in any of the animals.

All CD-1 mice receiving 2/6-VLPs IN (n=4) and two of four mice immunized orally produced rotavirus-specific antibody responses (data not shown). To determine the profile of antibody responses more precisely, serum and fecal samples were analyzed weekly for 26 weeks. The induction pattern of serum and fecal antibodies in CD-1 mice was similar to that in the BALB/c mice (FIGS. 11 and 13).

In BALB/c mice, two IN immunizations with 2/6-VLPs and CT-CRM$_{E29H}$ proved protective (PRAS=98.7%), in contrast to IN immunization with 2/6-VLPs alone (PRAS=39%) (P=0.007) (FIG. 14A). The mixed immunization, IN followed by oral immunization, protected mice to an extent similar to oral and IN groups, indicating that in BALB/c mice mixed immunization was also effective. This demonstrated the significant augmentation in protective immune responses due to CT-CRM$_{E29H}$. BALB/c mice in all three immunization groups showed nearly complete protection from the challenge. PRAS was 99.6%, 98.8% and 98.8% for the oral, IN and the mixed groups, respectively (FIG. 14B). The unimmunized control group shed significantly more viral antigen than the three immunized groups (P=0). There were no significant differences between PRAS values for the three immunized groups.

IN immunization induced both systemic and mucosal responses in all immunized CD-1 mice and protected these animals (PRAS=97.9%) (FIG. 14C). Only two of four orally immunized CD-1 mice showed systemic and mucosal antibody responses and protection (2 of 3, PRAS 65.8%) (FIG. 14C); in contrast, all orally immunized BALB/c mice showed mucosal and systemic responses and were protected. Notably, the CD-1 mouse that did not produce an immune response was not protected from infection, whereas immune-responsive mice were protected (FIG. 14C). One mouse in the oral group, with no antibody response to immunization, died prior to the challenge. Two CD-1 mice were used as controls to reduce the number of samples in the analysis of antibody responses. However, statistical analysis clearly showed that the protection results were significant (P=0, at 95% confidence level). The oral immunization experiment was repeated with CD-1 mice under the same conditions, except that animals were challenged on week 13 rather than 26. Using four mice in the immunized groups and five mice as controls, a similar protection lev 1 was observed (PRAS=71.2%) (data not shown). Taken together, these results support those recently published by O Neal et al. (34, 35), suggesting that in CD-1 mice intranasal immunization is more effective than oral immunization.

In view of this demonstrated utility of CT-CRM$_{E29H}$ as a vaccine adjuvant, production of suitable quantities of this material is desirable. Using pIIB29H (described in Example 1), several attempts were made to express CT-CRM$_{E29H}$ in *E. coli*. The resulting yield of purified CT-CRM$_{E29H}$ holotoxin was approximately 50 µg per liter of culture medium. Initial attempts to increase CT-CRM$_{E29H}$ yield via modifications to the original plasmid, pIIB29H, to create plasmid pPX2492 (see Example 1), showed little or no effect. A moderate increase in yield was achieved through co-expression of pIIB29H, and derivatives, with *Vibrio cholerae* DsbA and *E. coli* RpoH. Co-expression and purification modifications increased the yield of CT-CRM$_{E29H}$ to approximately 2 mg per liter.

In order to increase the expression of CT-CRM$_{E29H}$, the lactose inducible promoter was replaced with an arabinose inducible promoter (Invitrogen Corporation, Carlsbad, Calif.), which was operatively linked to the DNA sequence encoding CT-CRM$_{E29H}$. During cloning it was determined that plasmid pIIB29H contained a ctxA gene from *Vibrio cholerae* strain 569B, linked to a ctxB gene from V.c. strain 2125. Cross alignment of these genes indicated seven base substitutions between the two ctxB genes and a single base change between the ctxA genes. Several of these base substitutions led to amino acid changes in the mature subunits. Of special note is the substitution between the ctxA genes which leads to an amino acid change within the A-2 portion, or the holotoxin assembly domain of the A subunit. It was not known whether the heterogeneity between these genes had a negative impact on toxin expression or holotoxin assembly; however, it was thought preferable from an evolutionary standpoint that both toxin subunit genes originate from the same source. As such, both the ctxA and ctxB genes used in the construction of the arabinose inducible system originated from *Vibrio cholerae* strain 569B. The construction of plasmid pPX7490 is described in Example 12. Production of CT-CRM$_{E29H}$ from pPX7490 is approximately 30 mg of purified material per liter of culture.

The invention further relates to plasmids containing isolated and purified DNA sequences comprising DNA sequences which encode an immunogenic mutant cholera holotoxin having a substitution other than aspartic acid for the glutamic acid at position 29 of the A subunit of the cholera holotoxin, and wherein such a DNA sequence is operatively linked to an arabinose inducible promoter, as well as to suitable host cells transformed, transduced or transfected with such plasmids by conventional techniques.

A variety of host cell-plasmid vector systems are used to express the immunogenic mutant cholera holotoxin. The vector system, which preferably includes the arabinose inducible promoter, is compatible with the host cell used. Suitable host cells include bacteria transformed with plasmid DNA, cosmid DNA or bacteriophage DNA; viruses such as vaccinia virus and adenovirus; yeast such as *Pichia* cells; insect cells such as Sf9 or Sf21 cells; or mammalian cell lines such as Chinese hamster ovary cells; as well as other conventional organisms.

A variety of conventional transcriptional and translational elements can be used for the host cell-vector system. The DNA encoding the CT-CRM is inserted into an expression system, and the promoter (preferably the arabinose inducible promoter) and other control elements are ligated into specific sites within the vector, so that when the plasmid vector is inserted into a host cell (by transformation, transduction or transfection, depending on the host cell-vector system used), the DNA encoding the CT-CRM is expressed by the host cell.

The immunogenic mutant cholera holotoxin is produced by transforming, transducing or transfecting a host cell with a plasmid described above and culturing the host cell under conditions which permit the expression of said recombinant immunogenic detoxified protein by the host cell.

Although this invention is exemplified by a CT-CRM mutant having a histidine at amino acid 29, other nonconservative mutations of the wild-type glutamic acid residue are also within the scope of this invention. Glutamic acid is an acidic (negatively charged) molecule. Therefore, a non-conservative mutation will be one in which a substitution is made to an amino acid other than aspartic acid, which is also an acidic molecule. Suitable alternative amino acids include the amino acids lysine and arginine which, like histidine, are basic (positively charged) molecules. Suitable alternative amino acids further include the amino acids with nonpolar functional groups such as alanine, isoleucine, leucine, methionine, phenylalanine, proline, tryptophan and valine, and the amino acids with uncharged polar functional groups such as asparagine, cysteine, glutamine, glycine, serine, threonine and tyrosine.

An effective amount of the mutant cholera holotoxin, wherein the holotoxin has reduced toxicity compared to a wild-type cholera holotoxin and has a substitution other than aspartic acid for the glutamic acid at position 29 of the A subunit of the cholera holotoxin, in combination with a selected antigen from a pathogenic bacterium, virus, fungus or parasite, is used to prepare an antigenic composition, wherein said holotoxin enhances the immune response in a vertebrate host to said antigen.

The antigenic compositions of this invention also comprise CT-CRM containing at least one additional mutation at a position other than at amino acid residue 29. International application WO 93/13202 (36), which is hereby incorporated by reference, describes a series of mutations in the A subunit which serve to reduce the toxicity of the cholera holotoxin. These mutations include making substitutions for the arginine at amino acid 7, the aspartic acid at position 9, the arginine at position 11, the histidine at position 44, the valine at position 53, the arginine at position 54, the serine at position 61, the serine at position 63, the histidine at position 70, the valine at position 97, the tyrosine at position 104, the proline at position 106, the histidine at position 107, the glutamic acid at position 110, the glutamic acid at position 112, the serine at position 114, the tryptophan at position 127, the arginine at position 146 and the arginine at position 192. The nucleotide sequence encoding the A subunit of the cholera holotoxin is set forth in International application WO 93/13202. International application WO 98/42375 (37) which is hereby incorporated by reference, describes making a substitution for the serine at amino acid 109 in the A subunit, which serves to reduce the toxicity of the cholera holotoxin. Therefore, using conventional techniques, mutations at one or more of these additional positions are generated.

The antigenic compositions of this invention are administered to a human or non-human vertebrate by a variety of routes, including, but not limited to, intranasal, oral, vaginal, rectal, parenteral, intradermal, transdermal (see, e.g., International application WO 98/20734 (38), which is hereby incorporated by reference), intramuscular, intraperitoneal, subcutaneous, intravenous and intraarterial. The amount of the antigen component or components of the antigenic composition will vary depending upon the identity of the antigen, as well as upon the age, weight and medical condition of the host, as well as on the method of administration. Again, suitable doses are readily determined by persons skilled in the art. It is preferable, although not required, that the antigen and the mutant CT be administered at the same time. The number of doses and the dosage regimen for the antigenic composition are also readily determined by persons skilled in the art. Protection may be conferred by a single dose of the antigenic composition, or may require the administration of several doses, in addition to booster doses at later times to maintain protection. In some instances, the adjuvant property of the mutant CT may reduce the number of doses needed or the time course of the dosage regimen.

The antigenic compositions of this invention may comprise further adjuvants in addition to CT-CRM$_{E29H}$. Examples of such adjuvants include, but are not limited to, Stimulon™ QS-21 (Aquila Biopharmaceuticals, Inc., Framingham, Mass.), MPL™ (3-O-deacylated monophosphoryl lipid A; RIBI ImmunoChem Research, Inc., Hamilton, Mont.), aluminum phosphate, aluminum hydroxide and IL-12 (Genetics Institute, Cambridge, Mass.). The antigenic compositions may also be mixed with immunologically acceptable diluents or carriers in a conventional manner.

The immunogenic mutant cholera holotoxin of this invention is suitable for use as an adjuvant in antigenic compositions containing a wide variety of antigens from a wide variety of pathogenic microorganisms, including but not limited to those from bacteria, viruses, fungi or parasitic microorganisms which infect humans and non-human vertebrates. The antigen may comprise a whole cell or virus, or one or more saccharides, proteins, protein subunits or fragments, poly- or oligonucleotides, or other macromolecular components. If desired, the antigenic compositions may contain more than one antigen from the same or different pathogenic microorganisms.

Desirable bacterial vaccines including the CT-CRM mutants as an adjuvant include those directed to the prevention and/or treatment of disease caused by, without limitation, *Haemophilus influenzae* (both typable and nontypable), *Haemophilus somnus, Moraxella catarrhalis, Streptococcus pneumoniae, Streptococcus pyogenes, Streptococcus agalactiae, Streptococcus faecalis, Helicobacter pylori, Neisseria meningitidis, Neisseria gonorrhoeae, Chlamydia trachomatis, Chlamydia pneumoniae, Chlamydia psittaci, Bordetella pertussis, Salmonella typhi, Salmonella typhimurium, Salmonella choleraesuis, Escherichia coli, Shigella, Vibrio cholerae, Corynebacterium diphtheriae, Mycobacterium tuberculosis, Mycobacterium avium-Mycobacterium intracellulare* complex, *Proteus mirabilis, Proteus vulgaris, Staphylococcus aureus, Clostridium tetani, Leptospira interrogans, Borrelia burgdorferi, Pasteurella haemolytica, Pasteurella multocida, Actinobacillus pleuropneumoniae* and *Mycoplasma gallisepticum*.

Desirable viral vaccines including the CT-CRM mutants as an adjuvant include those directed to the prevention and/or treatment of disease caused by, without limitation, Respiratory syncytial virus, Parainfluenza virus types 1-3, Influenza virus, Herpes simplex virus, Human cytomegalovirus, Human immunodeficiency virus, Hepatitis A virus, Hepatitis B virus, Hepatitis C virus, Human papillomavirus, poliovirus, rotavirus, caliciviruses, Measles virus, Mumps virus, Rubella virus, adenovirus, rabies virus, canine distemper virus, coronavirus, parvovirus, infectious rhinotracheitis viruses, feline leukemia virus, feline infectious peritonitis virus, avian infectious bursal disease virus, Newcastle disease virus, Marek's disease virus, porcine respiratory and reproductive syndrome virus, equine arteritis virus and various Encephalitis viruses.

Desirable vaccines against fungal pathogens including the CT-CRM mutants as an adjuvant include those directed to the prevention and/or treatment of disease caused by, without limitation, *Aspergillis, Blastomyces, Candida, Coccidiodes, Cryptococcus* and *Histoplasma*.

Desirable vaccines against parasites including the CT-CRM mutants as an adjuvant include those directed to the prevention and/or treatment of disease caused by, without limitation, *Leishmania major, Ascaris, Trichuris, Giardia, Schistosoma, Cryptosporidium, Trichomonas, Toxoplasma gondii* and *Pneumocystis carinii*.

The CT-CRM mutants are also suitable for inclusion as an adjuvant in polynucleotide vaccines (also known as DNA vaccines). Such vaccines may further include facilitating agents such as bupivicaine (see U.S. Pat. No. 5,593,972 (39), which is hereby incorporated by reference).

CT-CRM$_{E29H}$ was compared to wild-type CT as an adjuvant for the administration of plasmid DNA (pDNA) encoding the full length glycoprotein D of herpes simplex virus (HSV) type 2 (gD2), formulated with bupivicaine (40). The results indicated that BALB/c mice which received CT-CRM$_{E29H}$ along with pDNA vaccine for HSV-2 by the intradermal route generated a higher average cellular response than those that received pDNA HSV gD2 vaccine by itself by the intradermal route (Table 34). In addition, the average antibody response in serum for mice which received the pDNA HSV gD2 vaccine along with CT-CRM$_{E29H}$ was approximately at the same level as that seen for mice which received the pDNA HSV gD2 vaccine without adjuvant (Table 35).

Similarly, the pDNA HSV gD2 vaccine generated a gD2-specific antibody response in vaginal wash samples at levels that were comparable to those seen following the delivery of non-adjuvanted vaccine by intradermal or intramuscular routes (Table 36).

Mice immunized with the pDNA HSV gD2 vaccine adjuvanted with CT-CRM$_{E29H}$ or CT and delivered by the intradermal route generated substantially higher levels of gamma interferon than mice which received the pDNA HSV-gD2 vaccine without adjuvant (Table 37). Mice which received the CT-CRM$_{E29H}$ also generated IL-5.

Thus, CT-CRM$_{E29H}$ enhanced proliferative and gamma interferon responses when administered with a plasmid DNA vaccine against HSV.

In order that this invention may be better understood, the following examples are set forth. The examples are for the purpose of illustration only and are not to be construed as limiting the scope of the invention.

EXAMPLES

Example 1

Expression of CT Mutants

Bacterial Strains, Plasmids and Growth Conditions

*E. coli* TG1 (Amersham-Pharmacia Biotech, Piscataway, N.J.), and TX1, a nalidixic acid-resistant derivative of TG1, carrying FTc,lacI$^q$ from XL1 blue (Stratagene, LaJolla, Calif.; (41)) and CJ236 (FTc, lacI$^q$) (Bio-Rad, Hercules, Calif.) were used as hosts for cloning recombinant plasmids and expression of mutated proteins. Plasmid-containing strains were maintained on LB agar plates with antibiotics as required (ampicillin, 50 µg/ml; kanamycin 25 µg/ml; tetracycline 10 µg/ml). A complete CT operon from *V. cholerae* 0395 was subcloned into the phagemid vector pSKII⁻, under the control of the lac promoter, to create the IPTG inducible plasmid designated pMGJ67 (42).

Mutagenesis of ctxA Gene

The method of Kunkel (43) was used to select for oligonucleotide-derived mutants created in plasmid pMGJ67. The oligonucleotides used to generate the five mutant CT-CRMs are described in Table 1.

TABLE 1

Sequence of Oligonucleotides Introduced into ctxA

| Substitution | Oligonucleotide Sequence[a] | |
|---|---|---|
| R7K | AAGTTATAT<u>AA</u>GGCAGATTC | (SEQ ID NO:1) |
| R11K | CAGATTCT<u>AA</u>ACCTCCTG | (SEQ ID NO:2) |
| E29H | GACAGAGT<u>NA</u>GTACTTTGACCG | (SEQ ID NO:3) |
| E110D | CAGATGA<u>K</u>CAAGA<u>K</u>GTTTCTGC | (SEQ ID NO:4) |
| E112D | CAGATGA<u>K</u>CAAGA<u>K</u>GTTTCTGC | (SEQ ID NO:5) |

[a]Altered bases are underlined; N = any base; K = T or G.

Briefly, each single-stranded oligonucleotide was phosphorylated and used to direct second strand synthesis on a uracil-containing single-stranded DNA template rescued from the *E. coli dut ung* strain CJ236(F'Tc, pMGJ67). Following ligation and transformation of *ung*+ strain TX1, single-stranded DNA was rescued from Amp$^R$ transformants and sequenced by the dideoxy chain termination method (44).

Construction of the Plasmid Encoding CT-CRM$_{E29H}$

The plasmid encoding CT-CRM$_{E29H}$ is designated pIIB29H. The plasmid contains the polycistron of *V. cholerae* genes ctxA and ctxB which encode CT. The ctxA gene in this plasmid was mutagenized as described above to encode a histidine at amino acid position 29 of CT-A. The wild-type polycistron was also altered by removing the native ToxR inducible promoter and replacing it with a lactose inducible promoter. Furthermore, the regions encoding the ctxA and ctxB signal sequences were replaced with the signal sequence-encoding region of *E. coli* LT (LTIIb-B leader) in order to promote secretion of CT-CRM$_{E29H}$. The plasmid pIIB29H was then modified in an attempt to increase the expression of CT-CRM$_{E29H}$. The resulting plasmid, designated pPX2492, contained synthetic Shine Dalgarno sequences upstream of each of ctxA and ctxB. The two genes are genetically separated in pPX2492, unlike in *V. cholerae*, where the genes overlap. The two genes also have the LTIIb-B leader sequence upstream of each.

Expression of Mutant ctxA Alleles

Production of each variant holotoxin was tested in 5 ml cultures of TB medium (45) in 125 ml Erlenmeyer flasks at 37° C. with shaking (200 rpm). Logarithmic phase cells ($A_{600}$=0.8-1.0) were induced by the addition of IPTG to 0.4 mM, followed by growth overnight. Polymyxin B was added to 1 mg/ml, followed by incubation for 10 minutes at 37° C. Cells were removed by centrifugation, and the supernatants were assayed to determine the concentrations of holotoxin and B pentamer as described below.

Specifically, the production of CT-CRM$_{E29H}$ in *E. coli* involves the co-expression of the genes rpoH from *E. coli* and dsbA from *V. cholerae*. These gene products participate in the conformational maturation of both the A and B subunits of CT.

Example 2

The GM1 Binding Assay for Intact Holotoxin

The CT-CRMs were examined in a ganglioside GM$_1$-dependent solid phase radioimmunoassay (42) to determine whether intact holotoxin was present after purification. An enzyme-linked immunosorbent assay (ELISA) was used where ELISA plate microwells were coated overnight at 4° C. with ganglioside GM$_1$ (10 µg/ml). Thereafter, the following reagents were added in sequence with an interval of one hour incubation at room temperature: CT-CRMs (titrated from 3 µg/ml to 0.00137 µg/ml), 100 µl of rabbit anti-CT-A sera (1:1,000), and alkaline phosphatase conjugated goat anti-rabbit antibody (1:2,000). To visualize the reaction, 100 µl of p-nitrophenyl phosphate at 1 µg/ml in diethanolamine was added and incubated for 30 minutes. The reaction was stopped by adding 100 µl of 2 N NaOH and immediately read by a Microelisa autoreader. When compared to wild-type CT, the data indicated that the CT-CRMs with amino acid substitutions at positions 7, 29, 110, or 112 were intact holotoxins (FIG. 1). The results implied, however, that a portion of purified CT-CRM$_{R11K}$ did not appear to be a holotoxin.

Example 3

Y-1 Adrenal Cell Assay for Residual Toxicity of CT-CRMs

The mutant CT-CRMs were compared several times with wild-type holotoxin for toxicity in the mouse Y-1 adrenal tumor cell assay. Y-1 adrenal cells (ATCC CCL-79) were seeded in 96-well flat-bottom plates at a concentration of 10$^4$ cells per well. Thereafter, three-fold serial dilutions of CT-CRMs were added to the tumor cells and incubated at 37° C. (5% CO$_2$) for 18 hours. The cells were then examined by light microscopy for evidence of toxicity (cell rounding). The endpoint titer was defined as the minimum concentration of toxin required to give greater than 50% cell rounding. The percent of residual toxicity is calculated using the endpoint titer of wild-type CT divided by the titer elicited by CT-CRM multiplied by 100. Table 2 depicts the residual toxicity of several purified mutant holotoxins tested in the Y-1 adrenal cell assay.

TABLE 2

The toxicity for Y-1 adrenal cells
Y-1 Adrenal Cell Assay

| CT-CRM | % Residual Toxicity |
|---|---|
| E112D | 0.13 |
| E112D | 0.13 |
| R11K | 0.04 |
| R7K | 0.04 |
| E110D | 0.13 |
| E110D | 0.40 |
| E29H | 1.20 |
| CT-B | 1.20 |
| CT | 100.00 |

Example 4

Patent Mouse Gut Weight Assay

In this assay, 10 µg of wild-type CT or CT-CRM$_{E29H}$ was administered intragastrically to each group of BALB/c mice (three mice per group). Intestines were removed carefully three hours later and weighed. The results are presented in Table 3. Data are presented as the mean gut/carcass weight ratio per group.

TABLE 3

Toxicity of CT-CRM$_{E29H}$

| Assay | CT | CT-CRM$_{E29H}$ | PBS |
|---|---|---|---|
| Mouse Gut Weight (gut/carcass ratio) | 0.13 ± 0.01 | 0.09 ± 0.01[a] | 0.08 ± 0.007 |

[a]$p < 0.05$ compared to wild-type CT control, $p > 0.05$ compared to PBS.

Example 5

The ADP-Ribosyltransferase Assay

NAD$^+$:agmatine ADP-ribosyltransferase activity was measured as the release of [carbonyl-$^{14}$C]nicotinamide from radiolabeled NAD$^+$. Briefly, CT and CT-CRMs were trypsin activated and incubated for 30 minutes at 30° C. with 50 mM glycine/20 mM dithiothreitol in TEAN buffer (Tris™/EDTA/sodium azide/sodium chloride) (pH 8.0). Thereafter, the following materials were added to the reaction: 0.1 mg of soybean trypsin inhibitor, 50 mM potassium phosphate, 10 mM agmatine, 20 mM dithiothreitol, 10 mM magnesium chloride, 100 μM GTP, 3 mM dimyristoylphosphatidylcholine, 0.2% cholate, 0.03 mg of ovalbumin, 100 μM [adenine-U-$^{14}$C]NAD (DuPont NEN™, Boston, Mass.) and water to a final volume of 300 μl. After incubation for 90 minutes at 30° C., 100 μl samples were applied to columns (0.64×5 cm) of AG1-X2 (Bio-Rad) which were washed five times with 1.0 ml of distilled/deionized H$_2$O. Eluates containing [$^{14}$C]ADP-ribosylagmatine were collected for radioassay. Mean recovery of $^{14}$C in the eluate is expressed as percentage of that applied to column. The results are presented in Table 4.

TABLE 4

NAD:Agmatine ADP-Ribosyltransferase Activity

| Adjuvant | ADP-ribosylagmatine formed (nmol/hr/μg protein) | % ADP-ribosylation activity |
|---|---|---|
| CT, 10 μg | 57.1 | 100 |
| E29H, 10 μg | 6.7 | 11.7 |
| E110D, 10 μg | 0.4 | 0.7 |
| E112D, 10 μg | 0.9 | 1.6 |
| R7K, 10 μg | 0.4 | 0.7 |
| R11K, 10 μg | 0.4 | 0.7 |

Example 6

The Immune Responses of BALB/c Mice Immunized with Recombinant (r) P4 and P6 Outer Membrane Proteins of Nontypable *Haemophilus influenzae* (NTHi)

In a first experiment, five BALB/c mice per group were immunized intranasally on days 0, 21 and 35 with a 10 μl dose containing 5 μg rP4 or 10 μg rP6, plus 1 μg of the adjuvant as indicated in Tables 5 and 6 (one group did not receive adjuvant). The anti-rP4 IgG antibody titers were determined by ELISA on pooled samples collected at days 0, 21, 35 and 48 and the results shown in Table 5. The anti-rP6 IgG antibody titers were separately determined by ELISA on pooled samples collected at days 0, 21, 35 and 48 and the results shown in Table 6. The mucosal antibody responses to rP4 were also measured two weeks after the last immunization (day 49). Table 7 sets forth the IgA and IgG titers from nasal, bronchoalveolar and vaginal washes, respectively.

In a second experiment, five BALB/c mice per group were immunized intranasally on days 0, 21 and 35 with a 30 μl dose containing 5 μg rP4 or 10 μg rP6, plus ascending doses of CT-CRM$_{E29H}$ as indicated in Table 8 (other groups each received CT or CT-B; one group received no adjuvant). The serum anti-rP4 IgA and IgG antibody titers were determined by ELISA on pooled samples collected at days 21, 35 and 48 and the results shown in Table 8. The IgA and IgG titers from bronchoalveolar and vaginal washes on day 49 were also determined and are shown in Table 8.

TABLE 5

The systemic humoral immune responses of BALB/c mice immunized[a] with recombinant P4 and P6 proteins[b] formulated with mutant cholera holotoxins

| | Serum Anti-Recombinant P4 IgG Antibody Titers[c] | | | |
|---|---|---|---|---|
| Adjuvant[d] | Day 0 | Day 21 | Day 35 | Day 48 |
| None | 1,157 | 1,277 | 1,893 | 1,968 |
| CT | 751 | 1,657 | 17,589 | 45,885 |
| CT-B | 1,111 | 1,118 | 6,917 | 70,578 |
| E29H | 1,052 | 1,539 | 11,917 | 95,922 |
| E110D | 1,243 | 1,313 | 6,886 | 83,058 |
| E112D | 1,400 | 1,520 | 9,280 | 41,485 |
| R7K | 2,546 | 1,771 | 3,311 | 40,936 |
| R11K | 1,289 | 1,391 | 3,428 | 23,631 |

[a]The mice were immunized intranasally (IN, 10 μl volume) on days 0, 21 and 35.
[b]Recombinant P4 and P6 proteins were administered at 5 and 10 μg per dose respectively.
[c]Anti-recombinant P4 IgG antibody titers were determined by ELISA on pooled samples collected at the denoted times. There were 5 mice per group.
[d]CT and CT mutants were administered at 1 μg per dose.

TABLE 6

The systemic humoral immune responses of BALB/c mice immunized[a] with recombinant P4 and P6 proteins[b] formulated with mutant cholera holotoxins

| | Serum Anti-Native P6 IgG Antibody Titers[c] | | | |
|---|---|---|---|---|
| Adjuvant[d] | Day 0 | Day 21 | Day 35 | Day 48 |
| None | <100 | <100 | <100 | <100 |
| CT | <100 | <100 | 9,644 | 54,821 |
| CT-B | <100 | <100 | 875 | 7,399 |
| E29H | <100 | <100 | 3,472 | 19,638 |
| E110D | <100 | <100 | 3,666 | 22,415 |
| E112D | <100 | <100 | 426 | 9,538 |
| R7K | <100 | <100 | 529 | 3,904 |
| R11K | <100 | <100 | 248 | 3,763 |

[a]The mice were immunized intranasally (IN, 10 μl volume) on days 0, 21 and 35.
[b]Recombinant P4 and P6 proteins were administered at 5 and 10 μg per dose respectively.
[c]Anti-recombinant P6 IgG antibody titers were determined by ELISA on pooled samples collected at the denoted times. There were 5 mice per group.
[d]CT and CT mutants were administered at 1 μg per dose.

TABLE 7

The mucosal antibody responses of BALB/c mice
immunized[a] with recombinant P4 and P6 proteins[b]
formulated with mutant cholera holotoxins

| | Anti-Recombinant P4 Antibody Titer[c] | | | | | |
|---|---|---|---|---|---|---|
| | NW[d] | | BAW[d] | | VW[d] | |
| Adjuvant[e] | IgA | IgG | IgA | IgG | IgA | IgG |
| None | <5 | <5 | <5 | <5 | <50 | <50 |
| CT | <5 | <5 | <5 | 56 | 54 | <50 |
| CT-B | <5 | <5 | <5 | 99 | <50 | <50 |
| E29H | <5 | <5 | <5 | 176 | 63 | <50 |
| E110D | <5 | <5 | <5 | 144 | <50 | 98 |
| E112D | <5 | <5 | <5 | 48 | 564 | 58 |
| R7K | <5 | <5 | <5 | 56 | <50 | <50 |
| R11K | 6 | <5 | <5 | 34 | 223 | <50 |

[a]The mice were immunized intranasally (IN, 10 μl volume) on days 0, 21 and 35.
[b]Recombinant P4 and P6 proteins were administered at 5 and 10 μg per dose respectively.
[c]Anti-recombinant P4 IgG and IgA antibody titers were determined by ELISA on pooled samples collected 2 weeks after the last immunization (day 49). There were 5 mice per group.
[d]NW, BAW, and VW denote nasal wash, bronchoalveolar wash, and vaginal wash respectively.
[e]CT and CT mutants were administered at 1 μg per dose.

TABLE 8

The effect of ascending doses of CT-CRM$_{E29H}$ on the generation of local
and systemic immune responses against the recombinant P4 and P6
proteins of Haemophilus influenzae

| | Anti-Recombinant P4 Antibody Titers[a] | | | | | | | | | |
|---|---|---|---|---|---|---|---|---|---|---|
| | Sera | | | | | | Mucosal Wash Fluids[b] | | | |
| | Day 21 | | Day 35 | | Day 48 | | BAW | | VW | |
| Adjuvant | IgA | IgG | IgA | IgG | IgA | IgG | IgA | IgG | IgA | IgG |
| none | 189 | 219 | 204 | 3,833 | 334 | 17,269 | 27 | 26 | 493 | 146 |
| 1 μg CT | 145 | 741 | 1,803 | 67,470 | 5,855 | 495,735 | 864 | 2,279 | 1,446 | 1,934 |
| 10 μg CT-B | 206 | 2,531 | 650 | 34,047 | 5,838 | 989,806 | 622 | 3,674 | 1,397 | 884 |
| 1 μg CT.CRM$_{E29H}$ | 171 | 2,640 | 1,021 | 59,031 | 8,643 | 588,586 | 845 | 3,180 | 1,898 | 1,479 |
| 10 μg CT-CRM$_{E29H}$ | <100 | 498 | <100 | 6,427 | 397 | 84,176 | 25 | 175 | 122 | 31 |
| 30 μg CT-CRM$_{E29H}$ | 119 | 622 | 801 | 14,151 | 2,194 | 161,187 | 67 | 568 | 215 | 116 |

[a]The mice were immunized intranasally (IN, 30 μl volume) on days 0, 21 and 35 with recombinant P4 (5 μg) and P6 (10 μg) proteins. Anti-recombinant P4 IgG and IgA antibody titers were determined by ELISA on pooled samples collected at the indicated times. There were 5 mice per group.
[b]BAW and VW denote bronchoalveolar wash, and vaginal wash respectively.

Example 7

The Immune Responses of BALB/c Mice
Immunized with the Native Hap$_S$ Protein of NTHi NTHi strain P860295 (46) was obtained from Dr. Charles Brinton, University of Pittsburgh. It was obtained from the nasopharynx of a child with NTHi induced otitis media. NTHi strain TN106 (47) was obtained from Dr. Eric Hansen, University of Texas Southwestern Medical Center at Dallas. A streptomycin resistant mutant of TN106 was derived by selection on BHI-XV plates containing 100 μg/ml of streptomycin (Sigma, St. Louis, Mo.). This mutant was passaged twice in the nasopharynx of Balb/c mice and frozen as strain TN106.P2.

The Hap$_S$ protein from NTHi strain P860295 was purified as follows. NTHi strain P860295 was grown in BHI-XV media for 18 hours at 35° C. with aeration. The bacterial cells were pelleted by centrifugation, 10K×g at 4° C., and discarded. The supernatant was brought to 60% saturation with solid $(NH_4)_2SO_4$, held at room temperature for 2-3 hours, and the precipitate was collected by centrifugation. The precipitate was dissolved in 50 mM sodium phosphate buffer, pH 5.8, 1 mM EDTA, 50 mM NaCl (Buffer 1), and was dialyzed at 4° C. against the above buffer. A 10 ml bed volume CM Sepharose™ column (Pharmacia, Piscataway, N.J.) was equilibrated with Buffer 1, and 30 ml of the above soluble material was loaded onto the column at a flow rate of 1 ml/min. The column was washed with Buffer 1 until the $OD_{280}$ reached baseline. The fall-through material was discarded. Bound proteins were eluted from the resin using a three step gradient: (1) sodium phosphate buffer, pH 7.0, 1 mM EDTA, 50 mM NaCl; (2) sodium phosphate buffer, pH 8.0, 1 mM EDTA, 50 mM NaCl; and (3) sodium phosphate buffer, pH 8.0, 0.5 M NaCl, 1 mM EDTA. Proteins eluted in each step were pooled and saved for analysis. SDS-PAGE (48) analysis of pools indicated that the Hap$_S$ protein eluted in gradient steps 2 and 3. These pools contained highly purified Hap$_S$ and were combined.

Six week old, female Balb/c mice (ten per group) were then immunized IN with Hap$_S$ purified from NTHi strain P860295. The Hap$_S$ protein was diluted in D-PBS to 5 or 15 μg/40 μl with or without CT-CRM$_{E29H}$. Where used, the CT-CRM$_{E29H}$ was used at a dosage of 0.1 μg/mouse. Control formulations containing CT-CRM$_{E29H}$ in D-PBS, D-PBS alone and formalin fixed TN106.P2 (the NTHi challenge strain) were also administered to the mice in 40 μl volumes.

Prior to IN immunization, mice were anesthetized and then immunized by intranasal inoculation of 20 μL/nostril from a pipette. The pipette was held so the tip touched the opening of the nostril and the formulation was automatically drawn into the nostril during breathing. The mice were placed in a supine position so noses were not touching anything after administration of the formulation or the challenge. The mice were immunized at weeks 0, 1, 3, and 5. Sera were drawn at week 7. The results are shown in Table 9.

TABLE 9

Systemic humoral immune response in Balb/c mice after intranasal immunization with Hap$_S$ admixed with or without CT-CRM$_{E29H}$

| Immunogen | Dose (µg) | Adjuvant | Anti-Hap$_S$ IgG ELISA |
|---|---|---|---|
| Hap | 5 | — | 1,604 |
| Hap | 15 | — | 5,204 |
| Hap | 5 | CT-E29H | 4,653 |
| Hap | 15 | CT-E29H | 15,111 |
| — | — | CT-E29H | <500 |
| 1xPBS | — | — | <500 |
| Formalin Fixed TN106.P2 | — | — | <500 |

Example 8

The Immune Responses of BALB/c and C57Bl/6 Mice Immunized with the Recombinant (r) Urease Protein of Helicobacter pylori In a first experiment, five BALB/c mice per group were immunized as follows: Seven groups were immunized intragastrically on days 0, 2, 14 and 16 with 100 µg rUrease plus 10 µg of the adjuvant as indicated in Tables 10-12. One group was immunized with 10 µg rUrease subcutaneously in the rump; another group was immunized with 10 µg rUrease subcutaneously in the neck; both groups also received 20 µg of Stimulon™ QS-21 as an adjuvant on days 0 and 16. The anti-rUrease antibody titers were determined by ELISA on pooled samples collected on day 28. The IgG results are shown in Table 10 and the IgA results are shown in Table 11. The mucosal antibody responses to rUrease were also measured on day 29. Table 12 sets forth the IgA and IgG titers from bronchoalveolar and vaginal washes, respectively.

In a second experiment, the ability of rUrease plus adjuvant to protect mice against a challenge with H. felis was assessed. Ten BALB/c mice per group were immunized as follows: Two groups were immunized intragastrically on days 0, 2, 14 and 16 with 100 µg rUrease plus 10 µg of the adjuvant as indicated in Table 13; a control group received PBS instead of rUrease plus 10 µg of adjuvant. One group was immunized subcutaneously on days 0 and 16 with 10 µg rUrease plus 20 µg of Stimulon™ QS-21. The anti-rUrease antibody titers were determined by ELISA on pooled samples collected on day 28. The mice were also challenged with three doses of 108H. felis on days 29, 31 and 34 and were assayed for protection on day 44. Protection was assessed by the rapid urease test. In the rapid urease test, one-half stomach was incubated at 37° C. for five hours in 0.5 ml of the urease test medium containing 2% of urea and phenol red, a pH indicator, at 7 µg/ml. Urease activity generates ammonium and bicarbonate from urea, thus raising the pH and inducing a calorimetric change of the solution with a higher absorbance at 550 nm. The level of urease activity was measured by spectrophotometic analysis. The test was considered positive for H. felis when the mean of the absorbance values were two standard deviations above that of those obtained for the gastric tissues of non-infected mice. The results are shown in Table 13.

In a third experiment, two groups of C57BL/6 mice (five per group) were immunized intragastrically on days 0, 2, 14 and 16 with 100 µg rUrease plus 10 µg of the adjuvant as indicated in Table 14. A third group was immunized subcutaneously on days 0 and 16 with 10 µg rUrease plus 100 µg alum. A fourth group was immunized intragastrically on days 0, 2, 14 and 16 with 100 µg rUrease, but without adjuvant. The anti-rUrease antibody titers were determined by ELISA on pooled samples collected on day 28. Table 14 sets forth the IgA and IgG titers from sera, bronchoalveolar wash, fecal pellet extract and vaginal wash, respectively.

In a fourth experiment, five C57BL/6 mice per group were immunized as follows: Three groups of mice were immunized IG on days 0, 2, 14 and 16 with 100 µg rUrease plus 10 µg of the adjuvant as indicated in Table 15; a fourth group received no adjuvant. The anti-rUrease antibody titers were determined by ELISA on pooled samples collected on day 29. The IgA and IgG results are shown in Table 15. Table 15 also presents the IgE (PCA) and total IgE titers. PCA denotes that the IgE antibody titers were determined by the passive cutaneous anaphylaxis reaction. The PCA was performed on female Sprague-Dawley rats. The rats were sedated with ketamine/xylazine, shaved, and injected intradermally with 0.1 ml sera (serially diluted four-fold) from C57Bl/6 mice immunized with rUrease formulated with either CT, LT, or CT-CRM$_{E29H}$. The rats were sedated 48 to 60 hours later and then injected (0.1 ml) intravenously via the tail vein with 2 µg rUrease in PBS containing 1% Evan's blue dye.

TABLE 10

The effect of CT-CRMs on the generation of systemic anti-Urease IgG antibody titers in BALB/c mice
Anti-Recombinant Urease IgG Antibody Titers[a]

| Adjuvant[b] | Route[b] | Mean | SE |
|---|---|---|---|
| CT | IG | 234,010 | 43,316 |
| E29H | IG | 131,032 | 64,183 |
| R7K | IG | 17,692 | 9,271 |
| R11K | IG | 25,502 | 11,413 |
| E110D | IG | 22,299 | 8,571 |
| E112D | IG | 8,784 | 5,208 |
| CT-B | IG | 47,060 | 38,991 |
| QS-21 | SC-R | 4,038,430 | 1,702,556 |
| QS-21 | SC-N | 5,609,764 | 353,824 |

[a]The geometric mean anti-recombinant Urease antibody titers were determined by ELISA on serum samples collected on day 28. There were 5 mice per group.
[b]The mice were immunized with 10 µg rUrease subcutaneously (SC) in the rump (R), or neck (N) on days 0 and 16. Mice immunized intragastrically (IG) received 100 µg rUrease on days 0, 2, 14 and 16. The adjuvants were either Stimulon™ QS.21 (20 µg), CT (10 µg), or CT mutants (10 µg).

TABLE 11

The effect of CT-CRMs on the generation of systemic anti-Urease IgA antibody titers in BALB/c mice
Anti-Recombinant Urease IgA Antibody Titers[a]

| Adjuvant[b] | Route[b] | Mean | SE |
|---|---|---|---|
| CT | IG | 2,529 | 584 |
| E29H | IG | 1,013 | 426 |
| R7K | IG | 82 | 15 |
| R11K | IG | 153 | 39 |
| E110D | IG | 351 | 137 |
| E112D | IG | 232 | 93 |
| CT-B | IG | 455 | 280 |
| QS-21 | SC-R | 5,675 | 562 |
| QS-21 | SC-N | 4,793 | 528 |

[a]The geometric mean anti-recombinant Urease IgA antibody titers were determined by ELISA on serum samples collected on day 28. There were 5 mice per group.
[b]The mice were immunized with 10 µg rUrease subcutaneously (SC) in the rump (R), or in the neck (N) on days 0 and 16. Mice immunized intragastrically (IG) received 100 µg rUrease on days 0, 2, 14, and 16. The adjuvants were either Stimulon™ QS-21 (20 µg), CT (10 µg), or CT derivatives (10 µg).

TABLE 12

The effect of CT-CRMs on the generation of anti-Urease IgA antibody titers in the mucosal secretions of BALB/c mice
Anti-Recombinant Urease Antibody Titers[a]

| | | BAW[b] | | VW[b] | |
|---|---|---|---|---|---|
| Adjuvant[c] | Route[c] | IgA | IgG | IgA | IgG |
| CT | IG | 387 | 1005 | 3,471 | 464 |
| E29H | IG | 63 | 317 | 2,095 | 265 |

TABLE 12-continued

The effect of CT-CRMs on the generation of anti-Urease IgA antibody titers in the mucosal secretions of BALB/c mice Anti-Recombinant Urease Antibody Titers[a]

| | | BAW[b] | | VW[b] | |
|---|---|---|---|---|---|
| Adjuvant[c] | Route[c] | IgA | IgG | IgA | IgG |
| R7K | IG | <5 | 27 | 79 | 42 |
| R11K | IG | 7 | 62 | 29 | 21 |
| E110D | IG | 13 | 98 | 217 | 84 |
| E112D | IG | <5 | 17 | 991 | 108 |
| CT-B | IG | 65 | 312 | 140 | 60 |
| QS-21 | SC-R | 6 | 9816 | 809 | 10,272 |
| QS-21 | SC-N | 11 | 10,545 | 235 | 6,237 |

[a]The anti-rUrease IgG and IgA antibody titers were determined by ELISA on pooled samples collected on day 29. There were 5 mice per group.
[b]BAW and VW denote bronchoalveolar and vaginal wash respectively.
[c]The mice were immunized with 10 μg rUrease subcutaneously (SC) in the rump (R), or in the neck (N) on days 0 and 16. Mice immunized intragastrically (IG) received 100 μg rUrease on days 0, 2, 14, and 16. The adjuvants were either Stimulon™ QS-21 (20 μg), CT (10 μg), or CT derivatives (10 μg).

TABLE 13

The generation of protective immune responses in BALB/c mice immunized with recombinant urease formulated with CT or CT-CRM$_{E29H}$

| | | | IgA TITERS[a] | | No. Protected/ |
|---|---|---|---|---|---|
| Antigen[b] | Adjuvant[c] | Route | Sera | BAW[d] | Total (%)[e] |
| PBS | CT | IG | <100 | ND | 2/10 (20) |
| r Urease | CT | IG | 2,730 | 11 | 8/10 (80) |
| r Urease | E29H | IG | 1,225 | 124 | 8/10 (80) |
| r Urease | QS-21 | SC | 14,917 | 7 | 3/10 (30) |
| NONE | NONE | ND | <100 | ND | 1/10 (10) |

[a]The anti-recombinant (r) urease IgA antibody titers were determined by ELISA on pooled samples collected on day 28. There were 10 mice per group.
[b]Mice were immunized intragastrically (IG) on days 0, 2, 14 and 16 with 100 μg r urease per dose. Control mice were injected subcutaneously (SC) on days 0 and 16 with 10 μg rUrease per dose.
[c]The rUrease was formulated with either 10 μg CT or CT-CRM per dose, or mixed with 20 μg Stimulon™ QS-21 per dose.
[d]BAW denotes bronchoalveolar wash.
[e]The mice were challenged with 3 doses of $10^8$ H. felis on days 29, 31 and 34 and assayed for protection on day 44. Protection was assessed by the rapid urease test.

TABLE 14

The effects of CT-CRM$_{E29H}$ on the immune response to recombinant Urease in C57BL/6 mice Anti-Recombinant Urease Antibody Titers[a]

| | | Sera | | BAW[b] | | FP[b] | | VW[b] | |
|---|---|---|---|---|---|---|---|---|---|
| Adjuvant[c] | Route[c] | IgA | IgG | IgA | IgG | IgA | IgG | IgA | IgG |
| E29H | IG | 1,358 | 252,289 | 14 | 426 | 265 | 9 | 40 | 140 |
| CT | IG | 1,117 | 92,182 | 12 | 331 | 97 | 7 | 45 | 309 |
| Alum | SC | 2,658 | 1,012,790 | 3 | 795 | 7 | <5 | 49 | 173 |
| None | IG | 110 | 10,938 | <5 | 14 | <5 | <5 | <50 | 29 |

[a]The endpoint anti-rUrease antibody titers were determined by ELISA on pooled serum samples collected on day 28. There were 5 mice per group.
[b]BAW, FP, and VW denote bronchoalveolar wash, fecal pellet extract, and vaginal wash respectively.
[c]The mice were immunized with 10 μg rUrease subcutaneously (SC) on days 0 and 16. The mice immunized intragastrically (IG) received 100 μg rUrease on days 0, 2, 14, and 16. The adjuvants were either alum (100 μg), CT (10 μg), or CT-CRM$_{E29H}$ (10 μg)

TABLE 15

The generation of urease-specific IgE antibodies in the circulation of C57B1/6 mice immunized with recombinant urease prepared with either CT, LT, or CT-CRM$_{E29H}$

| Adjuvant[b] | Anti-rUrease Antibody Titers[a] | | | |
|---|---|---|---|---|
| | IgA | IgG | IgE (PCA)[c] | Total IgE[d] |
| NONE | 732 | 30,591 | <4 | ND |
| CT | 2,504 | 496,373 | 32 | 1591 |
| CT-CRM$_{E29H}$ | 4,039 | 477,098 | 16 | 888 |
| LT | 5,251 | 670,807 | 64 | 3589 |

[a]The endpoint IgA and IgG antibody titers were determined by ELISA on pooled serum samples collected on day 29. There were 5 mice per group.
[b]The mice were immunized intragastrically (IG) with 100 µg rUrease on days 0, 2, 14, and 16. The adjuvants were 10 µg CT, CT-CRM$_{E29H}$ or LT.
[c]PCA denotes that the IgE antibody titers were determined by the passive cutaneous anaphylaxis reaction. The PCA was performed on female Sprague Dawley rats. The rats were sedated with ketamine/xylazine, shaved, and injected intradermally with 0.1 ml sera (serially diluted 4-fold) from C57B1/6 mice immunized with rUrease formulated with either CT, LT, or CT-CRM$_{E29H}$. The rats were sedated 48 to 60 hours later and then injected (0.1 ml) intravenously via the tail vein with 2 µg rUrease in PBS containing 1% Evan's blue dye.
[d]The numbers are in ng/ml.
ND denotes not detected.

Example 9

The Immune Responses of Swiss-Webster Mice Immunized with Recombinant Class 1 Pilin and Class 1 Outer Membrane Protein of *Neisseria meningitidis*

Figure 2:
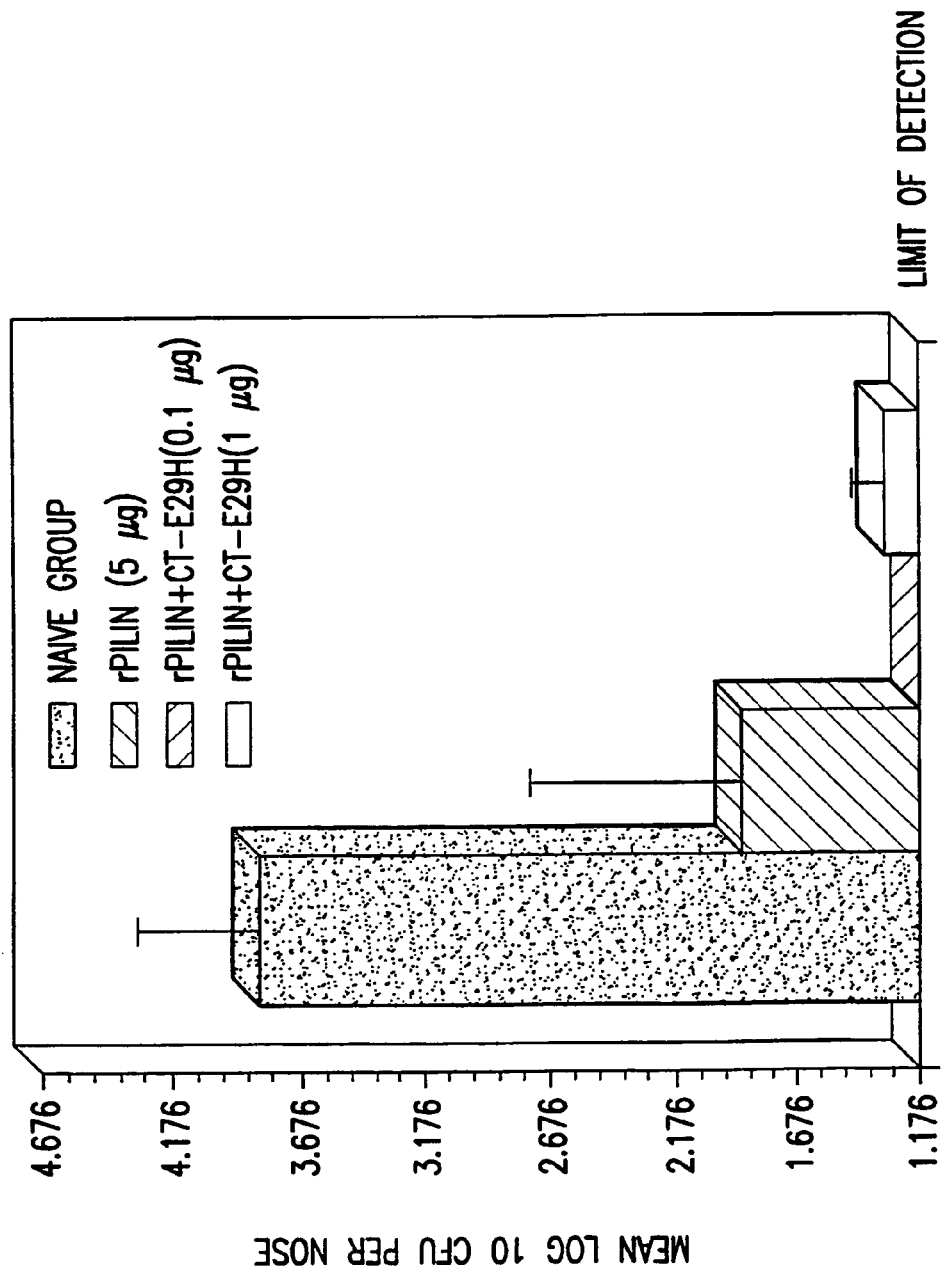
FIG. 2 depicts the reduction in nasal colonization in mean $Log_{10}$ cfu per nose in mice immunized intranasally (n=10 per group) with meningococcal recombinant pilin (rpilin) with or without CT-$CRM_{E29H}$ adjuvant, or non-immunized mice, where each group was then challenged with the homologous meningococcal bacterial strain.
Figure 3:
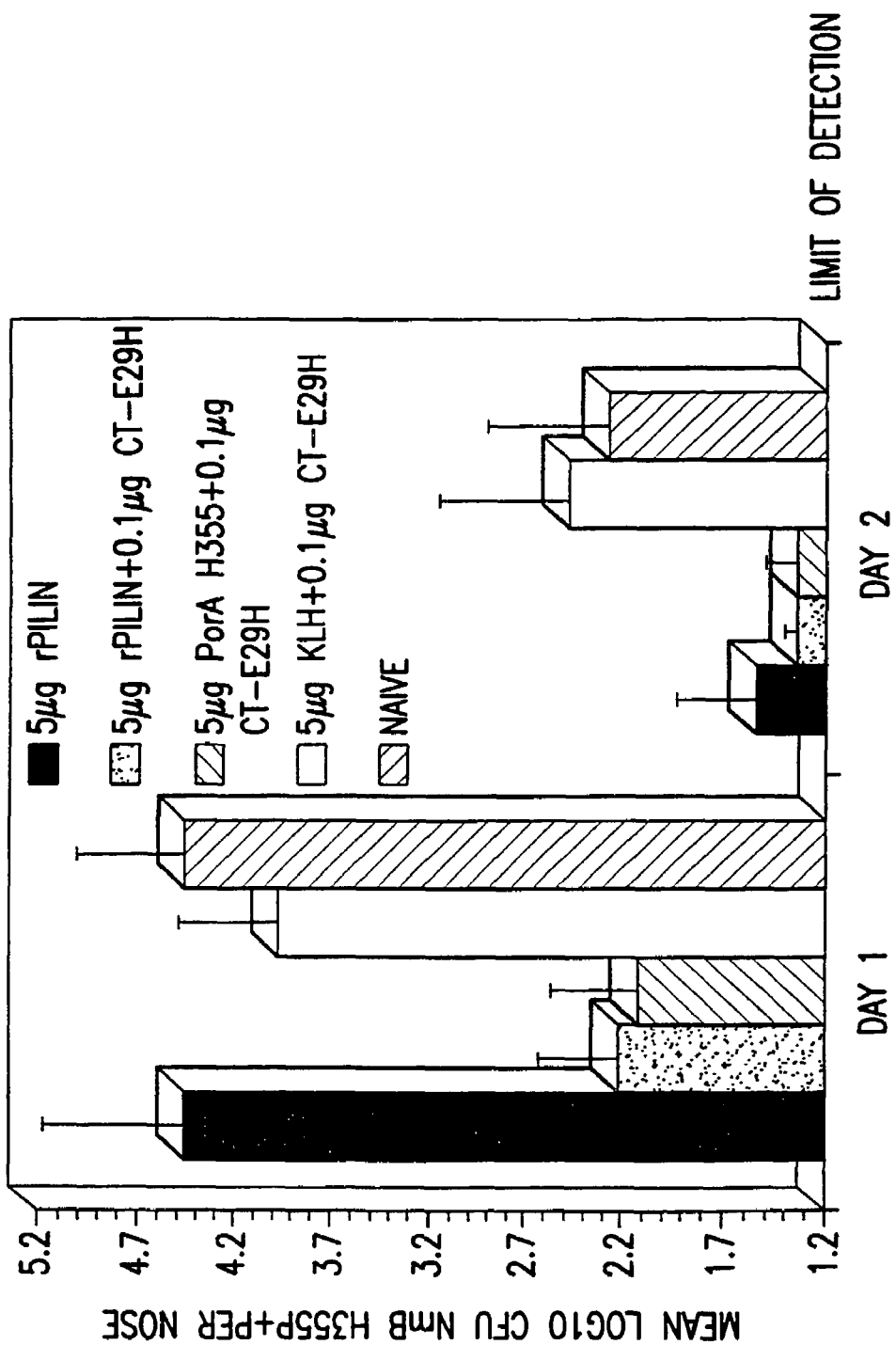
FIG. 3 depicts the reduction in nasal colonization in mean $Log_{10}$ cfu per nose in mice immunized intranasally (n=5 per group) with meningococcal rpilin with or without CT-$CRM_{E29H}$ adjuvant, meningococcal class 1 outer membrane protein (Por A) with CT-$CRM_{E29H}$ adjuvant, KLH with CT-$CRM_{E29H}$ adjuvant, or non-immunized mice, where each group was then challenged with the homologous meningococcal bacterial strain.

In a first experiment, 6-8 week-old Swiss-Webster mice (15 per group) were immunized IN (10 µl) at weeks 0, 2 and 3 with 5 µg of purified recombinant class 1 pilin (rpilin) formulated with CT-CRM$_{E29H}$ (0.1 or 1 µg/mouse). Serum samples, bronchoalveolar washes (BAW), nasal washes (NW) and vaginal washes (VW) were collected from five mice in each group for determination of serum and mucosal IgA and IgG antibodies specific to *N. meningitidis* pilin by ELISA at week 4. The results are presented in Table 16. The remaining ten mice in each group immunized in parallel were challenged IN with 2×10⁷ CFUs of the homologous *N. meningitidis* strain H355P⁺.p2IR (passed through infant rats twice) at week 4. Recovery of Group B *N. meningitidis* from nasal tissue 24 hours post-challenge was determined by quantitative culture, as shown in FIG. 2.

In a second experiment, the protection of rpilin formulated with CT-CRM$_{E29H}$ against a homologous meningococcal strain was compared to that of CT-CRM$_{E29H}$ admixed with an unrelated protein, KLH. Groups of five Swiss-Webster mice (six-week old) were immunized IN (10 µl volume) with 5 µg of rpilin with or without CT-CRM$_{E29H}$ (0.1 µg), or with PorA H355 with CT-CRM$_{E29H}$ (0.1 µg) at weeks 0, 2, and 3. Control groups were either non-immunized (naïve group) or IN immunized with KLH (5 µg) plus CT-CRM$_{E29H}$ (0.1 µg). The endpoint antibody titers were determined by whole cell and antigen-specific ELISA on pooled serum samples collected at week 4 before challenge with 1×10⁷ CFU's of meningococcal strain H355P⁺. The results are presented in Tables 17 and 18.

In a third experiment, the immunogenicity of meningococcal PorA formulated with CT-CRM$_{E29H}$ for IN immunization was assessed. Five Swiss-Webster mice per group were immunized IN on weeks 0, 2 and 3 with 20 µg/dose PorA from meningococcal strain H44/76 with or without CT-CRM$_{E29H}$ (1 µg/dose) as indicated in Table 19. The anti-PorA H44/76 antibody titers and whole cell ELISA for IgG were assayed on pooled serum and mucosal samples collected at week 4 of the experiment. The results are presented in Table 19.

Figure 4:
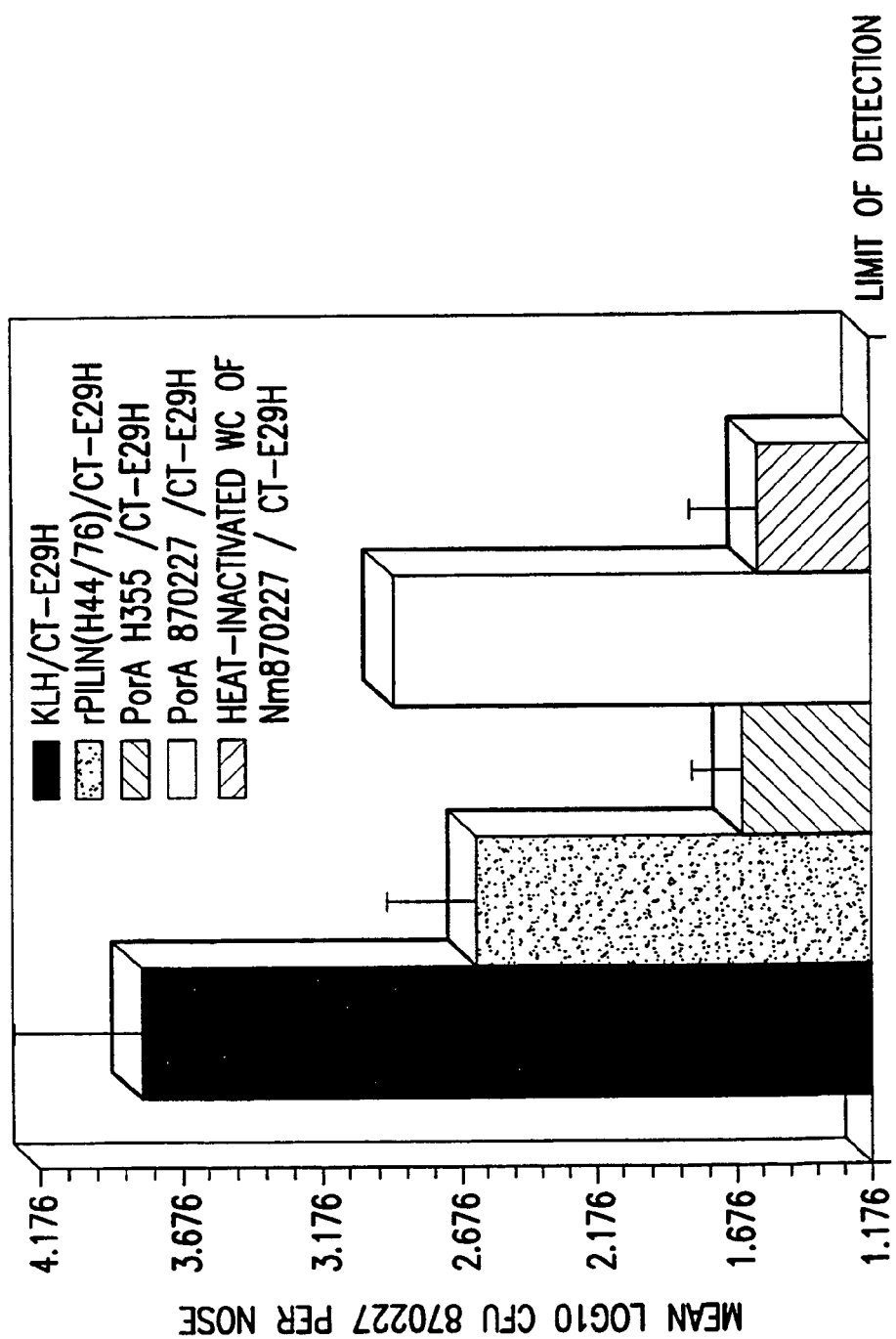
FIG. 4 depicts the reduction in nasal colonization in mean $Log_{10}$ cfu of meningococcal strain 870227 per nose in mice immunized intranasally (n=10 per group) with meningococcal rpilin, PorA from meningococcal strain H355, PorA from meningococcal strain 870227, heat-inactivated meningococcal strain 870227 whole cells or KLH, each adjuvanted with CT-$CRM_{E29H}$, where each group was then challenged with a heterologous meningococcal bacterial strain (870227).

In a fourth experiment, the ability of rpilin and PorA adjuvanted with CT-CRM$_{E29H}$ to protect mice against the challenge of a heterologous strain of meningococci was assessed. Ten Swiss-Webster mice per group were immunized IN (10 µl volume) with 5 µg of either rpilin, PorA from strain H355, or PorA from strain 870227, formulated with CT-CRM$_{E29H}$ (0.1 µg) at weeks 0, 2, and 3. Control groups were either heat-inactivated meningococcal strain 870227 whole cells or KLH (5 µg) plus CT-CRM$_{E29H}$ (0.1 µg). The endpoint IgG and IgA titers were determined by whole cell and antigen-specific ELISA on pooled serum samples collected at week 4 before challenge with the 870227 strain. The results are presented in Tables 20 and 21. The bacterial recovery from nasal tissue was determined by quantitative culture 24 hours after challenge with strain 870227 and was expressed as Log$_{10}$ CFU±standard deviation. The results are shown in FIG. 4.

Figure 5:
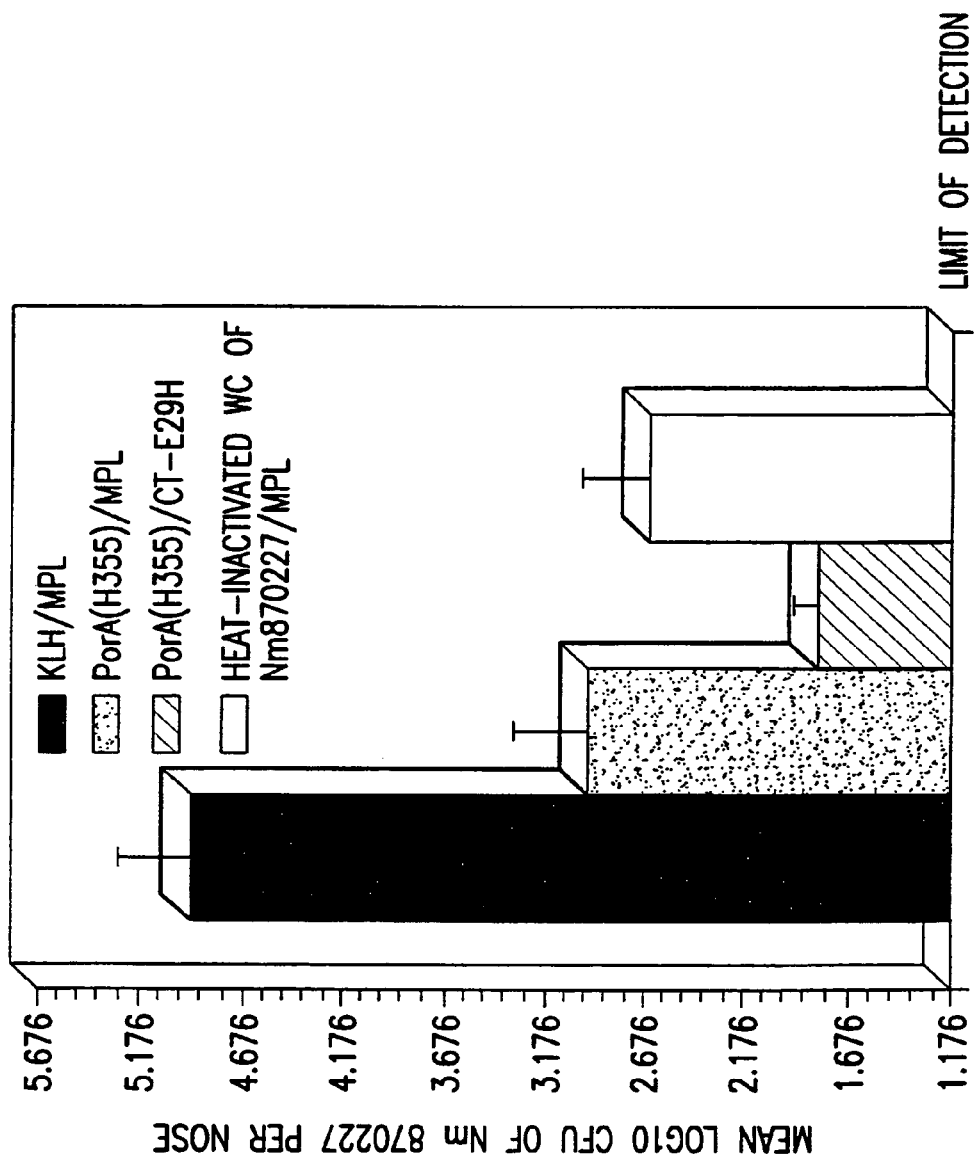
FIG. 5 depicts the reduction in nasal colonization in mean $Log_{10}$ cfu of meningococcal strain 870227 per nose in mice immunized subcutaneously (n=10 per group) with PorA from meningococcal strain H355 with CT-$CRM_{E29H}$ or MPL™ adjuvant, KLH with MPL™ adjuvant, or heat-inactivated meningococcal strain 870227 whole cells with MPL™ adjuvant, where each group was then challenged with a heterologous meningococcal bacterial strain (870227).

A fifth experiment was conducted to examine the potential of CT-CRM$_{E29H}$ as an adjuvant for parenteral immunization. Groups of 10 female Swiss-Webster mice, 5-6 weeks old, were immunized subcutaneously with 5 µg of PorA H355 formulated with either CT-CRM$_{E29H}$ (10 µg) or MPL™ (100 µg) at weeks 0 and 4. Control groups were immunized subcutaneously with heat-inactivated meningococcal 870227 whole cells or KLH (5 µg) plus MPL™ (100 µg). Mice were challenged IN with 1.2×10⁷ CFUs of meningococcal strain 870227 at week 6. Twenty-four hours post-challenge, mice were sacrificed and nasal tissues were homogenized and plated on selective medium. Colonies were counted after incubation at 37° C. overnight and expressed as Log$_{10}$ CFU±standard deviation. The results of this experiment are presented in Table 22 and FIG. 5.

TABLE 16

Adjuvant effects of CT-CRM$_{E29H}$ on the systemic and mucosal immune responses to N. meningitidis rPilin (Class I H44/76) in Swiss-Webster mice

| | Anti-rpilin antibody ELISA titers on pooled samples | | | | | | | | | |
|---|---|---|---|---|---|---|---|---|---|---|
| | Sera (wk 0) | | Sera (wk 4) | | EW | | NW | | VW | |
| Immunogen | IgA | IgG | IgA | IgG | IgA | IgG | IgA | IgG | IgA | IgG |
| rPilin | <50 | <50 | 878 | 69,013 | 4 | 41 | 23 | 2 | 37 | 17 |
| rPilin + | <50 | <50 | 2,209 | 209,228 | <2 | 19 | 34 | 40 | 61 | 51 |

TABLE 16-continued

Adjuvant effects of CT-CRM$_{E29H}$ on the systemic and mucosal immune responses to N. meningitidis rPilin (Class I H44/76) in Swiss-Webster mice Anti-rpilin antibody ELISA titers on pooled samples

| Immunogen | Sera (wk 0) IgA | Sera (wk 0) IgG | Sera (wk 4) IgA | Sera (wk 4) IgG | EW IgA | EW IgG | NW IgA | NW IgG | VW IgA | VW IgG |
|---|---|---|---|---|---|---|---|---|---|---|
| CT-CRM$_{E29H}$ (0.1 µg) rPilin + CT-CRM$_{E29H}$ (1 µg) | <50 | <50 | 4,089 | 1,344,776 | 41 | 540 | 75 | 45 | 135 | 216 |

TABLE 17

The effect of CT-CRM$_{E29H}$ on the immune response to meningococcal antigens in Swiss-Webster mice Total Sera IgG of Meningococcal B Whole Cell ELISA

| Group | H355P* strain Wk 0 | H355P* strain Wk 4 | FAM 18 strain Wk 0 | FAM 18 strain Wk 4 | M982 strain Wk 0 | M982 strain Wk 4 |
|---|---|---|---|---|---|---|
| 5 µg rPilin | 175* | 2,371 | 294* | 639 | 137* | 2,375 |
| 5 µg rpilin + 0.1 µg CT-CRM$_{E29H}$ | 175* | 24,965 | 294* | 2,702 | 137* | 21,862 |
| 5 µg PorA + 0.1 µg CT-CRM$_{E29H}$ | 175* | 10,156 | 294* | 9,136 | 137* | 5,733 |
| 5 µg KLH + 0.1 µg CT-CRM$_{E29H}$ | 175* | 192 | 294* | 230 | 137* | 100 |

*represent week 0 pooled samples from all groups

TABLE 18

The effect of CT-CRM$_{E29H}$ on the immune response to meningococcal antigens in Swiss-Webster mice Anti-rPilin and anti-PorA antibody ELISA titers on pooled samples

| Group | rPilin Sera IgG Wk 4 | rPilin Sera IgA Wk 4 | Class I OMP H355 Sera IgG Wk 4 | Class I OMP H355 Sera IgA Wk 4 |
|---|---|---|---|---|
| 5 µg rpilin | 8,840 | <50 | <50 | <50 |
| 5 µg rPilin + 0.1 µg CT-CRM$_{E29H}$ | 149,221 | 860 | 120 | <50 |
| 5 µg PorA H355 + 0.1 µg CT-CRM$_{E29H}$ | <50 | <50 | 13,795 | 60 |
| 5 µg KLH + 0.1 µg CT-CRM$_{E29H}$ | <50 | <50 | <50 | <50 |

TABLE 19

Immune responses of Swiss-Webster mice immunized intranasally with meningococcal PorA and CT-CRM$_{E29H}$
Anti-PorA H44/76 Antibody Titers

| Group | | Sera IgG | Sera IgA | EW IgG | EW IgA | NW IgG | NW IgA | VW IgG | VW IgA |
|---|---|---|---|---|---|---|---|---|---|
| 20 µg PorA | WCE | 3,530 | ND | ND | ND | ND | ND | ND | ND |
| | PorA | 1,220 | <50 | <2 | <2 | <2 | <2 | <7 | <7 |
| 20 µg PorA + 1 µg CT-CRM$_{E29H}$ | WCE | 26,660 | ND | ND | ND | ND | ND | ND | ND |
| | PorA | 17,673 | <50 | 5 | <2 | <2 | <2 | <7 | <7 |

ND = No data
WCE = whole cell ELISA to H44/76 strain
PorA = PorA H44/76 specific ELISA.

TABLE 20

Immune responses of Swiss-Webster mice immunized intranasally with heterologous and homologous meningococcal PorA and rPilin with CT-CRM$_{E29H}$ IgG titer# by ELISA in mice immunized with

| Assay Antigen | Serum at week | 5 µg KLH + 0.1 µg CT-CRM$_{E29H}$ | 5 µg PorA 5 µg rPilin + 0.1 µg CT-CRM$_{E29H}$ | 5 µg PorA H355 + 0.1 µg CT-CRM$_{E29H}$ | 5 µg PorA 870227 + 0.1 µg CT-CRM$_{E29H}$ | 25 µg HI WC 870227 + 0.1 µg CT-CRM$_{E29H}$ |
|---|---|---|---|---|---|---|
| WC | 0 | <100 | <100 | <100 | <100 | <100 |
| 870227 | 4 | 350 | 13,376 | 7,088 | 24,815 | 74,930 |
| WC | 0 | 257 | 257 | 257 | 257 | 257 |
| H355P | 4 | 310 | 3,687 | 5,140 | 3,930 | 5,933 |
| rPilin | 0 | 146 | 146 | 146 | 146 | 146 |
|  | 4 | 585 | 1,999,530 | <100 | <100 | <100 |
| PorA | 0 | <100 | <100 | <100 | <100 | <100 |
| H355 | 4 | <100 | 673 | 29,770 | 19,009 | 463 |
| PorA | 0 | <100 | <100 | <100 | <100 | <100 |
| 870227 | 4 | <100 | <100 | 10,020 | 23,045 | 5,935 |

Week 0 titers are pools from all groups.
WC = Whole Cell
HI = Heat-inactivated

TABLE 21

Immune responses of Swiss-Webster mice immunized intranasally with heterologous and homologous meningococcal PorA and rPilin with CT-CRM$_{E29H}$ IgA titer# by ELISA in mice immunized with

| Assay Antigen | Serum at week | 5 µg KLH + 0.1 µg CT-CRM$_{E29H}$ | 5 µg PorA 5 µg rPilin + 0.1 µg CT-CRM$_{E29H}$ | 5 µg PorA H355 + 0.1 µg CT-CRM$_{E29H}$ | 5 µg ParA 870227 + 0.1 µg CT-CRM$_{E29H}$ | 25 µg HI WC 870227 + 0.1 µg CT-CRM$_{E29H}$ |
|---|---|---|---|---|---|---|
| WC | 0 | <25 | <25 | <25 | <25 | <25 |
| 870227 | 4 | <25 | <25 | <25 | <25 | ND |
| WC | 0 | <25 | <25 | <25 | <25 | <25 |
| H355P | 4 | <25 | <25 | <25 | <25 | <25 |
| rPilin | 0 | <25 | <25 | <25 | <25 | <25 |
|  | 4 | <25 | 5,097 | <25 | <25 | <25 |
| PorA | 0 | <25 | <25 | <25 | <25 | <25 |
| H355 | 4 | <25 | <25 | 233 | 200 | <25 |
| PorA | 0 | <25 | <25 | <25 | <25 | <25 |
| 870227 | 4 | <25 | <25 | <25 | <25 | <25 |

Week 0 titers are pools from all groups.
WC = Whole Cell
HI = Heat-inactivated
ND = No data

TABLE 22

N. meningitidis Bactericidal Activity from mouse sera subcutaneously immunized with PorA with CT-CRM$_{E29H}$ or MPL ™

| Mouse sera | H355 p+ | 870227 |
|---|---|---|
| wk5, d6 KLH (5 µg), MPL ™ (100 µg) | <25 | <25 |
| wk5, d6 H355 class 1 OMP (5 µg), MPL ™ (100 µg) | 200 | <25 |
| wk5, d6 870227 class 1 OMP (5 µg), MPL ™ (100 µg) | <25 | 100 |
| wk5, d6 heat-inactivated 870227 WC (25 µg), MPL ™ (100 µg) | 25 | 200 |
| wk5, d6 H355 class 1 OMP (5 µg), CT-CRM$_{E29H}$ (10 µg) | <25 | <25 |
| wk0 pool negative control | <10 | <10 |
| wk6 positive control 1 | 200 | nd |

TABLE 22-continued

*N. meningitidis* Bactericidal Activity from mouse sera subcutaneously immunized with PorA with CT-CRM$_{E29H}$ or MPL™

| Mouse sera | H355 p+ | 870227 |
|---|---|---|
| wk6 positive control 2 | nd* | 400 |

*nd = not done
Complement used: Human UR4-97

Example 10

The Immune Responses of BALB/c Mice Immunized with the Purified Native Fusion (F) Glycoprotein of Respiratory Syncytial Virus (RSV)

In a first experiment, 6-8 week old BALB/c mice (5 mice/group) were immunized intranasally (10 µl) at weeks 0 and 14 with 3 µg of purified native protein formulated with CT-CRM$_{E29H}$ (1 µg or 10 µg/mouse), wild-type CT (1 µg/mouse), CT-B (1 µg or 10 µg/mouse) or no adjuvant. Endpoint IgG and IgA antibody titers were assayed, by ELISA, on day 24 of the experiment. Titers were obtained from sera, bronchoalveolar lavage and vaginal washes. The results are presented in Table 23.

In a second experiment, 6-8 week old BALB/c mice (5 mice/group) were pre-immunized intranasally (50 µl) with either wild-type CT (1 µg/mouse) or CT-CRM$_{E29H}$ (1 µg/mouse) on days 0 and 14. Control groups were not pre-immunized. Thereafter, on days 28 and 42, all mice were immunized intranasally with 3 µg of F protein formulated with the same amounts of CT or CT-CRM$_{E29H}$. The endpoint antibody titers were determined by ELISA on pooled samples collected on days 56 (sera) and 57 (bronchoalveolar and vaginal wash fluids). The results are presented in Table 24.

In a third experiment, naive female BALB/c mice (6-8 weeks, 5 mice/group) were immunized intranasally (IN) at weeks 0, 1 and 2 with purified native fusion (F) protein from RSV A2. Immunizations were prepared by formulating F protein (3 µg/mouse) with CT-CRM$_{E29H}$ (1 µg or 10 µg/mouse), CT-B (1 µg or 10 µg/mouse) or alum (100 µg/mouse). The vaccine was administered intranasally by allowing anaesthetized mice to breathe in the vaccine placed at the tip of the nostril. Total volume per dose was 10 µl per mouse (in Table 25), at weeks 0, 1 and 2. Control mice received intramuscular primary immunization containing F/AlOH, or received primary and secondary immunizations of live RSV A2, delivered intranasally. Systemic humoral immune responses were assayed, by ELISA, nine days (for Tables 25 and 26) post-tertiary immunization. Bronchoalveolar lavage, vaginal and nasal washes were also collected and utilized in the characterization of mucosal antibody responses. Spleens from immunized mice were used to assay antigen-dependent killer cell activity against MHC-compatable RSV-infected target cells. A second cohort of mice, that had received an identical immunization schedule, was challenged with live RSV. Protection of lung compartments within this cohort was subsequently analyzed at four days post-challenge by determination of virus plaques in collected homogenized lung tissue. Statistical analyses were performed using ANOVA. The results are presented in Tables 25 and 26.

In a fourth experiment, BALB/c mice were immunized intranasally at weeks 0, 1 and 2 with purified RSV F protein (3 µg/mouse) in combination with CT-CRM$_{E29H}$ (1 µg or 10 µg/mouse), CTB (1 µg or 10 µg/mouse) or PBS. As a control, mice also received intranasal delivery of RSV or intramuscular delivery of F/AlOH. Splenocytes were isolated nine days post-final immunization and stimulated in vitro with syngeneic RSV-infected stimulator cells. After six days in culture, antigen-dependent killer cell activity was determined by quantitation of $^{51}$Chromium release by RSV-infected target cells. The results are presented in FIG. 6.

In a fifth experiment, a viral protection assay, the lung compartments of immunized mice were isolated four days after challenge with live RSV, homogenized, and quantitation of infectious virus was performed. BALB/c mice were immunized intranasally with vaccines containing purified F protein from RSV and either CT-CRM$_{E29H}$, CTB or PBS. Groups of mice were also immunized intramuscularly with F/AlOH as a control. Eight days after final immunization (three weeks post F/AlOH vaccine), mice were challenged with live RSV. Four days later, pulmonary tissues were harvested and utilized in the quantitation of infectious virus. The results are presented in FIG. 7.

In a sixth experiment, naive female BALB/c mice (6-8 weeks, 5 mice/group) were immunized intranasally (IN) at weeks 0, 1 and 2 with purified native fusion (F) protein from RSV A2. Immunizations were prepared by formulating F protein (3 µg/mouse) with CT-CRM$_{E29H}$ (1 µg/mouse) or alum (100 µg/mouse). The vaccine was administered intranasally by allowing anaesthetized mice to breathe in the vaccine placed at the tip of the nostril. Total volume per dose was 5 µl per mouse (in Table 27), at weeks 0, 1 and 2. Control mice received intramuscular primary immunization containing F/AlOH, or received primary and secondary immunizations of live RSV A2, delivered intranasally. Systemic humoral immune responses were assayed, by ELISA, two weeks (for Tables 27 and 28) post-tertiary immunization. Bronchoalveolar lavage, vaginal and nasal washes were also collected and utilized in the characterization of mucosal antibody responses. Spleens from immunized mice were used to assay antigen-dependent killer cell activity against MHC-compatable RSV-infected target cells. A second cohort of mice, that had received an identical immunization schedule, was challenged with live RSV. Protection of lung compartments within this cohort was subsequently analyzed at four days post-challenge by determination of virus plaques in collected homogenized lung tissue. Statistical analyses were performed using ANOVA. Results are presented in Tables 27 and 28.

In a seventh experiment, the protocol from the fourth experiment was again utilized to determine the antigen-dependent CTL activity to RSV-infected target cells. The results are presented in FIG. 8.

In an eighth experiment, another viral protection assay, BALB/c mice (5 mice/group) were immunized intranasally with formulations containing purified RSV F protein, with or without CT-CRM$_{E29H}$. Groups of mice were also immunized intramuscularly with F/AlOH and left unimmunized (naïve) as a control. Two weeks after final immunization (four weeks post-F/AlOH administration), all groups were challenged with live RSV. Four days later, pulmonary tissues were harvested and utilized in the quantitation of infectious virus. The results are presented in FIG. 9.

In a ninth experiment, a three dose protocol was employed to investigate the adjuvant response of CT-CRM$_{E29H}$ in more detail. Groups of five BALB/c mice were immunized IN (5 µl) at weeks 0, 1 and 2 with F protein (3 µg), admixed with either 0.01, 0.1 or 1.0 µg CT-CRM$_{E29H}$. Control mice were primed at day 0 with F/AlOH (intramuscular) or RSV A2 (IN). Serum antibody titers were determined two weeks post-tertiary immunization. The results are presented in Table 29. Data are presented as the log$_{10}$ geometric mean antibody titer (±1 SD). Similar results were obtained in two separate studies.

After IN immunization with F/CT-CRM$_{E29H}$, the mice in the ninth experiment were also tested for their local antibody responses to F protein. Mucosal wash samples were taken from mice sacrificed two weeks post-tertiary immunization and analyzed for anti-F protein-specific IgG and IgA by ELISA. The results are presented in Table 30. Data are presented as the log$_{10}$ of the geometric mean endpoint titer that resulted in an OD$_{410}$ of 0.03. Similar results were obtained in two separate studies.

In a tenth experiment, in order to investigate the functional capacity of the humoral immune responses induced by F/CT-CRM$_{E29H}$ immunization, sera were tested in a plaque reduction assay for neutralizing antibody titers to RSV A2. The results are presented in Table 31. Geometric mean neutralizing antibody titers (log$_{10}$) were determined on individual sera (five mice per group) in the presence (+C') and absence (–C') of 5% guinea pig serum as a complement source. Similar results were obtained in two separate studies.

In an eleventh experiment, mice (five mice per group) received IN immunizations of F protein formulated with 0.01, 0.1 or 1 µg of CT-CRM$_{E29H}$ on days 0, 7 and 14. Control mice were immunized with F/AlOH (intramuscular) or RSV A2 (IN). Immunized mice were challenged two weeks after tertiary immunization, in order to determine the ability of F/CT-CRM$_{E29H}$ to protect against subsequent infection. Four days post-infection, virus levels were determined in homogenized lung and nose tissues of individual mice. The results are presented in Table 32. Data are presented as the geometric mean virus titer per g of tissue (±1 standard deviation).

TABLE 23

The generation of anti-cholera toxin antibodies in BALB/c mice after intranasal immunization with either CT, CT-B, or CT-CRM$_{E29H}$
Anti-Cholera Toxin Antibody Titers[a]

| Adjuvant[b] | Sera | | BAW | | VW | |
|---|---|---|---|---|---|---|
| | IgG | IgA | IgG | IgA | IgG | IgA |
| None | <100 | <100 | <25 | <25 | <25 | <25 |
| CT (1 µg) | 434,180 | 3,944 | 70 | <25 | 214 | 1,431 |
| CT-B (1 µg) | 781,628 | 4,665 | 280 | <25 | 127 | 709 |
| CT-B (10 µg) | 156,239 | 2,544 | 241 | <25 | 163 | 1,243 |
| E29H (1 µg) | 118,541 | 2,207 | 94 | <25 | 227 | 1,578 |
| E29H (10 µg) | 514,233 | 4,881 | 410 | ND[c] | 214 | 980 |

[a]The endpoint antibody titers were determined on pooled samples collected on day 24 of the study. BAW and VW denote bronchoalveolar and vaginal wash respectively. There were 5 mice per group.
[b]The mice were immunized intranasally (10 µl) on days 0 and 14 with 3 µg of native F protein admixed with the indicated amount of either wild-type CT, commercial CT-B, or CT-CRM$_{E29H}$.
[c]ND = No data

TABLE 24

The effect of pre-existing anti-cholera toxin antibodies on the immunogenicity of the fusion protein of respiratory syncytial virus formulated with either CT or CT-CRM$_{E29H}$
Anti-Fusion Protein Antibody Titers[a]

| Pre-Vax[b] | Adjuvant | Sera | | BAW | | VW | |
|---|---|---|---|---|---|---|---|
| | | IgG | IgA | IgG | IgA | IgG | IgA |
| Non | None | <1,000 | <100 | <25 | <25 | <25 | 25 |
| None | CT | 887,136 | 11,337 | 16,219 | 8,709 | 274 | 1,447 |
| + | CT | >10,000,000 | 22,344 | 253,641 | 24,331 | 36,415 | 4,391 |
| None | E29H | 1,430,836 | 10,786 | 2,232 | 1,680 | 333 | 378 |
| + | E29H | 6,346,730 | 17,890 | 131,217 | 12,367 | 2,750 | 6,359 |

[a]The endpoint antibody titers were determined by ELISA on pooled samples collected on days 56 (sera) and 57 (bronchoalveolar (BAW) and vaginal (VW) wash fluids). There were 5 mice per group
[b]The mice were pre-immunized (intranasally, 50 µl) with either wild-type CT (1 µg) or CT-CRM$_{E29H}$ (1 µg) on days 0 and 14. Thereafter on days 28 and 42 all mice were immunized (intranasally, 50 µl) with 3 µg of F protein formulated with same amounts (1 µg) of either wild-type CT or CT-CRM$_{E29H}$. The endpoint anti-CT antibody titers of mice pre-immunized with either wild-type CT or CT-CRM$_{E29H}$ and subsequently immunized with F protein were greater than 1,000,00 on day 42.

TABLE 25

Systemic Immune Responses of BALB/c mice immunized intranasally with RSV F protein and CT-CRM$_{E29H}$

| | | Anti-F Antibody Titers | | | |
|---|---|---|---|---|---|
| Group | Immunogen | IgG | IgG1 | IgG2a | IgA |
| 776 | 10 µg E29H | <100 | <100 | <100 | <100 |
| 777 | 3 µg F<br>1 µg E29H | 126,463<br>+/-<br>32,646 | 62,344<br>+/-<br>27,002 | 4,899<br>+/-<br>1,027 | 16,202<br>+/-<br>2,031 |
| 778 | 3 µg F<br>10 µg E29H | 209,123<br>+/-<br>75,688 | 75,711<br>+/-<br>29,659 | 19,425<br>+/-<br>13,508 | 15,706<br>+/-<br>10,909 |
| 779 | 3 µg F<br>1 µg CTB | 46,742<br>+/-<br>32,987 | 26,902<br>+/-<br>14,985 | 4,239<br>+/-<br>3,658 | 4,076<br>+/-<br>614 |
| 780 | 3 µg F<br>10 µg CTB | 285,116<br>+/-<br>110,154 | 116,245<br>+/-<br>34,596 | 10,512<br>+/-<br>11,016 | 11,679<br>+/-<br>7,246 |
| 784 | 3 µg F<br>PBS | 2,171<br>+/-<br>1,921 | 521<br>+/-<br>743 | <100 | <100 |
| 785 | 3 µg F<br>100 µg AlOH | 23,303<br>+/-<br>16,994 | 5,519<br>+/-<br>2,348 | <1000 | <100 |
| 907 | RSV A2 | 52,749<br>+/-<br>23,557 | 6,252<br>+/-<br>4,286 | 8,718<br>+/-<br>2,826 | 4,284<br>+/-<br>2,350 |

For total IgG:
p < 0.05: 777 to 780 versus 784; 780 vs 779; 777 to 780 vs 785; 777, 778, 780 vs 907 (779 vs 907 p = 0.7) p > 0.05: 778 vs 777 (p = 0.125);
For IgG1:
p < 0.05: 777 to 780 vs 784; 777 to 780 vs 907; 777 to 780 vs 785
p > 0.05: 781 to 780 vs 907
For IgG2a
p < 0.05: 777 to 780 vs 784

TABLE 26

Mucosal Immune Responses of BALB/c mice immunized intranasally with RSV F protein and CT-CRM$_{E29H}$

| | | Anti-F Antibody Titers | | | | | |
|---|---|---|---|---|---|---|---|
| | | BAL pools | | VW pools | | NW pools | |
| Group | Immunogen | IgG | IgA | IgG | IgA | IgG | IgA |
| 776 | 10 µg E29H | <25 | <25 | <25 | <25 | <25 | <25 |
| 777 | 3 µg F + 1 µg E29H | 463 | <25 | 253 | 2855 | <25 | 237 |
| 778 | 3 µg F + 10 µg E29H | 370 | <25 | 239 | 848 | 491 | 242 |
| 779 | 3µg F + 1 µg CTB | 137 | <25 | 298 | 426 | 77 | 272 |
| 780 | 3 µg F + 10 µg CTB | 1109 | 226 | 903 | 3574 | 512 | 372 |
| 784 | 3 µg F PBS | <25 | <25 | <25 | 78 | <25 | <25 |
| 785 | 3 µg F + 100 µg AlOH | <25 | <25 | <25 | <25 | <25 | <25 |
| 907 | RSV A2 | 2870 | 1126 | 167 | 738 | 172 | 170 |

TABLE 27

Systemic Immune Responses of BALB/c mice immunized intranasally with RSV F protein and CT-CRM$_{E29H}$

| | | Anti-F Antibody Titers | | | |
|---|---|---|---|---|---|
| Group | Immunogen | IgG | IgG1 | IgG2a | IgA |
| 250 | 3 µg F PBS | <100 | <100 | <100 | <100 |
| 256 | 3 µg F<br>1 µg E29H | 315,878<br>+/-<br>131,746 | 78,380<br>+/-<br>40,870 | 10,718<br>+/-<br>16,475 | 444<br>+/-<br>1,458 |
| 257 | 1 µg E29H | <100 | <100 | <100 | <100 |
| 258 | 3 µg F<br>100 µg AlOH | 121,551<br>+/-<br>52,023 | 63,595<br>+/-<br>27,491 | 428<br>+/-<br>4,205 | <100 |
| 259 | RSV A2 | 112,451<br>+/-<br>50,247 | 8,871<br>+/-<br>5,206 | 9,953<br>+/-<br>4,924 | 224<br>+/-<br>344 |

For total IgG:
p<0.05: 256 vs 250 and 257
p>0.05: 256 vs 258 and 259
For IgG1:
p<0.05: 256 vs 250 and 257
p>0.05: 256 vs 258
For IgG2a
p<0.05: 256 vs 250, 257 and 258
p>0.05: 256 vs 259
For IgGA
p>0.05: 256 vs 259

TABLE 28

Mucosal Immune Responses of BALB/c mice immunized intranasally with RSV F protein and CT-CRM$_{E29H}$

| | | Anti-F Antibody Titers | | | | | |
|---|---|---|---|---|---|---|---|
| | | BAL pools | | VW pools | | NW pools | |
| Group | Immunogen | IgG | IgA | IgG | IgA | IgG | IgA |
| 250 | 3 µg F PBS | <25 | <25 | <25 | <25 | <25 | <25 |
| 256 | 3 µg F 1 µg E29H | 826 | <25 | 1,195 | 3,730 | 554 | 875 |
| 257 | 1 µg E29H | <25 | <25 | <25 | <25 | <25 | <25 |
| 258 | 3 µg F 100 µg AlOH | 706 | <25 | 577 | 108 | 148 | <25 |
| 259 | RSV A2 | 347 | <25 | 172 | 1,449 | 305 | <25 |

TABLE 29

Anti-F Protein Serum Antibody Response Induced After
Immunization with F Protein and CT-CRM$_{E29H}$

| | Geometric mean antibody titers (log$_{10}$) | | | | | | |
|---|---|---|---|---|---|---|---|
| | Anti-F protein | | | | | Anti-CT | |
| Immunogen | IgG | IgG1 | IgG2a | IgG2b | IgA | IgG | IgA |
| F/PBS | 3.0 ± 1.0 | 2.9 ± 0.9 | 2.2 ± 0.4 | 2.4 ± 0.6 | <2.0 | <3.7 | <2.0 |
| CT-CRM$_{E29H}$ (1.0 µg) | <2.0 | <2.0 | <2.0 | <2.0 | <2.0 | 6.4 ± 0.3 | 4.4 ±0.1 |
| F/CT-CRM$_{E29H}$ (1.0 µg) | 5.6 ± 0.3[a,b] | 5.2 ± 0.3[a,b] | 4.5 ± 0.3[a,b] | 5.0 ± 0.3[a,b] | 3.0 ± 0.6[a,b] | 6.4 ± 0.2[d] | 4.3 ± 0.2[e] |
| F/CT-CRM$_{E29H}$ (0.1 µg) | 5.4 ± 0.2[a] | 5.1 ± 0.2[a] | 3.9 ± 0.7[a] | 4.6 ± 0.5[a] | 3.1 ± 0.2[a] | 5.5 ± 0.2[a] | 3.8 ± 0.2[d] |
| F/CT-CRM$_{E29H}$ (0.01 µg) | 3.8 ± 0.80[a] | 3.5 ± 0.9[a] | 2.3 ± 0.7[a] | 3.0 ± 0.7[a] | 2.1 ± 0.2[a] | <3.7 | <2.0 |
| F/AlOH | 4.9 ± 0.8 | 4.7 ± 0.7 | 3.5 ± 0.9 | 3.7 ± 1.0 | <2.0 | ND[g] | ND |
| RSV A2 | 4.9 ± 0.1 | 4.0 ± 0.2 | 4.4 ± 0.2 | 4.1 ± 0.3 | 2.3 ± 0.3[c] | ND | ND |

[a] $p < 0.05$ compared to F/PBS or F/CT-E29H (0.01 µg),
[b] $p > 0.05$ compared to F/CT-E29H (0.1 µg) or F/AlOH.
[c] $p < 0.05$ compared to F/CT-E29H (0.1 and 0.01 µg) and F/PBS. $p > 0.05$ compared to CT-E29H (1.0 µg).
[d] $p < 0.05$ compared to F/PBS and F/CT-E29H (0.01 µg).
[e] $p > 0.05$ compared to F/PBS.
[f] $p < 0.05$ compared to F/CT-E29H (0.1 or 1.0 µg).
[g] ND = not done.

TABLE 30

Anti-F Protein Antibodies in the Mucosal Fluids of Mice
Immunized with F Protein Formulated with CT-CRM$_{E29H}$

| | BAL | | VW | | NW | |
|---|---|---|---|---|---|---|
| Immunogen | IgG | IgA | IgG | IgA | IgG | IgA |
| F/PBS | <1.4 | <1.4 | <1.4 | <1.4 | <1.4 | <1.4 |
| CT-CRM$_{E29H}$ (1 µg) | <1.4 | <1.4 | <1.4 | <1.4 | <1.4 | <1.4 |
| F/CT-CRM$_{E29H}$ (1 µg) | 3.1 | <1.4 | 2.8 | 3.5 | 2.0 | 2.2 |
| F/CT-CRM$_{E29H}$ (0.1 µg) | 2.5 | <1.4 | 2.5 | 2.9 | <1.4 | 2.3 |
| F/CT-CRM$_{E29H}$ (0.01 µg) | <1.4 | <1.4 | <1.4 | 2.2 | <1.4 | <1.4 |
| F/AlOH | 2.4 | <1.4 | <1.4 | <1.4 | <1.4 | <1.4 |

TABLE 31

Generation of Systemic Anti-RSV Neutralizing
Antibodies After IN Immunization with
F Protein Formulated with CT-CRM$_{E29H}$

| Immunogen | Neutralizing antibody titer(+C') | Neutralizing antibody titer(−C') |
|---|---|---|
| F/PBS | <1.3 | <1.3 |
| CT-CRM$_{E29H}$ (1 µg) | <1.3 | <1.3 |
| F/CT-CRM$_{E29H}$ (1 µg) | 2.3 ± 0.7[a] | <1.3 |
| F/CT-CRM$_{E29H}$ (0.1 µg) | 2.2 ± 0.4[b] | <1.3 |
| F/CT-CRM$_{E29H}$ (0.01 µg) | <1.3 | <1.3 |
| F/AlOH | 2.0 ± 0.3 | <1.3 |
| RSV A2 | 2.3 ± 0.3 | <1.3 |

[a] $p < 0.05$ compared to F/PBS or F/CT-CRM$_{E29H}$ (0.01 µg), $p > 0.05$ compared to F/CT-CRM$_{E29H}$ (0.1 µg), F/AlOH or RSV A2.
[b] $p < 0.05$ compared to F/PBS or F/CT-CRM$_{E29H}$ (0.01 µg), $p > 0.05$ compared to F/CT-CRM$_{E29H}$ (1 µg), F/AlOH or RSV A2.

TABLE 32

Virus Infectivity of Lung and Nasal Tissue After
IN Immunization with F Protein and CT-CRM$_{E29H}$

| Immunogen | Lung virus titer (log$_{10}$ mean ± SD) | Nasal virus titer (log$_{10}$ mean ± SD) |
|---|---|---|
| F/PBS | 4.6 ± 0.5 | 2.7 ± 0.2 |
| CT-CRM$_{E29H}$ (1 µg) | 4.6 ± 0.5 | 3.5 ± 0.2 |
| F/CT-CRM$_{E29H}$ (1 µg) | <2.0 ± 0.1[a,b] | <1.9 ± 0.1[c] |
| F/CT-CRM$_{E29H}$ (0.1 µg) | <1.9 ± 0.1[a] | <1.8 ± 0.1[d] |
| F/CT-CRM$_{E29H}$ (0.01 µg) | 3.9 ± 0.7 | 2.9 ± 0.4 |
| F/AlOH | 2.6 ± 0.7 | 2.3 ± 0.4 |
| RSV | <2.0 ± 0.03 | <1.8 ± 0.1 |
| Naive | 4.6 ± 0.1 | 3.4 ± 0.5 |

[a] $p < 0.05$ compared to F/PBS, F/CT-CRM$_{E29H}$ (0.01 µg), CT-CRM$_{E29H}$ or naive, $p > 0.05$ compared to F/AlOH or RSV A2.
[b] $p > 0.05$ compared to F/CT-CRM$_{E29H}$ (0.1 µg).
[c] $p < 0.05$ compared to F/CT-CRM$_{E29H}$ (0.01 µg), F/PBS, CT-CRM$_{E29H}$ or naive, $p > 0.05$ compared to F/CT-CRM$_{E29H}$ (0.1 µg), F/AlOH or RSV A2.
[d] $p < 0.05$ compared to F/PBS, F/CT-CRM$_{E29H}$ (0.01 µg), CT-CRM$_{E29H}$ or naive, $p > 0.05$ compar d to F/CT-CRM$_{E29H}$ (1 µg), F/A1OH or RSV A2.

Example 11

The Immune Responses of Mice Immunized with
Rotavirus Recombinant Virus-Like Particles

*Spodoptera frugiperda* (Sf-9) cells (American Type Culture Collection, Manassas, Va.) were maintained in SF-900 II serum free medium (Gibco-BRL, Grand Island, N.Y.). Sf9 cells were co-infected with recombinant baculovirus constructs expressing VP2 and VP6 genes from Simian rotavirus strain SA11 (32).

Released 2/6-VLPs were purified from the growth medium of these infected Sf9 cells as follows. The cells were clarified by centrifugation at 830×g for 30 minutes at room temperature. The supernatants were then further clarified by centrifugation at 8000×g for 30 minutes. VLPs were purified from the supernatants by centrifugation twice through 35% sucrose in TNC buffer (10 mM Tris, 140 mM NaCl, 10 mM $CaCl_2$, pH 8.0) at 96500×g for two hours, then suspended in TNC buffer and stored at 4° C. Purified VLPs were analyzed by SDS-PAGE, followed by silver and Commassie brilliant blue staining to determine purity, Western blot analysis to analyze protein composition, electron microscopy to determine integrity of the particles, and BCA protein assay to measure total protein concentration.

Commassie brilliant blue, silver staining and Western blot analysis of purified 2/6-VLP confirmed the presence of VP2 and VP6 proteins, as well as their purity and immunoreactivity with specific monoclonal antibodies. Purity of VLPs was estimated to be about 95% from the band intensities on the gels. In addition, electron microscopic analysis of these purified 2/6-VLPs confirmed their morphological integrity (data not shown).

Figure 10A:
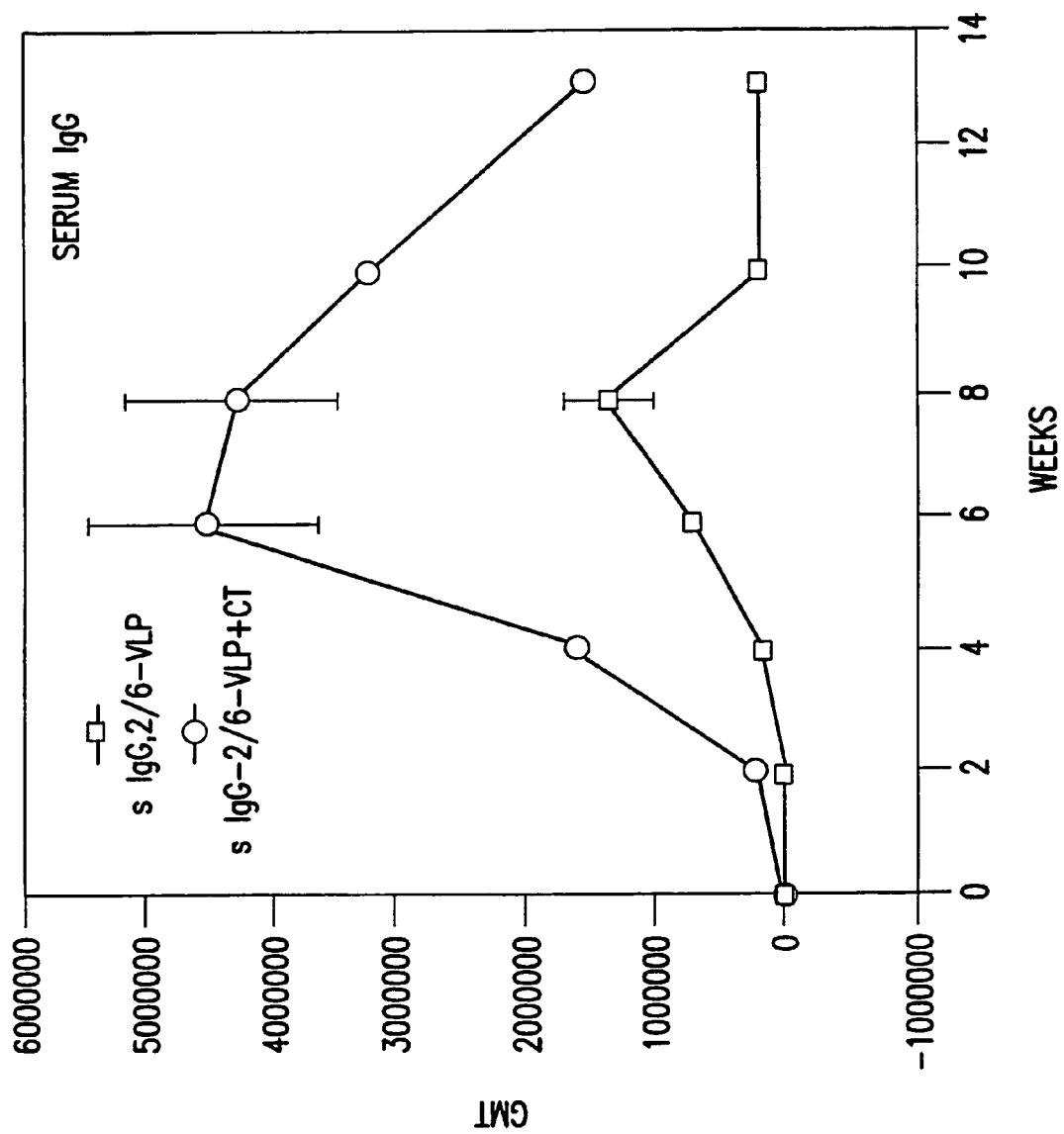
FIG. 10 depicts rotavirus-specific serum antibody responses in BALB/c mice immunized intranasally with 2/6-VLPs with or without CT-$CRM_{E29H}$ adjuvant. BALB/c mice were immunized intranasally with 2/6-VLPs with (n=4) or without (n=5) CT-$CRM_{E29H}$ and levels of rotavirus-specific IgG (FIG. 10A), IgM (FIG. 10B) and IgA (FIG. 10C) were measured. Standard deviations are shown.
Figure 10C:
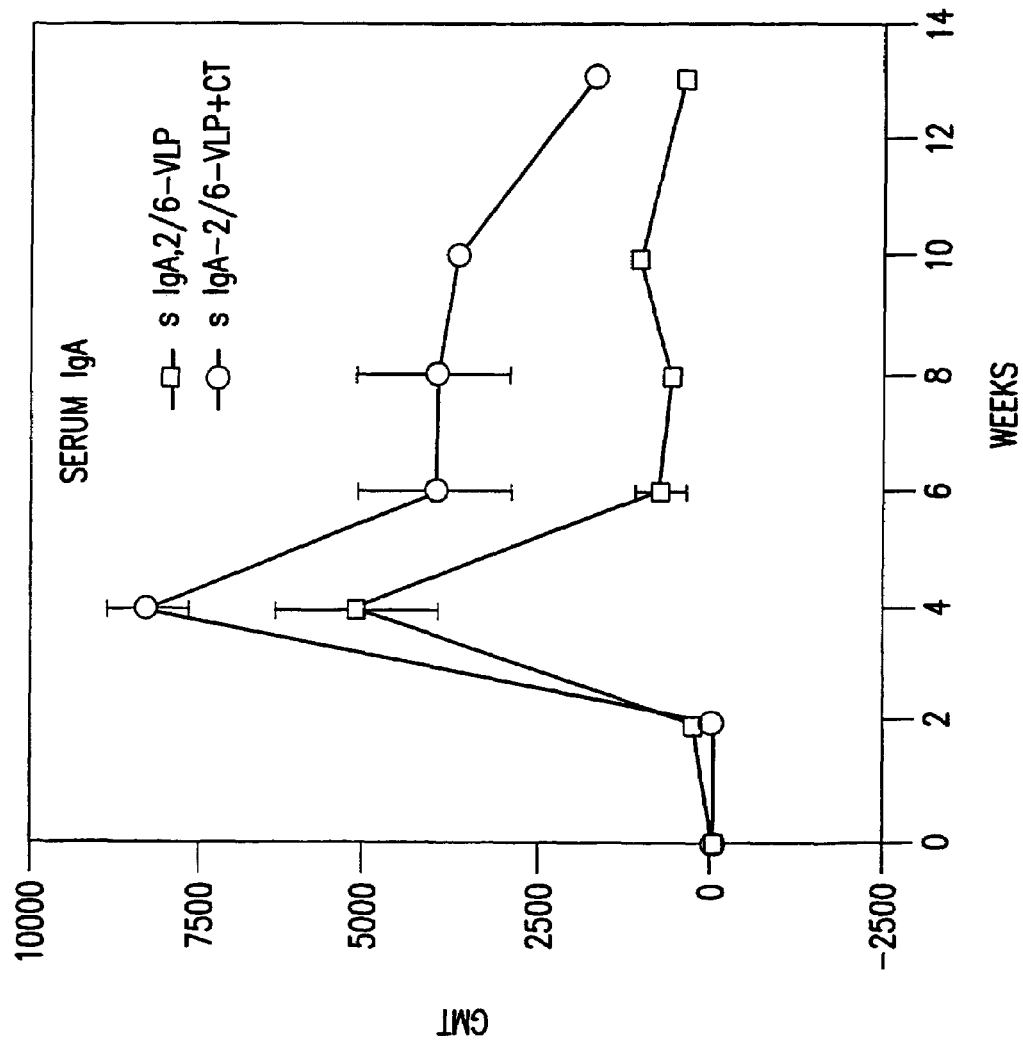
Figure 11A:
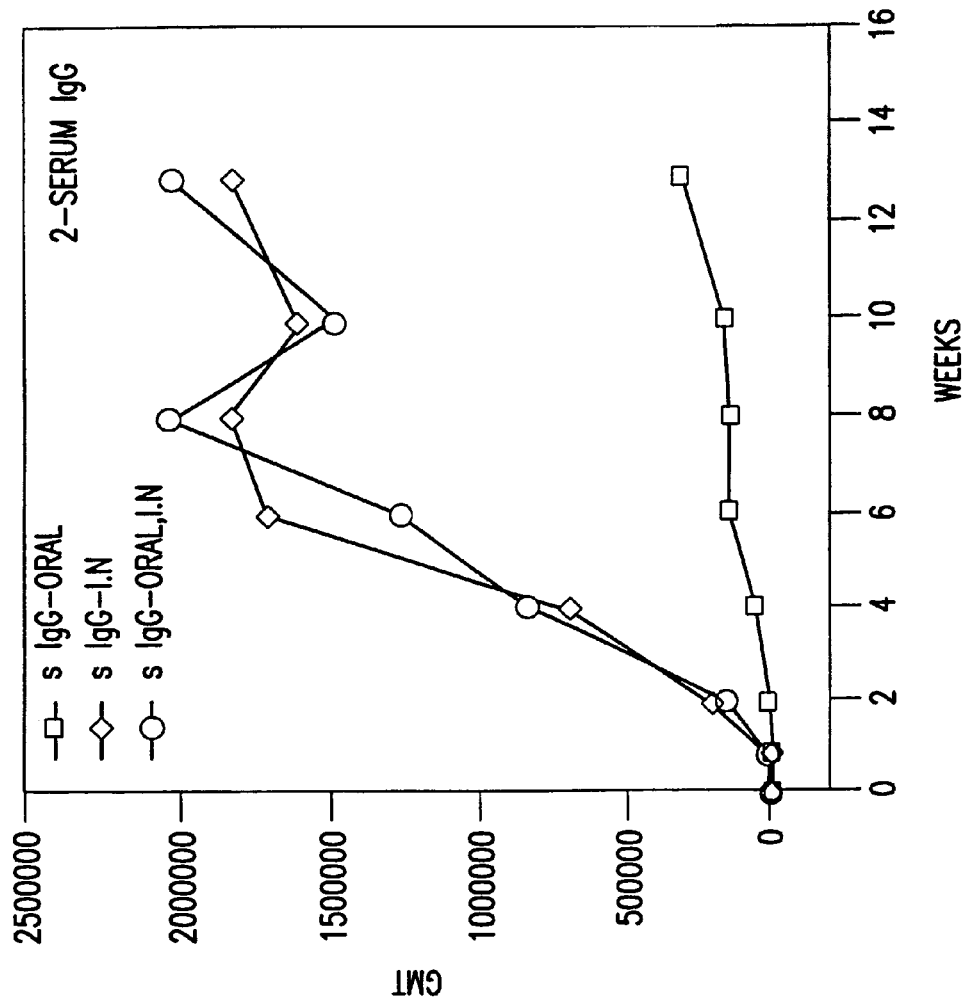
FIG. 11 depicts rotavirus-specific serum antibody responses in BALB/c inbred mice immunized with 2/6-VLPs. Groups of BALB/c mice were immunized, orally (square, n=4), intranasally (diamond, n=5) or in combination (intranasal plus oral, circle, n=4), with 2/6-VLPs plus CT-$CRM_{E29H}$ on week 0 and 2. Serum samples were collected from individual mice in each group on weeks shown, and levels of serum IgG (FIG. 11A), IgM (FIG. 11B) and IgA (FIG. 11C) were determined for each mouse by ELISA. Geometric mean titers (GMT) were calculated for each group and plotted against weeks post-immunization.
Figure 11B:
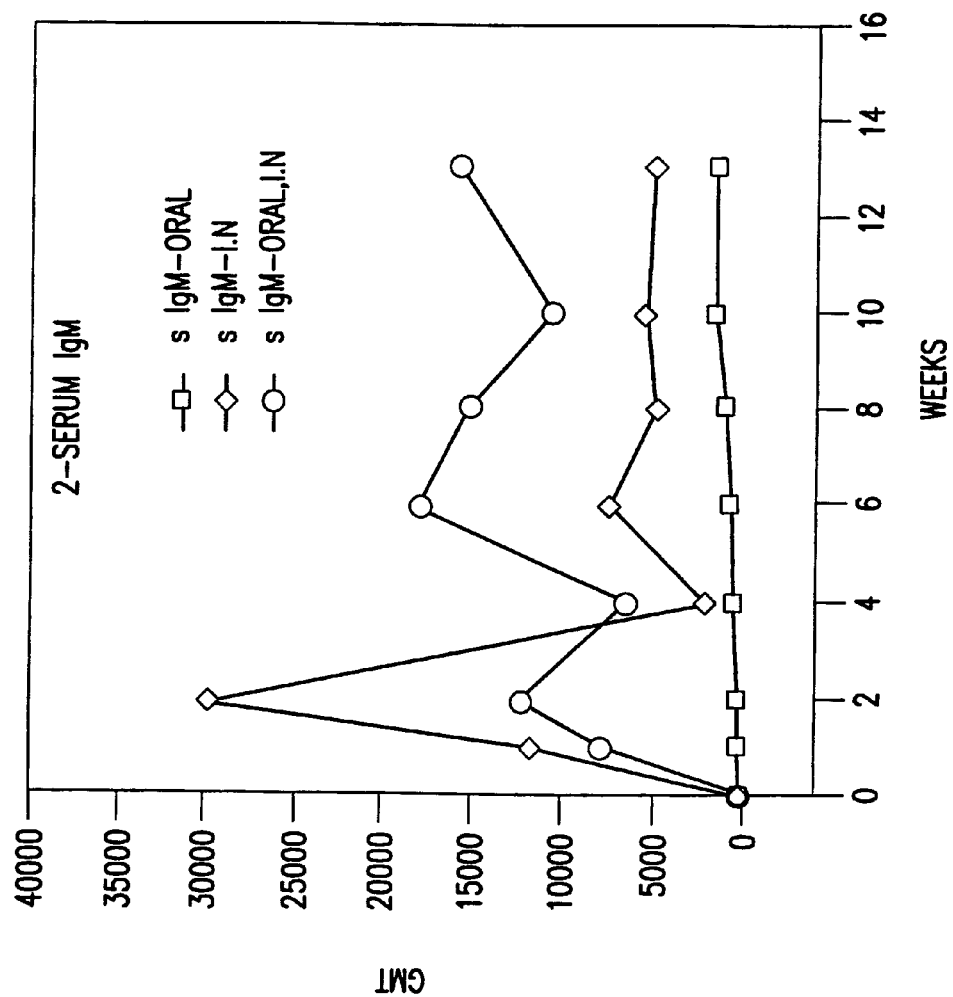
Figure 11C:
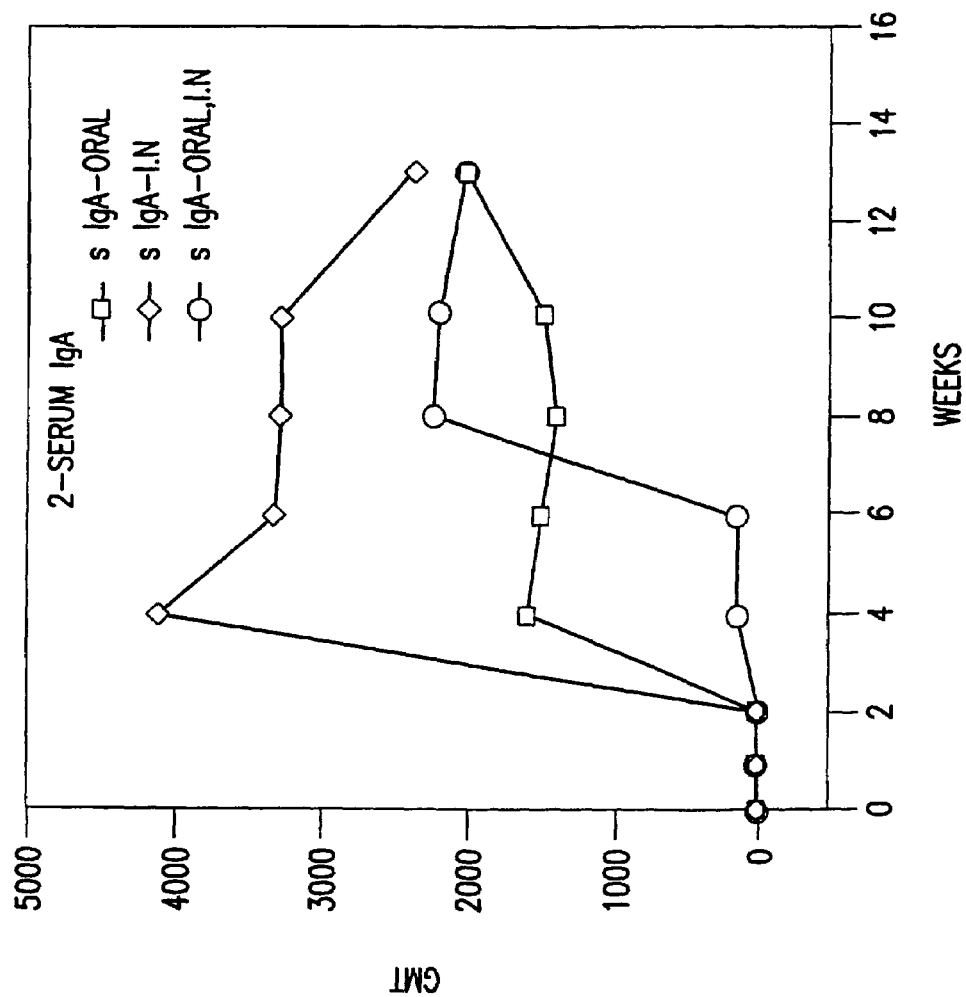
Figure 12:
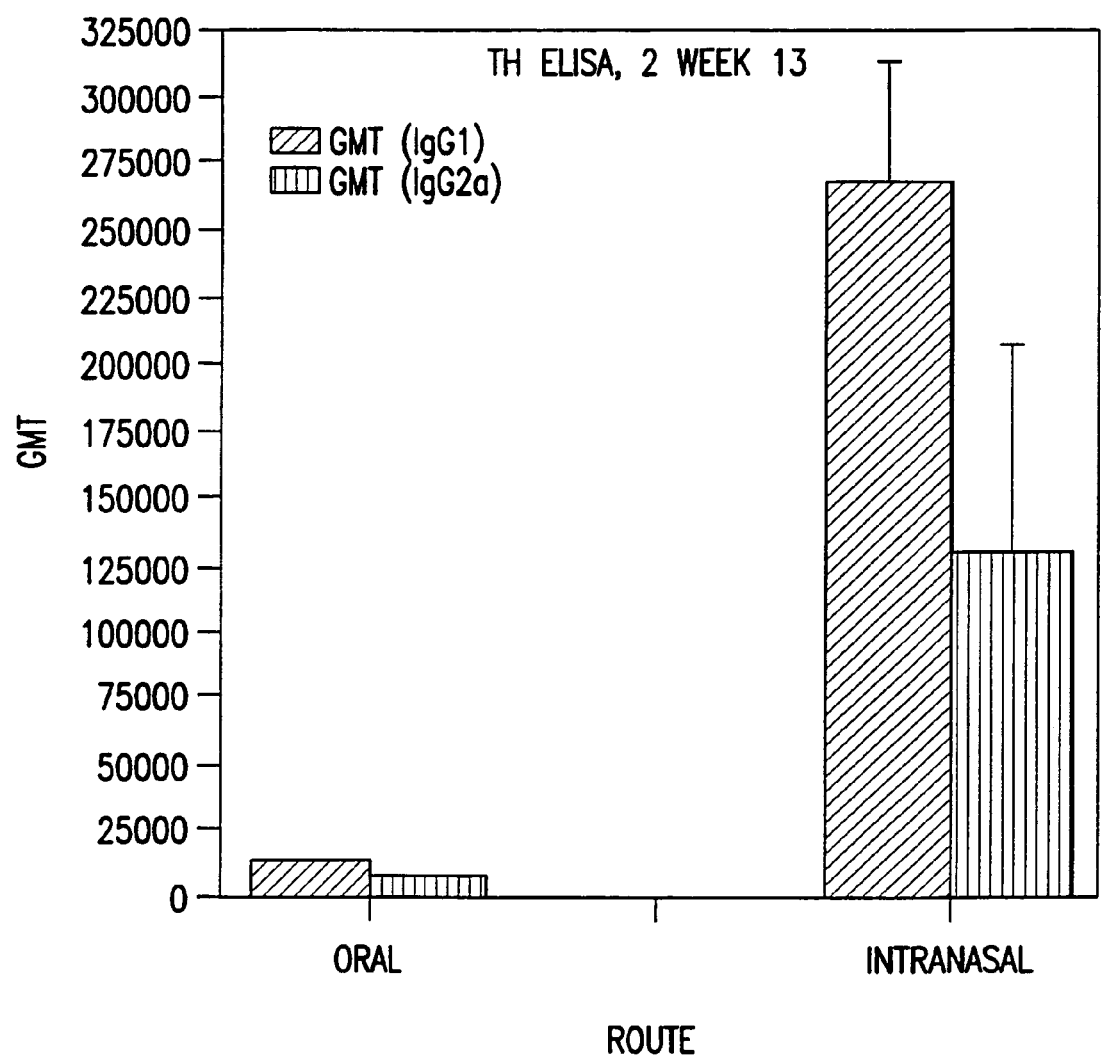
FIG. 12 depicts IgG1 and IgG2a antibody subclasses in BALB/c mice. Pre-challenge sera of BALB/c mice immunized orally or IN, with rotavirus 2/6-virus-like particles (VLPs) plus CT-$CRM_{E29H}$, were used to determine IgG subclasses. Standard deviations are shown.
Figure 13A:
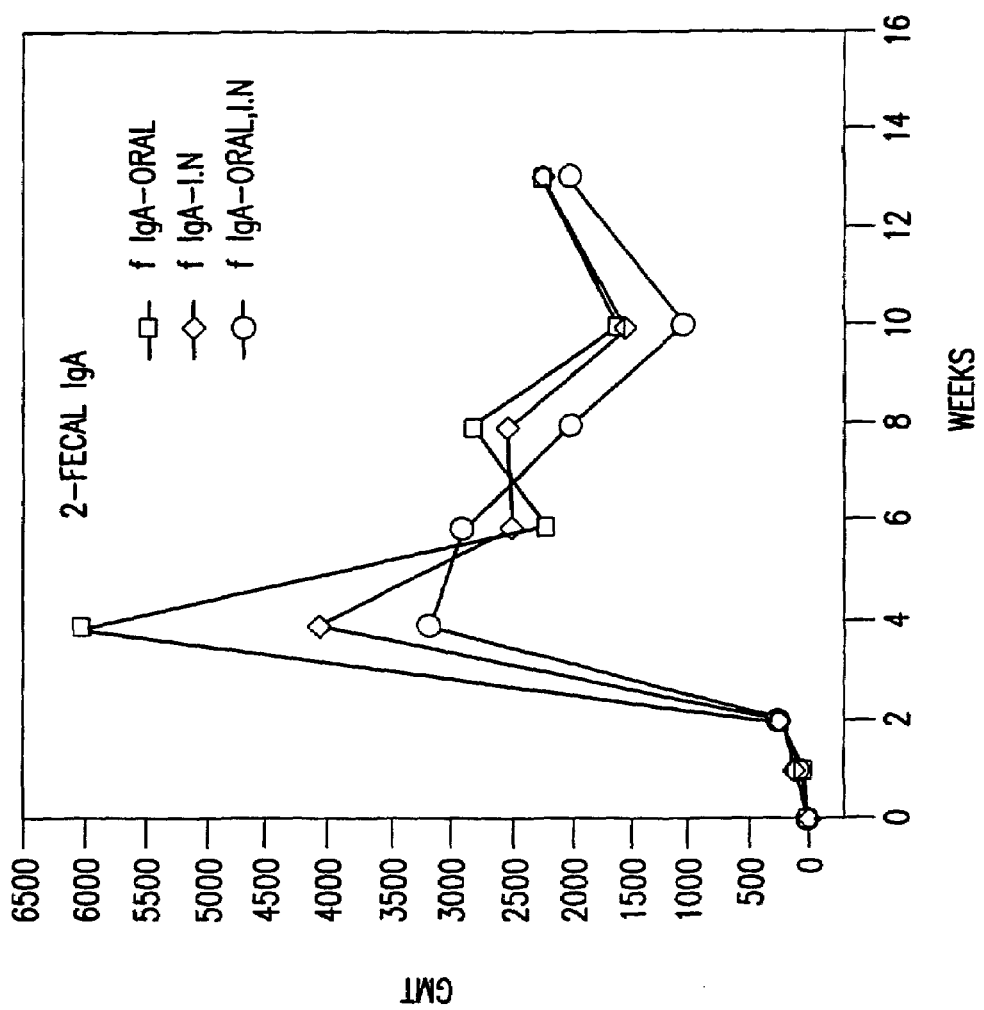
FIG. 13 depicts rotavirus-specific intestinal antibody responses in inbred BALB/c mice immunized with 2/6-VLPs. Groups of BALB/c mice were immunized with 2/6-VLPs plus CT-$CRM_{E29H}$ as described for FIG. 11, and levels of rotavirus-specific intestinal IgA (FIG. 13A) and IgG (FIG. 13B) were measured. No rotavirus-specific intestinal IgM was detected in any mice.
Figure 13B:
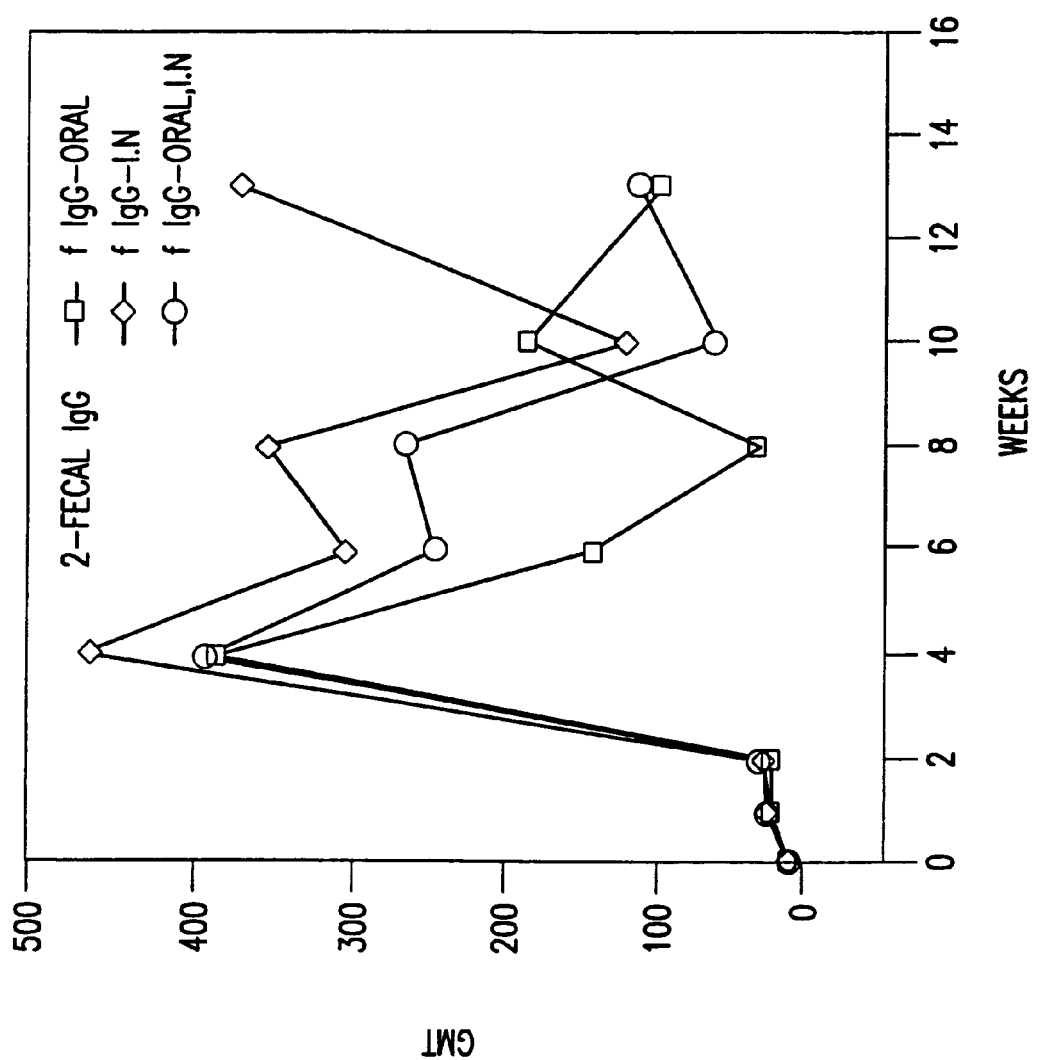

Mice were immunized as follows. BALB/c and CD-1 mice used in this study were purchased from Charles River Laboratories (Storeridge, N.Y.), bred in a rotavirus-free environment. Four week old BALB/c mice were immunized twice on week 0 and 2, either orally (n=4) or IN (n=5, n=4), with 100 and 10 μg of 2/6-VLPs respectively; each dose was formulated with 10 μg of CT-$CRM_{E29H}$. A third group of BALB/c mice (n=4) received 2/6-VLPs with CT-$CRM_{E29H}$ IN, followed by an oral booster immunization (i.e., mixed group). Control mice in this experiment were immunized with CT-$CRM_{E29H}$ (n=10), 1×TNC buffer (n=5) or 2/6-VLPs plus 1×TNC buffer (n=5). Each mouse was immunized IN with 20 μl of inoculum, 2 μl at a time, into alternating nares at one minute intervals. Serum and fecal samples were collected from all animals on weeks 0, 1, 2, 4, 6, 8, 10, 13 and the levels of rotavirus-specific serum IgG, IgM and IgA antibodies produced, as well as fecal IgG and IgA, were determined by ELISA. The serum antibody results are presented in FIGS. 10 and 11; the fecal antibody results are presented in FIG. 13. Week 13 serum samples were used to determine IgG1 and IgG2a subclasses. The antibody subclass results are presented in FIG. 12.

Pre-immunization sera diluted 1:100 and 1:2 dilutions of pre-immunization stool samples showed no reactivity in ELISA. Sera and stools from controls receiving only TNC buffer or CT-$CRM_{E29H}$ were analyzed in parallel. The control groups showed no rotavirus-specific serum or fecal antibodies throughout the study.

Four week old CD-1 mice were immunized three times orally (n=4) or IN (n=4) on weeks 0, 2 and 13 as above using CT-$CRM_{E29H}$ as the adjuvant. A control group (n=2) received CT-$CRM_{E29H}$ alone. Serum and stool samples were collected on weeks 0-9, 11-14, 26-28 and the levels of rotavirus-specific serum and fecal antibodies were determined.

For detection and quantification of IgG, IgM and IgA in stool and serum samples, 96-well polyvinyl chloride microtiter plates (Dynex Technologies, Chantilly, Va.) were coated with a hyperimmune guinea pig anti-SA11 rotavirus serum diluted in phosphate buffered saline (PBS) and incubated at 37° C. for four hours, or overnight at room temperature. The plates were then blocked with 5% BLOTTO (5% w/v nonfat powdered milk in PBS) at 37° C. for two hours. Suspended stool samples were diluted 1:1 in 1% BLOTTO and added to the plates. The plates were then incubated overnight at 4° C., after which they were washed three times with TNC buffer plus 0.05% Tween™ 20 (TNC-T). Rabbit anti-rhesus rotavirus hyperimmune serum was diluted in 1% BLOTTO plus 2.5% normal guinea pig serum (NGPS) and added to the plates for one hour at 37° C. The plates were then washed three times with TNC-T. Horseradish peroxidase-conjugated goat anti-rabbit IgG, IgM and IgA (Kirkegaard and Perry Laboratories, Gaithersburg, Md.) was diluted in 1% BLOTTO plus 2.5% NGPS and added to the plates, which were incubated for one hour at 37° C. The plates were then washed four times with TNC-T. TMB substrate (Kirkegaard and Perry Laboratories) was added, and the color reactions produced were allowed to develop for seven minutes at room temperature. The reaction was stopped by the addition of 1M phosphoric acid. The OD was determined at 450 nm using a micro-plate reader (BIO-TEK Instrument, Winooski, Vt.). Measurements of 0.1 above the blank were considered significant. SA11 stock virus was diluted in 1% BLOTTO and added to the plates, which were then incubated overnight at 4° C. The plates were washed three times with TNC-T; thereafter, stool samples diluted 1:1 in 1% BLOTTO or serum samples diluted serially in 1% BLOTTO were applied. As a negative control, duplicates of stool samples were added to a well with no anti-SA11 antibody coating. The plates were incubated for two hours at 37° C. and then washed three times with TNC-T. Peroxidase-conjugated goat anti-mouse IgG, IgM and IgA were diluted in 1% BLOTTO plus 2.5% NGPS and added to wells; peroxidase-conjugated goat anti-mouse IgA+IgG+IgM(H+L) antibodies were similarly diluted and added to wells for pre-immunization antibody detection. The plates were incubated for one hour at 37° C. and then washed four times with TNC-T. The plates were developed as described above for the antigen detection ELISA. The ELISA protocol used to determine IgG subclasses was a modification of the protocol described that employed HRP-labeled rat (monoclonal) anti-mouse IgG1 and IgG2a as the secondary antibodies (Biosource International, Camarillo, Calif.).

An immunohistochemical assay, described by Ishida et al (49), was modified and used to detect anti-rotaviral VP2 and VP6 antibodies in the serum of mice immunized with 2/6-VLPs. Briefly, early log phase Sf9 cells in shaker flasks were seeded into 96 well tissue culture plates at a density of $2.5 \times 10^4$ cell/well and then incubated one hour at room temperature (RT). Subsequently, cells were infected with recombinant baculoviruses encoding VP2 or VP6 genes at a multiplicity of infection of 10, and the infection was allowed to proceed at 28° C. for three days. The culture medium was then discarded, plates were dried in a vacuum oven at RT for one hour and fixed with 10% formalin (37% formaldehyde solution containing 10-15% methanol; Sigma) in PBS at RT for 30 minutes. Cells were subsequently permeablized with 1% Triton X-100 (Sigma) in TNC buffer at RT for five minutes.

Each set of infected cells expressing the designated rotavirus protein was exposed to pre-challenge or post-immunization serum from each BALB/c or CD-1 mouse, followed by immunostaining. Mouse serum samples were serially diluted in PBS with 5% FCS. Samples were added to the wells and the plates were incubated at 37° C. for two hours. Plates were then washed four times with PBS. Horseradish peroxidase labeled goat anti-mouse IgG, IgM or IgA antibody (Kirkegaard & Perry Laboratories) was added in PBS with 5% FCS, and incubated at 37° C. for one hour. Stained cells were detected with 3-amino-9-ethyl-carbazole substrate (AEC) (Sigma) after washing the wells twice with PBS. Uninfected Sf9 cells, serum from unimmunized mice, and pre-immunization sera from immunized mice were used as negative controls. Monoclonal antibodies against VP6 (7D9, 5E6) and VP2 (BP2) were used as positive controls (50).

Unimmunized animals and those immunized with 2/6-VLPs were challenged by gavage with 10 $SD_{50}$ of wild-type murine EDIM rotavirus (51) on week 26 (CD-1 mice) or on week 13 (BALB/c mice). The titer of EDIM strain was determined as shedding dose 50 ($SD_{50}$), the dose required to induce fecal viral shedding in 50% of adult mice. The trypsin-activated challenge virus (100 µl) was administered following oral administration of 100 µl of 4% sodium bicarbonate solution to neutralize gastric acidity. Viruses were diluted in M199 media (Irvine Scientific, Santa Ana, Calif.) and activated with 10 µl of trypsin stock (1 mg/ml) (Sigma Chemical Co, St. Louis, Mo.) per ml of viral stock solution. Following challenge, stool samples were collected from all animals for 9 days.

Figure 14B:
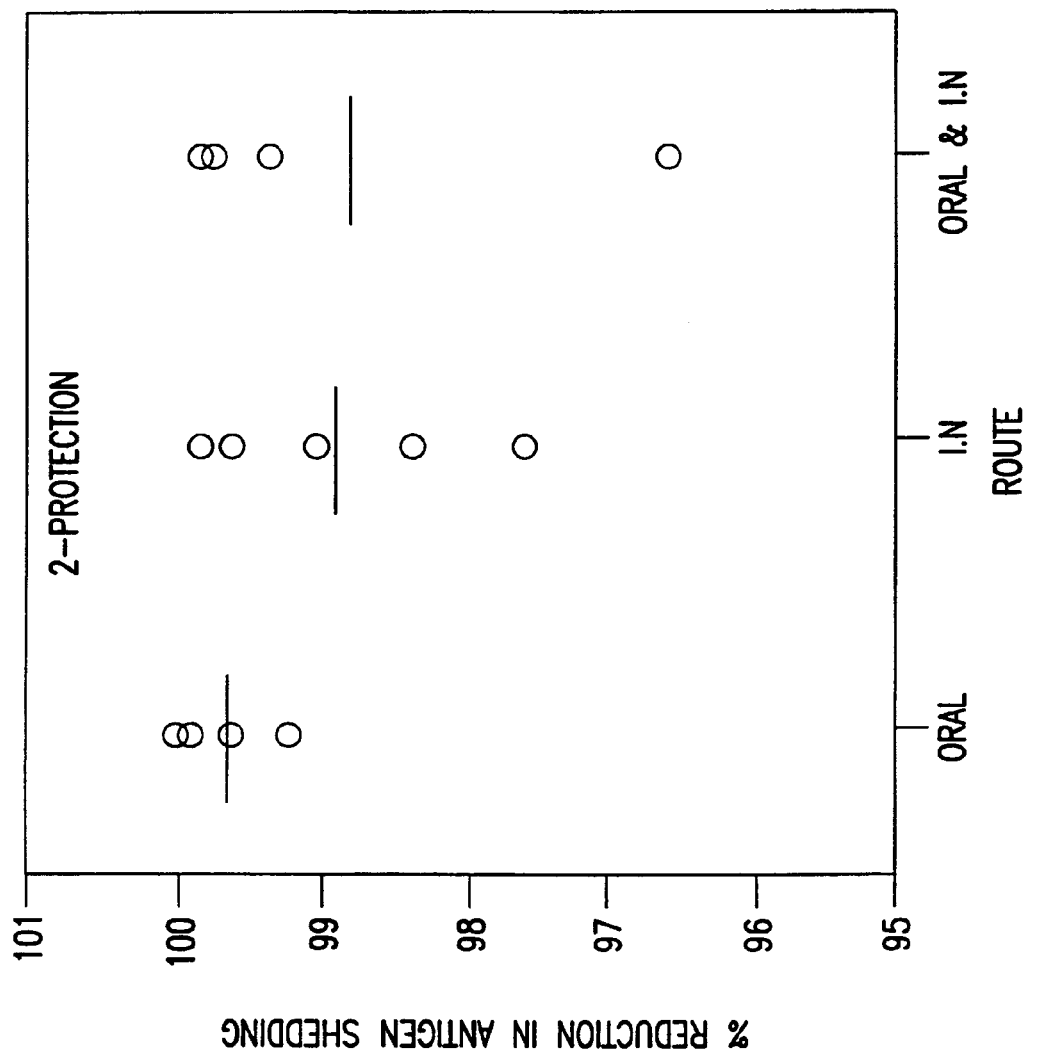
FIG. 14B depicts groups of BALB/c mice immunized with 2/6-VLP plus CT-$CRM_{E29H}$ by different routes as shown, and protection levels were determined as described above.
Figure 14C:
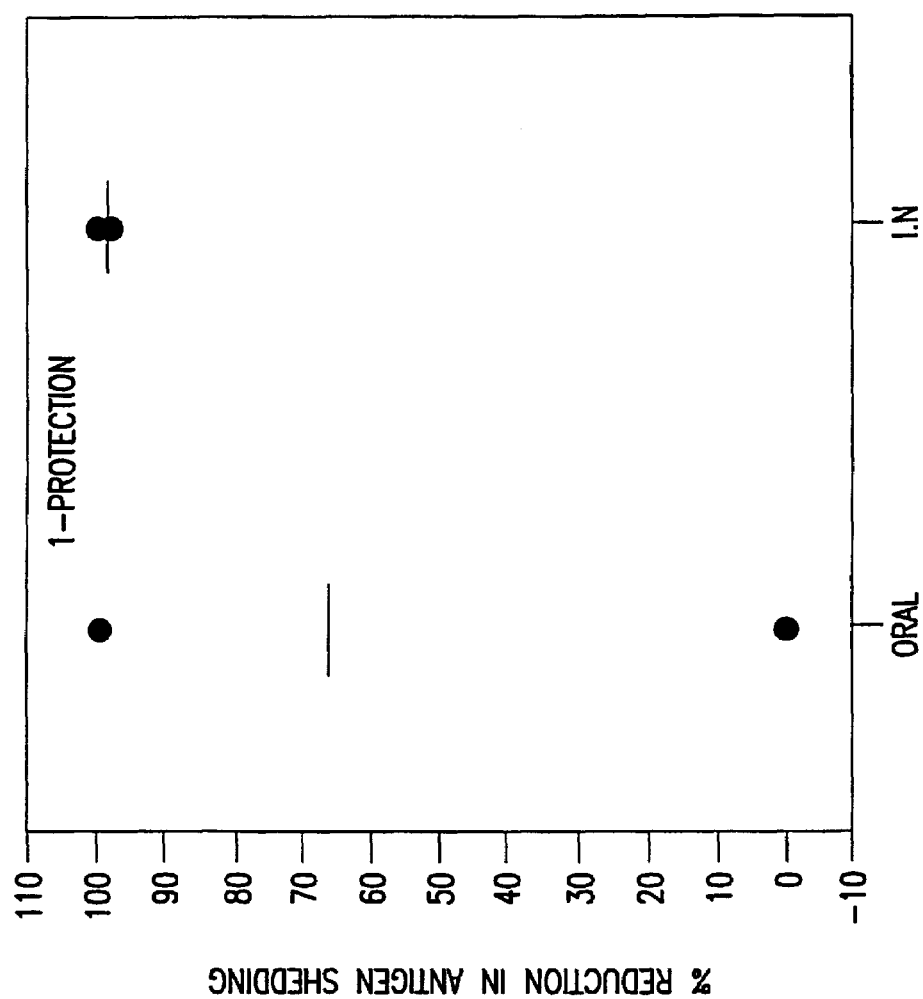
FIG. 14C depicts groups of outbred CD-1 mice immunized with 2/6-VLPs plus CT-$CRM_{E29H}$ orally and intranasally as described above. On week 26, immunized and control mice were challenged and PRAS calculated as described above. In the oral group (n=4), one mouse died before challenge (n=3 for protection).

Rotavirus antigen shedding in fecal samples was measured by ELISA and expressed as net optical density (OD) values, i.e., OD of the post-challenge fecal sample minus OD of the pre-challenge sample from the same mice. The area under the shedding curve for each animal was determined and the percent reduction in antigen shedding (PRAS) for each animal was calculated by comparing the area under the curve for each animal to the mean area of the control group. The mean PRAS was then calculated for each immunized group. Only PRAS levels above 50% were considered protective. The results are presented in FIG. 14.

Statistical analyses were performed with SPSS for version 8.0 for Windows (SPSS, Inc., Chicago, Ill.). Independent t tests were used to compare pre-challenge geometric mean titer values and to compare PRAS between groups. Up to three digits after the decimal point were considered in calculating P values (0.000=0).

Example 12

Increasing the Expression of CT-CRM$_{E29H}$ Through Use of an Arabinose Inducible Promoter The construction of the arabinose inducible system was as follows: PCR primers were synthesized to amplify the toxin encoding bicistron from pIIB29H.

Primer #1, CT29 Forward NheI: 5'-TTTTTTGGGCTAGCATGGAGGAAAAGATG AGC-3' (SEQ ID NO:6);

Primer #2, CT29 Reverse HindIII: 5'-GCAGGTCGAAGCTTGCATGTTTGGGC-3' (SEQ ID NO:7). The CT-$CRM_{E29H}$ ctxA and ctxB encoding PCR fragment was cloned into pBAD18-Cm using the endonuclease sites NheI and HindIII, resulting in construct pCT18. The ctxB (*V. cholerae* 2125) gene from pCT18 was removed using ClaI and HindIII and replaced with a similar fragment from plasmid pMGJ142 which was shown to encode a ctxB gene from *V. cholerae* strain 569B. The resulting construct, pPX7490 encodes the CT-$CRM_{E29H}$ ctxA and ctxB genes from strain 569B under control of the arabinose promoter, and has the LTIIb-B leader sequence.

Protocols for the large scale expression and purification of CT-$CRM_{E29H}$ were developed and are as follows: 3 L fluted Fernbach flasks were used, with 1 L per flask of Hy-Soy growth media (per liter: Hy-Soy 10 g; yeast extract 12.5 g; sodium chloride 5 g; sodium phosphate, monobasic 3.3 g; sodium phosphate, dibasic 13.1 g). For starter-stock preparation, 20 μg/ml chloramphenicol and 20 ml of sterile 50% glucose were added to one flask (1% final glucose concentration). The flask was then inoculated with 300 μl DH5α transformed with pPX7490, −70° C. frozen stock. The flask was incubated at 37° C. with shaking at 200 rpm overnight. All growth media to be used the following day was pre-warmed by shaking overnight at 37° C. at 200 rpm. The following day, a 1:40 dilution of the overnight culture was made into Hy-Sy growth media, supplemented with 20 μg/ml chloramphenicol and 10 ml sterile glycerol (1% final glycerol concentration) as a carbon source. This culture was outgrown at 37° C. to an $OD_{600}$ of 4.5-5.5 in Fernbach flasks (or higher in a bioreactor). The culture was then induced with 20 ml L-Arabinose (0.5% final concentration) and allowed to incubate for an additional three hours. After a three hour induction period, the majority of toxin was cell-associated. Cells were harvested by centrifugation and the pellet resuspended into 10 mM $NaPO_4$, 1 mM EDTA (pH 7.0) buffer at 9% of original culture volume. The cell suspension was mechanically disrupted through a microfluidizer and centrifuged for ten minutes at 8500×g to remove cellular debris. The cellular lysate (supernatant) was further clarified at 42,000 rpm for one hour in a 45Ti rotor, 160,000×$g_{AV}$. The clarified cell lysate was loaded onto a carboxymethyl(CM)-Sepharose™ column (Pharmacia) equilibrated with 10 mM $NaPO_4$ (pH 7.0). Approximately 300 ml CM-Sepharose™ was used per 10 liters of culture volume. The cell lysate was loaded onto the column at the rate of 0.102 cm/min (2 ml/min). The column was washed extensively with 10-15 column volumes of 10 mM $NaPO_4$ (pH 7.0) at 0.255 cm/min (5 ml/min) to remove contaminants. The CT-$CRM_{E29H}$ holotoxin was eluted with four column volumes of 10 mM $NaPO_4$ (pH 8.3) at 0.255 cm/min. The CT-$CRM_{E29H}$-containing eluate was buffer exchanged by filtration or dialyzed against PBS, then stored at 4° C.

Example 13

The Immune Responses of BALB/c Mice Immunized with Plasmid DNA Encoding the Full Length Glycoprotein D of Herpes Simplex Virus Type 2

Six to eight week old female BALB/c mice were immunized with plasmid DNA (pDNA) encoding the full length glycoprotein D of herpes simplex virus type 2 (gD2) (the plasmid containing the gD2 gene is described in Pachuk et al. (40), which is hereby incorporated by reference), formulated with 0.25% bupivacaine, and adjuvanted with wild-type CT, CT-$CRM_{E29H}$ or no adjuvant. Animals were given a secondary immunization three weeks following the primary and euthanised two weeks after the last injection. The protocol for immunization was as follows.

TABLE 33

| Group | Route of Delivery | Conc. of Plasmid | Conc. of Adjuvant | Volume Injected |
|---|---|---|---|---|
| Mouse 1 | ID | 50 μg 024 | 50 μg CT-$CRM_{E29H}$ | 10 μl |
| Mouse 2 | ID | 50 μg 024 | 50 μg CT | 10 μl |
| Mouse 3 | ID | 50 μg 024 | — | 10 μl |
| Mouse 4 | IM | 50 μg 024 | — | 100 μl |
| Mouse 5 | ID | 50 μg 023 | — | 10 μl |

024 - pDNA including gD2 gene; 023 = pDNA backbone without gD2 gene inserted
ID = Intradermal;
IM = Intramuscular
Group 4 served as a positive control; Group 5 served as a negative control.

A proliferation assay was conducted as follows: $1\times10^5$ spleen cells were cultured in the presence or absence of 200 ng/ml of gD2 protein in complete RPMI media with 10% FCS. After four days incubation at 37° C. in the presence of 5% $CO_2$, cultures were pulsed overnight with $^3[H]$. $^3[H]$ incorporation was measured on a beta counter. The counts were reported as SI (Stimulation Index=counts in presence of antigen stimulation divided by counts in absence of antigen stimulation). The results are presented in Table 34.

An ELISA was carried out to measure the antigen-specific humoral response in sera and vaginal washes. Briefly, 96 well flat bottom plates (Maxisorb, Nunc) were coated overnight at 4° C. with purified gD2 protein at a concentration of 0.4 µgs/ml. The plates were washed three times with PBS and blocked with 4% BSA for one hour at room temperature. Fifty microliters (1:100 dilution) of serum samples or 50 µl of vaginal wash sample was added to the plate. After incubation for one hour for sera and overnight at 4° C. for vaginal wash, the plates were washed with PBS five times, and a 1:3000 dilution of peroxidase-conjugated anti-mouse Ig (Sigma, St. Louis, Mo.) was added and the plates incubated for one hour. The plates were washed with PBS before adding the substrate 3,3',5,5'-tetramethylbenzidine (TMB) —$H_2O_2$ (Biotecx, Houston, Tex.). Color was allowed to develop for 30 minutes before reading at 450 nm on a $E_{max}$ microplate reader (Molecular Devices, Sunnyvale, Calif.). The results are presented in Table 35 (sera) and Table 36 (vaginal washes).

Cytokines were measured using a standard ELISA as described above. Plates were suitably coated to capture either IL-5 or gamma interferon from supernatants from 24 hour or 72 hour old gD2-stimulated cultures respectively. The results are presented in Table 37.

TABLE 34 gD2-Specific Cellular Proliferation Response (SI) After Administration of pDNA for HSV gD2 with CT or CT-CRM$_{E29H}$

| Group | ID CT | ID CT-CRM$_{E29H}$ |

20. Guidry, J. J., et al., *Infect. Immun.*, 65, 4943-4950 (1997).
21. U.S. Pat. No. 5,601,831.
22. U.S. Pat. No. 5,108,744.
23. International Patent Application number WO 96/05858.
24. Hu, L. T., et al., *Infect. Immun.*, 60, 2657-2666 (1992).
25. International Patent Application number PCT/US99/09486, filed Apr. 29, 1999.
26. European Patent Application number 449,958.
27. Walsh, E. E., et al., *Infect. Immun.*, 43, 756-758 (1984).
28. Crawford, S. E., et al., *J. Virology*, 68, 5945-5952 (1994).
29. Lee, A. J., et al., *Gastroenterology*, 112, 1386-1397 (1997).
30. Snider, D. P., et al., *J. Immunol.* 153, 647-657 (1994).
31. Tamura, S. Y., et al., *Vaccine*, 12, 1238-1240 (1994).
32. Van der Akker, F., et al., *Structure*, 4, 665-678 (1996).
33. Rudin A., et al., *Infect. Immun.*, 66, 3390-3396 (1998).
34. O'Neal, C. M., et al., *J. Virology*, 71, 8707-8717 (1997).
35. O'Neal C. M., et al., *J. Virology*, 72, 3390-3393 (1998).
36. International Patent Application number WO 93/13202.
37. International Patent Application number WO 98/42375.
38. International Patent Application number WO 98/20734.
39. U.S. Pat. No. 5,593,972.
40. Pachuk, C., et al., *Curr. Topics Microbiol. Immunol.*, 226, 79-89 (1998).
41. Jobling, M. G., and Holmes, R. K., *Infect. Immun.*, 60, 4915-4924 (1992).
42. Jobling, M. G., and Holmes, R. K., *Mol. Microbiol.*, 5, 1755-1767 (1991).
43. Kunkel, T. A., *Proc. Natl. Acad. Sci., USA*, 82, 488-492 (1985).
44. Sanger, F., et al., *Proc. Natl. Acad. Sci., USA*, 74, 5463-5467 (1977).
45. Tartof, K. D., and Hobbs, C. A., *Focus*, 9, 12 (1987).
46. Karasic, R., et al., *Ped. Inf. Dis. J.*, 8 (Suppl.), S62-65 (1988).
47. Hansen, E. J., et al., *Infect. Immun.*, 56, 182-190 (1988).
48. Laemmli, U. K., *Nature (London)*, 227, 680-685 (1970).
49. Ishida, S. I., et al., *J. Clin. Microbiol.*, 34, 1694-1700 (1996).
50. Burns, J. W., et al., *Science*, 272, 104-107 (1996).
51. McNeal, M. M., and Ward, R. L., *Virology*, 211, 474-480 (1995).

What is claimed is:

1. An antigenic composition comprising
   (a) at least one antigen from a pathogenic organism selected from the group consisting of a bacterium, a virus, a fungus and a parasite; and
   (b) an effective adjuvanting amount of a mutant cholera holotoxin, wherein the mutant holotoxin has reduced toxicity compared to wild-type cholera holotoxin, and has a histidine which replaces the glutamic acid which naturally occurs at position 29 of the A subunit of the wild-type cholera holotoxin and wherein said mutant holotoxin enhances the immune response in a vertebrate host to said antigen.

2. An antigenic composition comprising
   (a) at least one antigen selected from the group consisting of the *Haemophilus influenzae* P4 outer membrane proteins the *Haemophilus influenzae* P6 outer membrane protein, the *Haemophilus influenzae* adherence and penetration protein (Hap$_S$), the *Helicobacter pylori* urease protein, the *Neisseria meningitidis* Group B recombinant class 1 pilin (rpilin), the *Neisseria meningitidis* Group B class 1 outer membrane protein (PorA), the respiratory syncytial virus fusion protein, a rotavirus virus-like particle and the herpes simplex virus (HSV) type 2 glycoprotein D (gD2); and
   (b) an effective adjuvanting amount of a mutant cholera holotoxin, wherein the mutant holotoxin has reduced toxicity compared to a wild-type cholera holotoxin, and has an amino acid which replaces the deleted glutamic acid which naturally occurs at position 29 of the mature A subunit of the wild-type cholera holotoxin, wherein said amino acid is other than aspartic acid, and wherein said mutant holotoxin enhances the immune response in a vertebrate host to said antigen.

3. The antigenic composition of claim 2 wherein the antigen is selected from the group consisting of the *Haemophilus influenzae* P4 outer membrane protein, the *Haemophilus influenzae* P6 outer membrane protein, the *Haemophilus influenzae* Hap$_S$ protein, and any combination thereof.

4. The antigenic composition of claim 2 wherein the antigen is the *Helicobacter pylori* urease protein.

5. The antigenic composition of claim 2 the antigen is selected from the group consisting of the *Neisseria meningitidis* rpilin, *Neisseria meningitidis* PorA protein and any combination thereof.

6. The antigenic composition of claim 2 wherein the antigen is the respiratory syncytial virus fusion protein.

7. The antigenic composition of claim 2 wherein the antigen is a rotavirus virus-like particle.

8. The antigenic composition of claim 7 wherein the virus-like particle is a rotavirus 2/6-virus-like particle.

9. The antigenic composition of claim 2 wherein the antigen is HSV gD2.

10. An antigenic composition comprising
    (a) at least one antigen from a pathogenic organism selected from the group consisting of a bacterium, a virus, a fungus and a parasite;
    (b) an effective adjuvanting amount of a mutant cholera holotoxin, wherein the mutant holotoxin has reduced toxicity compared to a wild-type cholera holotoxin, and has an amino acid which replaces the deleted glutamic acid which naturally occurs at position 29 of the mature A subunit of the wild-type cholera holotoxin, wherein said amino acid is other than aspartic acid, and wherein said mutant holotoxin enhances the immune response in a vertebrate host to said antigen; and
    (c) a second adjuvant in addition to the mutant cholera holotoxin.

11. An antigenic composition comprising
    (a) at least one antigen from a pathogenic organism selected from the group consisting of a bacterium, a virus, a fungus and a parasite;
    (b) an effective adjuvanting amount of a mutant cholera holotoxin, wherein the mutant holotoxin has reduced toxicity compared to a wild-type cholera holotoxin, and has an amino acid which replaces the deleted glutamic acid which naturally occurs at position 29 of the mature A subunit of the wild-type cholera holotoxin, wherein said amino acid is other than aspartic acids and wherein said mutant holotoxin enhances the immune response in a vertebrate host to said antigen; and
    (c) at least one additional mutation in the A subunit of the mutant cholera holotoxin at a position other than said wild-type amino acid position 29.

12. The antigenic composition of claim 11 wherein the at least one additional mutation is made as a substitution for a naturally-occurring amino acid at an amino acid position of wild-type cholera holotoxin selected from the group consisting of the arginine at amino acid 7, the aspartic acid at position 9, the arginine at position 11, the histidine at position 44, the valine at position 53, the arginine at position 54, the serine at position 61, the serine at position 63, the histidine at position 70, the valine at position 97, the tyrosine at position 104, the proline at position 106, the histidine at position 107, the serine at position 109, the glutamic acid at position 100, the glutamic acid at position 112, the serine at position 114, the tryptophan at position 127, the arginine at position 146 and the arginine at position 192.

13. A method for increasing the ability of an antigenic composition containing at least one antigen from a pathogenic organism selected from the group consisting of a bacterium, a virus, a fungus or a parasite to elicit the immune response of a vertebrate host, which comprises administering to said host an antigenic composition comprising
   (a) at least one antigen from a pathogenic organism selected from the group consisting of a bacterium, a virus, a fungus and a parasite; and
   (b) an effective adjuvanting amount of a mutant cholera holotoxin, wherein the mutant holotoxin has reduced toxicity compared to a wild-type cholera holotoxin, and has an amino acid which replaces the deleted glutamic acid which naturally occurs at position 29 of the mature A subunit of the wild-type cholera holotoxin, wherein said amino acid is other than aspartic acid, and wherein said mutant holotoxin enhances the immune response in a vertebrate host to said antigen.

14. The method of claim 13 wherein the antigenic composition comprises more than one antigen.

15. The method of claim 13 wherein the amino acid substituted at wild-type position 29 is histidine.

16. The method of claim 13 wherein the antigen is selected from the group consisting of the *Haemophilus influenzae* P4 outer membrane protein, the *Haemophilus influenzae* P6 outer membrane protein, the *Haemophilus influenzae* Hap$_S$ protein, the *Helicobacter pylori* urease protein, the *Neisseria meningitidis* rpilin, the *Neisseria meningitidis* PorA protein, the respiratory syncytial virus fusion protein, a rotavirus, virus-like particle and HSV gD2.

17. The method of claim 16 wherein at least one antigen is selected from the group consisting of the *Haemophilus influenzae* P4 outer membrane protein, the *Haemophilus influenzae* P6 outer membrane protein, the *Haemophilus influenzae* Hap$_S$ protein, and any combination thereof.

18. The method of claim 16 wherein the antigen is the *Helicobacter pylori* urease protein.

19. The method of claim 16 wherein at least one antigen is selected from the group consisting of the *Neisseria meningitidis* rpilin, *Neisseria meningitidis* PorA protein and any combination thereof.

20. The method of claim 16 wherein the antigen is the respiratory syncytial virus fusion protein.

21. The method of claim 16 wherein the antigen is a rotavirus virus-like particle.

22. The method of claim 21 wherein the virus-like particle is a rotavirus 2/6-virus-like particle.

23. The method of claim 16 wherein the antigen is HSV gD2.

24. The method of claim 13 wherein the antigenic composition further comprises a diluent or carrier.

25. The method of claim 13 wherein the antigenic composition further comprises a second adjuvant in addition to the mutant cholera holotoxin.

26. The method of claim 13 wherein at least one additional mutation is made to the A subunit of the mutant cholera bolotoxin at a position other than said wild-type amino acid position 29, wherein said mutant holotoxin with said additional mutation enhances the immune response in a vertebrate host to said antigen.

27. The method of claim 26 wherein the at least one additional mutation is made as a substitution for a naturally-occurring amino acid of wild-type cholera holotoxin selected from the group consisting of the arginine at amino acid 7, the aspartic acid at position 9, the arginine at position 11, the histidine at position 44, the valine at position 53, the arginine at position 54, the serine at position 61, the serine at position 63, the histidine at position 70, the valine at position 97, the tyrosine at position 104, the proline at position 106, the histidine at position 107, the serine at position 109, the glutamic acid at position 100, the glutamic acid at position 112, the serine at position 114, the tryptophan at position 127, the arginine at position 146 and the arginine at position 192.

28. A method of preparing an antigenic composition comprising combining
   (a) at least one antigen from a pathogenic organism selected from the group consisting of a bacterium, a virus, a fungus and a parasite; and
   (b) an effective adjuvanting amount of a mutant cholera holotoxin, wherein the mutant holotoxin has reduced toxicity compared to wild-type cholera holotoxin and has a substitution which replaces the glutamic acid which naturally occurs at position 29 of the A subunit of the wild-type cholera holotoxin with an amino acid other than aspartic acid, and wherein said mutant holotoxin enhances the immune response in a vertebrate host to said antigen.

29. A method for increasing the ability of an antigenic composition containing at least one antigen from a pathogenic organism selected from the group consisting of a bacterium, a virus, a fungus or a parasite to elicit the immune response of a vertebrate host, which comprises administering to said host an antigenic composition of claim 1.

* * * * *